US012257218B2

(12) United States Patent
Cavatur et al.

(10) Patent No.: US 12,257,218 B2
(45) Date of Patent: *Mar. 25, 2025

(54) PHARMACEUTICAL FORMULATION

(71) Applicant: RB HEALTH (US) LLC, Parsippany, NJ (US)

(72) Inventors: Raghu Cavatur, Parsippany, NJ (US);
Kevin Chen, Parsippany, NJ (US);
Matthew Kaser, Parsippany, NJ (US);
Hongchun Qiu, Parsippany, NJ (US);
Ernest Joseph Woodhouse, Slough (GB); Josef Borovicka, Slough (GB);
Elliot Wilkinson, Slough (GB)

(73) Assignee: RB HEALTH (US) LLC, Parsippany, NJ (US)

( * ) Notice: Subject to any disclaimer, the term of this patent is extended or adjusted under 35 U.S.C. 154(b) by 5 days.

This patent is subject to a terminal disclaimer.

(21) Appl. No.: 17/667,746

(22) Filed: Feb. 9, 2022

(65) Prior Publication Data

US 2023/0062872 A1 Mar. 2, 2023

Related U.S. Application Data

(63) Continuation of application No. 15/291,061, filed on Oct. 11, 2016, now Pat. No. 11,278,506.

(60) Provisional application No. 62/239,775, filed on Oct. 9, 2015, provisional application No. 62/239,780, filed on Oct. 9, 2015.

(51) Int. Cl.
*A61K 31/192* (2006.01)
*A61K 9/20* (2006.01)
*A61K 9/24* (2006.01)
*A61K 9/48* (2006.01)
(Continued)

(52) U.S. Cl.
CPC .......... *A61K 31/192* (2013.01); *A61K 9/2009* (2013.01); *A61K 9/2013* (2013.01); *A61K 9/2031* (2013.01); *A61K 9/2054* (2013.01); *A61K 9/209* (2013.01); *A61K 9/4808* (2013.01); *A61K 9/4858* (2013.01);
(Continued)

(58) Field of Classification Search
None
See application file for complete search history.

(56) References Cited

U.S. PATENT DOCUMENTS 2,738,303 A 3/1956 Blythe
2,951,792 A 9/1960 Swintosky
(Continued)

FOREIGN PATENT DOCUMENTS

CN 201257161 Y 6/2009
CN 202211874 5/2012
(Continued)

OTHER PUBLICATIONS

*Adams Respiratory Therapeutics, Inc., et al. v. Perrigo Company, et al.*, Defendants' First Supplemental Responses And Objections To Adams' Second Set of Interrogatories (Nos. 13-14) (W.D. Mich. Jun. 30, 2009).

(Continued)

*Primary Examiner* — Bethany P Barham
*Assistant Examiner* — Barbara S Frazier
(74) *Attorney, Agent, or Firm* — Venable LLP

(57) ABSTRACT

A formulation for oral administration comprises an expectorant, an analgesic, and at least one additional active ingredient having a modified release providing a therapeutic effect for each of the active ingredients for up to 12 hours.

8 Claims, 29 Drawing Sheets

(51) Int. Cl.
*A61K 31/09* (2006.01)
*A61K 31/485* (2006.01)

(52) U.S. Cl.
CPC ............ *A61K 9/4866* (2013.01); *A61K 31/09* (2013.01); *A61K 31/485* (2013.01)

(56) References Cited

U.S. PATENT DOCUMENTS

| | | |
|---|---|---|
| 3,065,143 A | 11/1962 | Christenson et al. |
| 3,362,880 A | 1/1968 | Sampson |
| 3,362,881 A | 1/1968 | Klaus et al. |
| 3,458,622 A | 7/1969 | Hill |
| 3,555,151 A | 1/1971 | Kaplan et al. |
| 3,558,768 A | 1/1971 | Klippel |
| 3,634,584 A | 1/1972 | Poole |
| 3,870,790 A | 3/1975 | Lowey et al. |
| 3,981,984 A | 9/1976 | Signorino |
| 4,122,157 A | 10/1978 | Huber |
| 4,140,755 A | 2/1979 | Sheth et al. |
| 4,167,558 A | 9/1979 | Sheth et al. |
| 4,226,849 A | 10/1980 | Schor |
| 4,248,857 A | 2/1981 | DeNeale et al. |
| 4,248,858 A | 2/1981 | Guley et al. |
| 4,259,314 A | 3/1981 | Lowey |
| 4,308,251 A | 12/1981 | Dunn et al. |
| 4,309,404 A | 1/1982 | DeNeale et al. |
| 4,309,405 A | 1/1982 | Guley |
| 4,357,469 A | 11/1982 | Schor |
| 4,369,172 A | 1/1983 | Schor et al. |
| 4,389,393 A | 6/1983 | Schor et al. |
| 4,424,235 A | 1/1984 | Sheth et al. |
| 4,540,566 A | 9/1985 | Davis et al. |
| 4,543,370 A | 9/1985 | Porter et al. |
| 4,552,899 A | 11/1985 | Sunshine et al. |
| 4,619,934 A | 10/1986 | Sunshine et al. |
| 4,680,323 A | 7/1987 | Lowey |
| 4,695,464 A | 9/1987 | Alderman |
| 4,699,779 A | 10/1987 | Palinczar |
| 4,704,285 A | 11/1987 | Alderman |
| 4,738,966 A | 4/1988 | Sunshine et al. |
| 4,749,697 A | 6/1988 | Sunshine et al. |
| 4,749,711 A | 6/1988 | Sunshine et al. |
| 4,749,720 A | 6/1988 | Sunshine et al. |
| 4,749,721 A | 6/1988 | Sunshine et al. |
| 4,749,722 A | 6/1988 | Sunshine et al. |
| 4,749,723 A | 6/1988 | Sunshine et al. |
| 4,756,911 A | 7/1988 | Drost |
| 4,795,643 A | 1/1989 | Seth |
| 4,798,725 A | 1/1989 | Patel |
| 4,814,179 A | 3/1989 | Bolton et al. |
| 4,826,688 A | 5/1989 | Panoz |
| 4,834,965 A | 5/1989 | Martani et al. |
| 4,834,984 A | 5/1989 | Goldie et al. |
| 4,839,354 A | 6/1989 | Sunshine et al. |
| 4,851,392 A | 7/1989 | Shaw et al. |
| 4,871,548 A | 10/1989 | Edgren et al. |
| 4,900,557 A | 2/1990 | Dell et al. |
| 4,920,149 A | 4/1990 | Sunshine et al. |
| 4,968,508 A | 11/1990 | Oren et al. |
| 4,971,805 A | 11/1990 | Kitanishi et al. |
| 4,980,170 A | 12/1990 | Schneider et al. |
| 4,983,398 A | 1/1991 | Gaylord et al. |
| 4,990,341 A | 2/1991 | Goldie et al. |
| 4,994,276 A | 2/1991 | Balchwal et al. |
| 5,004,613 A | 4/1991 | Radebaugh et al. |
| 5,032,406 A | 7/1991 | Dansereau |
| 5,047,248 A | 9/1991 | Calanchi et al. |
| 5,085,865 A | 2/1992 | Nayak |
| 5,098,715 A | 3/1992 | McCabe et al. |
| 5,133,974 A | 7/1992 | Paradissi |
| 5,164,398 A | 11/1992 | Sims et al. |
| 5,186,943 A | 2/1993 | Okada et al. |
| 5,186,963 A | 2/1993 | Howman |
| 5,200,193 A | 4/1993 | Radebaugh et al. |
| 5,260,073 A | 11/1993 | Phipps |
| 5,286,493 A | 2/1994 | Oshlack et al. |
| 5,292,534 A | 3/1994 | Valentine et al. |
| 5,326,571 A | 7/1994 | Wright et al. |
| 5,358,717 A | 10/1994 | Kuramoto et al. |
| 5,368,861 A | 11/1994 | Ushimaru et al. |
| 5,376,384 A | 12/1994 | Eichel et al. |
| 5,395,626 A | 3/1995 | Kotwal et al. |
| 5,403,593 A | 4/1995 | Royce |
| 5,427,799 A | 6/1995 | Valentine et al. |
| 5,445,829 A | 8/1995 | Paradissis et al. |
| 5,451,409 A | 9/1995 | Rencher et al. |
| 5,470,580 A | 11/1995 | Kuramoto et al. |
| 5,472,704 A | 12/1995 | Santus et al. |
| 5,486,364 A | 1/1996 | King et al. |
| 5,494,681 A | 2/1996 | Cuca et al. |
| 5,529,791 A | 6/1996 | Deboeck et al. |
| 5,576,022 A | 11/1996 | Yang et al. |
| 5,593,694 A | 1/1997 | Hayashida |
| 5,650,169 A | 7/1997 | Conte et al. |
| 5,656,296 A | 8/1997 | Khan |
| 5,662,933 A | 9/1997 | Baichwal et al. |
| 5,738,874 A | 4/1998 | Conte et al. |
| 5,773,031 A | 6/1998 | Shah et al. |
| 5,773,032 A | 6/1998 | Engel |
| 5,780,057 A | 7/1998 | Conte et al. |
| 5,807,580 A | 9/1998 | Luber |
| 5,840,329 A | 11/1998 | Bai |
| 5,859,060 A | 1/1999 | Platt |
| 5,945,123 A | 8/1999 | Hermelin |
| 5,968,554 A | 10/1999 | Beiman et al. |
| 5,993,858 A | 11/1999 | Crison et al. |
| 6,120,802 A | 9/2000 | Breitenbach et al. |
| 6,165,506 A | 12/2000 | Jain et al. |
| 6,210,710 B1 | 4/2001 | Skinner |
| 6,217,903 B1 | 4/2001 | Skinner |
| 6,217,904 B1 | 4/2001 | Midha et al. |
| 6,294,199 B1 | 9/2001 | Conley |
| 6,312,724 B1 | 11/2001 | Odidi et al. |
| 6,340,476 B1 | 1/2002 | Midha et al. |
| 6,372,252 B1 | 4/2002 | Blume |
| 6,372,254 B1 | 4/2002 | Ting et al. |
| 6,475,521 B1 | 11/2002 | Timmins et al. |
| 6,555,136 B2 | 4/2003 | Midha |
| 6,623,756 B1 | 9/2003 | Wilber et al. |
| 6,730,321 B2 | 5/2004 | Ting et al. |
| 6,838,094 B2 | 1/2005 | Grimmett et al. |
| 6,955,821 B2 | 10/2005 | Davis |
| 7,838,032 B2 | 11/2010 | Davis |
| 8,999,388 B2 | 4/2015 | Lim et al. |
| 9,023,390 B2 | 5/2015 | Wertz et al. |
| 9,066,942 B2 | 6/2015 | Giliyar et al. |
| 9,149,533 B2 | 10/2015 | Guido et al. |
| 9,220,704 B2 | 12/2015 | Kim et al. |
| 9,456,985 B2 | 10/2016 | Wertz et al. |
| 9,545,448 B2 | 1/2017 | Guido et al. |
| 9,572,780 B2 | 2/2017 | Lim et al. |
| 9,579,389 B2 | 2/2017 | Guido et al. |
| 9,655,971 B2 | 5/2017 | Guido et al. |
| 9,662,399 B2 | 5/2017 | Guido et al. |
| 10,478,504 B2 | 11/2019 | Guido et al. |
| 10,576,041 B2 | 3/2020 | Stella et al. |
| 10,792,364 B2 | 10/2020 | Guido et al. |
| 11,433,030 B2 | 9/2022 | Stella et al. |
| 11,576,974 B2 | 2/2023 | Guido et al. |
| 11,813,361 B2 | 11/2023 | Mohammad |
| 2002/0022058 A1 | 2/2002 | Lovercheck |
| 2002/0058061 A1 | 5/2002 | Midha et al. |
| 2002/0142044 A1 | 10/2002 | Vendola |
| 2002/0164371 A1 | 11/2002 | Ting et al. |
| 2003/0012820 A1 | 1/2003 | Upadhyay |
| 2003/0039691 A1 | 2/2003 | Waterman |
| 2003/0049318 A1 | 3/2003 | Davis et al. |
| 2003/0091624 A1 | 5/2003 | Szymczak et al. |
| 2003/0147952 A1 | 8/2003 | Lim et al. |
| 2003/0180352 A1 | 9/2003 | Patel |
| 2003/0194439 A1 | 10/2003 | Midha et al. |
| 2003/0215508 A1 | 11/2003 | Davis et al. |
| 2004/0022851 A1 | 2/2004 | Davis et al. |
| 2004/0033258 A1 | 2/2004 | Koike |

(56) References Cited

U.S. PATENT DOCUMENTS

| | | |
|---|---|---|
| 2004/0156902 A1 | 8/2004 | Lee et al. |
| 2004/0180085 A1 | 9/2004 | Ohkouchi et al. |
| 2005/0013863 A1 | 1/2005 | Lim et al. |
| 2005/0095288 A1 | 5/2005 | Honea |
| 2005/0152967 A1 | 7/2005 | Tengler et al. |
| 2005/0276852 A1 | 12/2005 | Davis et al. |
| 2006/0127473 A1 | 6/2006 | Nichols |
| 2007/0134317 A1 | 6/2007 | Gruber |
| 2008/0014274 A1 | 1/2008 | Bubnis et al. |
| 2009/0202633 A1 | 8/2009 | Velaga et al. |
| 2012/0201887 A1 | 8/2012 | Ahlgren et al. |
| 2012/0252833 A1 | 10/2012 | Wertz et al. |
| 2012/0263792 A1 | 10/2012 | Lim et al. |
| 2013/0172381 A1 | 7/2013 | Giliyar et al. |
| 2014/0179728 A1 | 6/2014 | Giliyar et al. |
| 2014/0179729 A1 | 6/2014 | Giliyar et al. |
| 2014/0186515 A1 | 7/2014 | Lim et al. |
| 2014/0221416 A1 | 8/2014 | Guido et al. |
| 2014/0227356 A1 | 8/2014 | Kim et al. |
| 2015/0098992 A1 | 4/2015 | Kim et al. |
| 2015/0196555 A1 | 7/2015 | Guido et al. |
| 2015/0196556 A1 | 7/2015 | Guido et al. |
| 2015/0196557 A1 | 7/2015 | Guido et al. |
| 2015/0202300 A1 | 7/2015 | Guido et al. |
| 2015/0238423 A1 | 8/2015 | Wertz et al. |
| 2015/0283084 A1 | 10/2015 | Mohammad |
| 2015/0320686 A1 | 11/2015 | Giliyar et al. |
| 2016/0030352 A1 | 2/2016 | Lim et al. |
| 2016/0256454 A1 | 9/2016 | Giliyar et al. |
| 2017/0202817 A1 | 7/2017 | Lim et al. |
| 2017/0296671 A1 | 10/2017 | Guido et al. |
| 2017/0304210 A1 | 10/2017 | Ahlgren et al. |
| 2017/0304296 A1 | 10/2017 | Cavatur et al. |
| 2018/0071277 A1 | 3/2018 | Giliyar et al. |
| 2018/0085317 A1 | 3/2018 | Stella et al. |
| 2019/0209551 A1 | 7/2019 | Giliyar et al. |
| 2019/0240333 A1 | 8/2019 | Guido et al. |
| 2020/0085317 A1 | 3/2020 | Bushi |
| 2020/0113841 A1 | 4/2020 | Stella et al. |
| 2020/0390892 A1 | 12/2020 | Guido et al. |
| 2022/0079937 A1 | 3/2022 | Cavatur et al. |
| 2023/0293695 A1 | 9/2023 | Guido et al. |
| 2024/0041777 A1 | 2/2024 | Ahlgren et al. |
| 2024/0180839 A1 | 6/2024 | Mohammad |

FOREIGN PATENT DOCUMENTS

| | | |
|---|---|---|
| EP | 0409781 B1 | 6/1994 |
| EP | 0 875 245 A2 | 9/1999 |
| GB | 2255344 A | 11/1992 |
| JP | 7277962 | 10/1995 |
| JP | 2001-187737 A | 7/2001 |
| WO | 85/04589 A1 | 10/1985 |
| WO | 87/00044 | 1/1987 |
| WO | 91/17746 A1 | 11/1991 |
| WO | 92/04022 A1 | 3/1992 |
| WO | 94/06416 A1 | 3/1994 |
| WO | 94/27557 A2 | 12/1994 |
| WO | 95/19759 A1 | 7/1995 |
| WO | 95/20946 A1 | 8/1995 |
| WO | 95/28148 A1 | 10/1995 |
| WO | 96/04908 A1 | 2/1996 |
| WO | 97/09042 A1 | 3/1997 |
| WO | 98/05305 A1 | 2/1998 |
| WO | 98/22091 A1 | 5/1998 |
| WO | 98/22097 | 5/1998 |
| WO | 99/17745 A1 | 4/1999 |
| WO | 00/10537 A1 | 3/2000 |
| WO | 00/33818 A1 | 6/2000 |
| WO | 00/59479 A1 | 10/2000 |
| WO | 01/19901 A2 | 3/2001 |
| WO | 2003/088952 A1 | 10/2003 |
| WO | 2010/121326 A1 | 10/2010 |
| WO | 2013/055177 A1 | 4/2013 |
| WO | 2013/154390 A1 | 10/2013 |
| WO | 2016/063055 A1 | 4/2016 |
| WO | 2016/063057 A1 | 4/2016 |

OTHER PUBLICATIONS

*Adams Respiratory Therapeutics, Inc., et al. v. Perrigo Company, et al.*, Expert Report of Walter G. Chambliss—Redacted (W.D. Mich. Aug. 10, 2009).

*Adams Respiratory Therapeutics, Inc., et al. v. Perrigo Company, et al.*, Rule 26 Expert Report of John T. Goolkasian, Esq. (W.D. Mich. Aug. 4, 2009).

*Adams Respiratory Therapeutics, Inc., et al. v. Perrigo Company, et al.*, Expert Report of Michael Mayersohn, Ph.D. (W.D. Mich. Aug. 7, 2009).

*Adams Respiratory Therapeutics, Inc., et al. v. Perrigo Company, et al.*, Responsive Expert Report of Dr. Gordon Amidon—Redacted (W.D. Mich. Sep. 18, 2009).

*Adams Respiratory Therapeutics, Inc., et al. v. Perrigo Company, et al.*, Responsive Expert Report of Dr. Thomas S. Foster—Redacted (W.D. Mich. Sep. 18, 2009).

*Adams Respiratory Therapeutics, Inc., et al. v. Perrigo Company, et al.*, Expert Report of Charles E. Van Horn (W.D. Mich. Sep. 18, 2009).

*Adams Respiratory Therapeutics, Inc., et al. v. Perrigo Company, et al.*, Reply Expert Report of Walter G. Chambliss, Ph.D.—Redacted (W.D. Mich. Oct. 9, 2009).

*Adams Respiratory Therapeutics, Inc., et al. v. Perrigo Company, et al.*, Reply Expert Report of John T. Goolkasian, Esq. (W.D. Mich. Oct. 7, 2009).

*Adams Respiratory Therapeutics, Inc., et al. v. Perrigo Company, et al.*, Reply Expert Report of Michael Mayersohn, Ph.D.—Redacted (W.D. Mich. Oct. 8, 2009).

*Adams Respiratory Therapeutics, Inc., et al. v. Perrigo Company, et al.*, Supplemental Expert Report of Dr. Gordon Amidon—Redacted (W.D. Mich. Nov. 14, 2009).

*Adams Respiratory Therapeutics, Inc., et al. v. Perrigo Company, et al.*, Second Supplemental Expert Report of Dr. Gordon Amidon—Redacted (W.D. Mich. Nov. 15, 2009).

J.B. Aluri & S. Stavchansky, "Determination of Guaifenesin in Human Plasma by Liquid Chromatography in the Presence of Pseudoephedrine," J. of Pharm. & Biomed. Analysis 11(9):803-808 (1993) PGFSN 053048-053055.

Gordon L. Amidon et al., "Estimating Human Oral Fraction Dose Absorbed: A Correlation Using Rat Intestinal Membrane Permeability for Passive and Carrier-Mediated Compounds," Pharm, Research 5(10):651-654 (1988).

Gordon L. Amidon et al., "Effects of Gravity on Gastric Emptying, Intestinal Transit, and Drug Absorption," J. Clin. Pharmacol. 31:968-973 (1991).

Gordon L. Amidon et al., "A Theoretical Basis for a Biopharmaceutic Drug Classification: The Correlation of in Vitro Drug Product Dissolution and in Vivo Bioavailability." Pharm. Research 12(3):413-420 (1995).

Howard C. Ansel et al., Pharmaceutical Dosage Forms and Drug Delivery Systems 213-225 (6th ed. 1995).

Howard C. Ansel et al., Pharmaceutical Dosage Forms and Drug Delivery Systems 229-243 (7th ed. 1999).

A. Arancibia et al., "Pharmacokinetics and Bioavailability of a Controlled Release Amoxicillin Formulation," Int'l J. of Clin. Pharmacol., Therapy and Toxicology 25(2):97-100 (1987).

B. Huet De Barochez et al., "Influence of Drug Solubility in the Formulation of Hydrophilic Matrices," Drug Development and Industrial Pharmacy 15(14-16):2197-2212 (1989).

Joeby Bass et al., "An Evaluation of the Effect of Food on the Oral Bioavailability of Sustained-Release Morphine Sulfate Tablets (Oramorph Sr) After Multiple Doses," J. Clin. Pharmacol. 32(11):1003-1007 (1992).

Henning H. Blume & Barbara S. Schug, "The Biopharmaceutics Classification System (BCS): Class III Drugs—Better Candidates for BA/BE Waiver?" European J. Pharm. Sciences 9:117-121 (1999) PGFSN 054720-054726.

(56) References Cited

OTHER PUBLICATIONS

Rudolph H. Blythe, "The Formulation and Evaluation of Sustained Release Products," Drug Standards 26(1):1-7 (1958) PGFSN 053162-053170.
Gerald W. Bottenfield et al., "Safety and Tolerability of a New Formulation (90mg/kg/day Divided Every 12 h) of Amoxicillin/ Clavulanate (Augmentin®) in the Empiric Treatment of Pediatric Acute Otitis Media Caused by Drug- Resistant Streptococcus Pneumoniae," Pediatr. Infect. Dis. J. 17(10):963-968 (1998).
Harold G. Boxenbaum, "Physiological and Pharmacokinetic Factors Affecting Performance of Sustained Release Dosage Forms," Drug Dev. & Industrial Pharmacy 8(1):1-25 (1982).
David E. Bugay & W. Paul Findlay, Pharmaceutical Excipients 289 (1999).
Xianhua Cao et al., "Permeability Dominates in Vivo Intestinal Absorption of P-gp Substrate with High Solubility and High Permeability," Molecular Pharmaceutics 2(4):329-340 (2005).
Rong-Kun Chang & Joseph R. Robinson, "Sustained Drug Release from Tablets and Particles Through Coating," in Pharmaceutical Dosage Forms, vol. 3, pp. 199-302 (Herbert A. Lieberman et al. eds., 2d ed., revised and expanded, 1990).
Jun Chen et al., "Superporous Hydrogels as a Platform for Oral Controlled Drug Delivery," in Handbook of Pharmaceutical Controlled Release Technology 211-224 (Donald L. Wise et al. eds. 2000).
Charles S. L. Chiao & Joseph R. Robinson, "Sustained-Release Drug Delivery Systems," in Remington: The Science and Practice of Pharmacy 1660-1675 (Alfonso R. Gennaro ed., 19th ed. 1995).
Yie W. Chien, Novel Drug Delivery Systems 747-776 (2d ed., revised and expanded, 1992).
Ferenc Csizmadia et al., "Prediction of Distribution Coefficient from Structure. 1. Estimation Model," J. Pharm. Sciences 86(7):865-871 (1997).
S. S. Davis et al., "Transit of Pharmaceutical Dosage Forms Through the Small Intestine," Gut 27:886-892 (1986).
J.G. Devane et al., "Pharmacokinetic and In-Vitro Characteristics of Sustained Release Verapamil Products," Drug Development and Industrial Pharmacy 16(7):1233-1248 (1990).
John Devane, "Oral Drug Delivery Technology: Addressing the Solubility/Permeability Paradigm," Pharm. Tech. 22(11):68-80 (1998).
John G. Devane & John G. Kelly, "Effect of Food on the Bioavailability of a Multiparticulate Sustained-Release Verapamil Formulation," Advances in Therapy 8(1):48-53 (1991).
M. R. Dobrinska & P. G. Welling, "Blood Levels from a Sustained-Release Dosage Form," J. Pharm. Sciences 17(10):1728-1729 (1998).
J.B. Dressman et al., "Physicochemical Model for Dose-Dependent Drug Absorption," J. Pharm. Sciences 73(9):1274-1279 (1984).
J.B. Dressman et al., "Absorption Potential: Estimating the Fraction Absorbed for Orally Administered Compounds," J. Pharm. Sciences 74(5):588-589 (1985).
Natalie D. Eddington et al., "Development and Internal Validation of an In Vitro—In Vivo Correlation for a Hydrophilic Metoprolol Tartrate Extended Release Tablet Formulation," Pharm. Research 15(3):466-473 (1998).
M. El-Khawas et al., "Phenylpropanolamine Controlled-Release Tablets," Pharm. Ind. 55(4):392-395 (1993) PGFSN 052986-052991.
Mark G. Eller & Andrew A. Della-Coletta, "Absence of Effect of Food on Alprazolam Absorption from Sustained Release Tablets," Biopharmaceutics & Drug Disposition 11:31-37 (1990).
David Fleisher et al., "Drug, Meal and Formulation Interactions Influencing Drug Absorption After Oral Administration," Clin. Pharmacokinetics 36(3):233-254 (1999) PGFSN 05682-054705.
Arthur C. Guyton & John E. Hall, Textbook of Medical Physiology 793-802, 833-844 (9th ed. 1996).
Lester I. Harrison, "Kinetics of Absorption of a new Once-a-Day Formulation of Theophylline in the Presence and Absence of Food," J. Pharm. Sciences 82(6):644-648 (1993).
A.K. Hilton & P.B. Deasy, "In Vitro and In Vivo Evaluation of an Oral Sustained-Release Floating Dosage Form of Amoxycillin Trihydrate," Int'l J. Pharmaceutics 86:79-88 (1992).
A.K. Hilton & P.B. Deasy, "Use of Hyroxypropyl Methylcellulose Acetate Succinate in an Enteric Polymer Matrix to Design Controlled-Release Tablets of Amoxicillin Trihydrate," J. Pharm. Sciences 82(7):737-743 (1993).
J. Hirtz, "The Gastrointestinal Absorption of Drugs in Man: A Review of Current Concepts and Methods of Investigation," Br. J. Clin. Pharmac. 19:77S-83S (1985).
Ammon Hoffman et al., "Pharmacodynamic and Pharmacokinetic Rationales for the Development of an Oral Controlled-Release Amoxicillin Dosage Form," J. Controlled Release 54:29-37 (1998).
H. E. Huber et al., "Utilization of Hydrophilic Gums for the Control of Drug Release from Tablet Formulations I. Disintegration and Dissolution Behavior," J. Pharm. Sciences 55(9):974-976 (1966).
Physicians' Desk Reference to Pharmaceutical Specialties and Biologicals, 312, 313, 405, 406, 408, 412, 417, 420, 424, 427, 434, 559-561, 614, 673, 694, 713, 714, 746, 747, 838, 845, 846, 930, 955, 956, 982, 994, 1001, 1079, 1080, 1130, 1163, 1174, 1175, 1191, 1343, 1359, 1615, 1623, 1624, 1837, 1853, 1875, 1983, 1988, 1989, 1990, 1991, 1995-1999, 2079, 2219-2221, 2385, 2386 (46th ed. 1992) PGFSN 054207-054265.
Physicians' Desk Reference to Pharmaceutical Specialties and Biologicals, 303, 306, 308, 309, 319, 325, 328, 329, 337, 339, 402, 453-458, 462-467, 527, 581, 582, 668, 669, 782, 791, 792, 933, 934, 952-954, 958, 959, 990-992, 1004, 1013, 1283, 1284, 12585, 1319, 1320, 1336, 1337, 1358, 1359, 1363, 1542, 1543, 1785, 1787, 1788, 1981, 1982, 1986, 1987, 1988, 2010, 2011, 2038, 2039, 2041, 2051-2056, 2073, 2074, 2229, 2250, 2340, 2341, 2463, 2464, 2565, 2566, 2576, 2660, 2672, 2673, 2677, 2678, 2680-2683 (50th ed. 1996) PGFSN 054266-054360.
Physicians' Desk Reference to Pharmaceutical Specialties and Biologicals, 120, 303, 305, 308, 320, 323, 325, 338, 339, 402, 481, 514, 666, 672, 787, 808-810, 950, 970-973, 993, 1003, 1011, 1331, 1383, 1384, 1406, 1407, 1413, 1414, 2573, 2574, 1605, 1606, 1612, 1622-1625, 1631-1634, 2056, 2130, 2131, 2174, 2175, 2212, 2217, 2225-2229, 2248, 2249, 2349, 2375, 2472, 2612, 2813, 2750, 2751, 2765, 2768, 2779-2781, 2786, 2788, 2789 (51st ed. 1997) PGFSN 054361-054442.
Physicians' Desk Reference to Pharmaceutical Specialties and Biologicals, 701, 824, 883, 884-888, 895, 910, 911, 926, 940, 1249, 1292, 1348, 1350, 1369, 1382, 1383, 1552, 1560, 1567, 1576, 1577, 1578, 1780, 1786-1788, 1794, 1795, 1797, 1817, 2236, 2313, 2314, 2354, 2355, 2430, 2431, 2526, 2567, 2568, 2597, 2600, 2601, 2676, 2688, 2924 2925, 2926, 2952, 2965-2967, 2971, 2972, 2979, 2980, 2987, 2988, 3212 (52d ed. 1998) PGFSN 054443-054508.
Physicians' Desk Reference to Pharmaceutical Specialties and Biologicals, 116, 342, 739, 869, 870, 948-952, 960, 977, 978, 995, 996, 1014, 1358, 1474, 1475, 1488, 1489, 1509, 1510, 1688, 1695, 1696, 1698, 1699, 1707-1709, 1926, 1951, 1952, 1985, 2450, 2579, 2580, 2648, 2649, 2743, 2777, 2778, 2810, 2812, 2896, 2897, 3159, 3160, 3161, 3162, 3190, 3191, 3200, 3201, 3202, 3206, 3207, 3215, 3216, 3241, 3242, (53d ed. 1999) PGFSN 054509-054572.
Random House Unabridged Dictionary 1780 (2d ed. 1993).
Textbook of Therapeutics: Drug and Disease Management 1255 (Eric T. Herfindal & Dick R. Gourley eds., 6th ed. 1996) PGFSN 054880-054882.
The United States Pharmacopeia / The National Formulary 19-20, 724-725 (USP 23 / NF 18 1995) PGFSN 054594-054599.
Webster's New World/Stedman's Concise Medical Dictionary 345 (1987).
Wilson and Gisvold's Textbook of Organic Medicinal and Pharmaceutical Chemistry 948-956 (John H. Block & John M. Beale, Jr. eds., 11th ed. 2004) PGFSN 054738-054748.
The Dow Chemical Company, Formulating Sustained Release Pharmaceutical Products With Methocel (1982).
Thomson Reuters Press Release, "Thomson Healthcare Launches PDRhealth.com" pp. 1-3 (Nov. 5, 2007) (found at http://thomsonreuters.com/content/press_room/tsh/mdx_ThomHcareLaunchesPDRhealth on Mar. 31, 2010).
47 FR 30002-30010 (Jul. 9, 1982) PGFSN 053860-053880.

(56) References Cited

OTHER PUBLICATIONS

54 FR 8494-8509 (Feb. 28, 1989) ART 0489984-0489999 & PGFSN 053881-053916.

Food and Drug Administration, Compliance Program Guidance Manual, Program 7361.003, Chapter 61—OTC Drug Evaluation (May 2007).

Food and Drug Administration, Inspections, Compliance, Enforcement, and Criminal Investigations, CPG Sec. 450.200 Drugs—General Provisions and Administrative Procedures for Recognition as Safe and Effective (CPG 7132b.15) (found at fda.gov/ICECI/.../ucm074388.htm on Oct. 15, 2009).

U.S. Department of Health and Human Services, Food and Drug Administration, Center for Devices and Radiological Health, Guidance for Industry and FDA Staff, "Format for Traditional and Abbreviated 510(k)s" (Aug. 12, 2005).

U.S. Department of Health and Human Services, Food and Drug Administration, Center for Drug Evaluation and Research (CDER), Guidance for Industry, "Extended Release Oral Dosage Forms: Development, Evaluation, and Applications of In Vitro/In Vivo Correlations" (Sep. 1997).

U.S. Department of Health and Human Services, Food and Drug Administration, Center for Drug Evaluation and Research (CDER), Guidance for Industry, "SUPAC-MR: Modified Release Solid Oral Dosage Forms, Scale-Up and Postapproval Changes: Chemistry, Manufacturing, and Controls; In Vitro Dissolution Testing and In Vivo Bioequivalence Documentation" (Sep. 1997).

U.S. Department of Health and Human Services, Food and Drug Administration, Center for Drug Evaluation and Research (CDER), Guidance for Industry, "Waiver of In Vivo Bioavailability and Bioequivalence Studies for Immediate Release Solid Oral Dosage Forms Containing Certain Active Moieties/Active Ingredients Based on a Biopharmaceutics Classification System," Draft Guidance (Jan. 1999) PGFSN 054706-054719.

U.S. Department of Health and Human Services, Food and Drug Administration, Center for Drug Evaluation and Research (CDER), Guidance for Industry, "Statistical Approaches to Establishing Bioequivalence" (Jan. 2001).

U.S. Department of Health and Human Services, Food and Drug Administration, Center for Drug Evaluation and Research (CDER), Guidance for Industry, "Food-Effect Bioavailability and Fed Bioequivalence Studies" (Dec. 2002).

U.S. Department of Health and Human Services, Food and Drug Administration, Center for Drug Evaluation and Research (CDER), Guidance for Industry, "Power Blends and Finished Dosage Units—Stratified In-Process Dosage, Unit Sampling and Assessment," Draft Guidance (Oct. 2003).

U.S. Department of Health and Human Services, Food and Drug Administration, Center for Drug Evaluation and Research (CDER), Guidance for FDA Staff and Industry, "Marketed Unapproved Drugs—Compliance Policy Guide, Sec. 440.100 Marketed New Drugs Without Approved NDAs or ANDAs" (Jun. 2006).

Correspondence from David J. Horowitz, Esq., Director, Office of Compliance, Center for Drug Evaluation and Research, Food and Drug Administration to 45 entities, Guaifenesin single product Warning Letters (Oct. 11, 2002).

Correspondence from David J. Horowitz, Esq., Director, Office of Compliance, Center for Drug Evaluation and Research, Food and Drug Administration to 26 entities, Guaifenesin multiple products Warning Letters (Oct. 11, 2002).

Correspondence from Salomon Stavchansky Ph.D., Professor of Pharmaceutics and Alcon Centennial Professor of Pharmacy to R. Andrew Morgan, R.Ph., Adams Laboratories, Inc., Regulatory Affairs, including attachment (Feb. 1, 1994) ART 0447100-0447152.

STN Search Report 1-5 (Oct. 7, 2009).

Drituss G and Q-Bid La, Qualitest 011.

Q-Bid La labels, QUALITEST 015 & 017.

Drituss G and Q-Bid LA and labels, VINTAGE 011-018.

*Adams Respiratory Therapeutics, Inc., et al. v. Perrigo Company, et al.*, Plaintiffs' Opening Memorandum Of Law On Claim Construction (W.D. Mich. May 21, 2009).

*Adams Respiratory Therapeutics, Inc., et al. v. Perrigo Company, et al.*, Declaration Of Dr. Thomas Foster (W.D. Mich, May 21, 2009).

*Adams Respiratory Therapeutics, Inc., et al. v. Perrigo Company, et al.*, Defendants' Markman Brief In Support Of Their Proposed Claim Construction (W.D. Mich. May 21, 2009).

*Adams Respiratory Therapeutics, Inc., et al. v. Perrigo Company, et al.*, Declaration Of Walter G. Chambliss, Ph.D. (WV.D. Mich. May 20, 2009).

*Adams Respiratory Therapeutics, Inc., et al. v. Perrigo Company, et al.*, Plaintiffs' Responsive Memorandum Of Law On Claim Construction (W.D. Mich, Jun. 22, 2009).

*Adams Respiratory Therapeutics, Inc., et al. v. Perrigo Company, et al.*, Supplemental Declaration Of Dr. Thomas Foster (W.D. Mich. Jun. 22, 2009).

*Adams Respiratory Therapeutics, Inc., et al. v. Perrigo Company, et al.*, Defendants' Responsive Brief To Plaintiffs' Opening Memorandum Of Law On Claim Construction (W.D. Mich. Jun. 22, 2009).

*Adams Respiratory Therapeutics, Inc., et al. v. Perrigo Company, et al.*, Plaintiffs' Reply Memorandum Of Law On Claim Construction (W.D. Mich, Jul. 8, 2009).

*Adams Respiratory Therapeutics, Inc., et al. v. Perrigo Company, et al.*, Second Supplemental Declaration Of Dr. Thomas Foster (W.D. Mich. Jul. 8, 2009).

*Adams Respiratory Therapeutics, Inc., et al. v. Perrigo Company, et al.*, Defendants' Reply In Support Of Defendants' Markman Brief In Support Of Their Proposed Claim Construction (W.D. Mich. Jul. 8, 2009).

*Adams Respiratory Therapeutics, Inc., et al. v. Perrigo Company, et al.*, Supplemental Declaration Of Walter G. Chambliss, Ph.D. (W.D. Mich. Jul. 7, 2009).

*Adams Respiratory Therapeutics, Inc., et al. v. Perrigo Company, et al.*, Order and Proposed Construction of Disputed Terms (W.D. Mich. Jul. 24, 2009).

*Adams Respiratory Therapeutics, Inc., et al. v. Perrigo Company, et al.*, Submission In Response To The Court's Proposed Construction Of Disputed Terms (W.D. Mich. Aug. 7, 2009).

*Adams Respiratory Therapeutics, Inc., et al. v. Perrigo Company, et al.*, Defendants' Response To The Court's Jul. 24, 2009 Proposed Construction Of Disputed Terms (W.D. Mich. Aug. 7, 2009).

*Adams Respiratory Therapeutics, Inc., et al. v. Perrigo Company, et al.*, Order Adopting Proposed Claim Construction (W.D. Mich. Aug. 24, 2009).

*Adams Respiratory Therapeutics, Inc., et al. v. Perrigo Company, et al.*, Memorandum In Support Of Plaintiffs' Motion For Reconsideration Of Court's Aug. 24, 2009 Order Regarding Claim Construction Of The Term "Fully Bioavailable In The Subject's Stomach"—Redacted (W.D. Mich. Dec. 4, 2009).

*Adams Respiratory Therapeutics, Inc., et al. v. Perrigo Company, et al.*, Defendants' Opposition to Plaintiffs' Motion For Reconsideration Of The Court's Aug. 24, 2009 Order Construing The Term "Fully Bioavailable In The Subject's Stomach"—Redacted (W.D. Mich. Dec. 14, 2009).

*Adams Respiratory Therapeutics, Inc., et al. v. Perrigo Company, et al.*, Defendants' Memorandum In Support Of Their Motion For Summary Judgment Of Non-Infringement—Redacted (W.D. Mich. Nov. 16, 2009).

*Adams Respiratory Therapeutics, Inc., et al. v. Perrigo Company, et al.*, Plaintiffs' Memorandum Of Law In Opposition To Defendants' Motion For Summary Judgment Of Non-Infringement—Redacted (W.D. Mich. Dec. 14, 2009).

A. S. Hussain et al., "The Biopharmaceutics Classification System: Highlights of the FDA's Draft Guidance," Dissolution Technologies May 1999 Article #1, pp. 1-4 and Biopharmaceutics Classification Figures 1-3, pp. 1-2 (found at http://www.dissolutiontech.com/DTresour/599articles/Biopharm_Class2_copy.html and http://www.dissolutiontech.com/DTresour/599articles/BiopharmFig1-3.html on Oct. 15, 2009).

L. Kalantzi et al., "Biowaiver Monographs for Immediate Release Solid Oral Dosage Forms: Acetaminophen (Paracetamol)," J. Pharm. Sciences 95(1):4-14 (2006).

(56) References Cited

OTHER PUBLICATIONS

Lydia C. Kaus et al., "The Effect of In Vivo Dissolution, Gastric Emptying Rate, and Intestinal Transit Time on the Peak Concentration and Area-Under-the Curve of Drugs with Different Gastrointestinal Permeabilities," Pharm. Research 16(2):272-280 (1999).
Th. Knapp, "Der Einfluss von Guajakolderivaten auf die Ausscheidung der Glukuronsäure," J. Suisse de Chimie et Pharmacie LX(17):229-231, 245-248, 257-262 (1911), with certified translation.
Leszek Krowczynski, Extended-Release Dosage Forms 4-6, 51-58 (Dorota Porebska Brozyna trans. 1987).
C. Gordon Law, "Dose Proportionality," in Encyclopedia of Biopharmaceutical Statistics 295-297 (Shein-Chung Chow ed., 2d ed., revised and expanded, 2003).
Mark A. Longer & Joseph R. Robinson, "Sustained-Release Delivery Systems," in Remington's Pharmaceutical Sciences 1644-1661 (Alfonso R. Gennaro ed., 17th ed. 1985).
R. D. Maier, "Zum Nachweis von Guaiphenesin, einem Inhaltsstoff einiger Rezeptfreier Schlafmittel," Archives of Toxicology 45:123-131 (1980) PGFSN 054573-054583.
Carol N. Manners et al., "Distribution Coefficient, a Convenient Term for the Relation of Predictable Physico-Chemical Properties to Metabolic Processes," Xenobiotica 18(3):331-350 (1988) PGFSN 054769-054790.
Marilyn N. Martinez & Gordon L. Amidon, "A Mechanistic Approach to Understanding the Factors Affecting Drug Absorption: A Review of Fundamentals," J. Clin. Pharmacol. 42:620-643 (2002).
William R. Maynard, Jr. & Robert B. Bruce, "GLC Determination of Gualacol Glyceryl Ether in Blood," J. Pharm. Sciences 59(9):1346-1348 (1970) PGFSN 054808-054811.
Hussain Y. Mohammed & Frederick F. Cantwell, "Liquid Chromatographic Analysis of Pharmaceutical Syrups Using Pre-Columns and Salt-Adsorption on Amberlite XAD-2," Analytical Chemistry 50(3):491-496 (1978) PFGSN 054812-054817.
Sakae Obara et al. "Evaluation of Several Grades of Hydroxypropyl Methylcellulose for Use in a Sustained-Release Tablet Matrix," Advances in Pharmaceutics and Pharm. Tech., pp. 212-219 (1989).
Rebecca L. Oberle & Gordon L. Amidon, "The Influence of Variable Gastric Emptying and Intestinal Transit Rates on the Plasma Level Curve of Cimetidine; An Explanation for the Double Peak Phenomenon," J. Pharmacokinetics & Biopharmaceutics 15(5):529-544 (1987).
Eugene L. Parrott, "Solid Dosage Forms," in Prescription Pharmacy, Dosage Formulation and Pharmaceutical Adjuncts 103-162 (Joseph B. Sprowls, Jr. ed., 2d ed. 1970) PGFSN 053056-053116.
James E. Polli et al., "Summary Workshop Report: Biopharmaceutics Classification System-Implementation Challenges and Extension Opportunities," J. Pharm. Sciences 93(6):1375-1381 (2004).
W. Steven Pray, Nonprescription Product Therapeutics 225-231 (1999).
Gurvinder Singh Rekhi et al., "Identification of Critical Formulation and Processing Variables for Metoprolol Tartrate Extended-Release (ER) Matrix Tablets," J. Controlled Release 59:327-342 (1999).
Manford Robinson et al., "Sustained Action Dosage Forms," in The Theory and Practice of Industrial Pharmacy 439-465 (Leon Lachman et al. eds., 2d ed. 1976) PGFSN 053001-053029.
P. E. Rolan, "The Assessment of Pharmacokinetics in Early Phase Drug Evaluation," in Handbook of Phase I/II Clinical Drug Trials 169-175 (John O'Grady & Pieter H. Joubert eds. 1997).
Earl Rosen & Joseph V. Swintosky, "Preparation of a 35S Labelled Trimeprazine Tartrate Sustained Action Product for Its Evaluation in Man," J. of Pharmacy and Pharmacology, XII Supp.:237T-244T (1960) PGFSN 052992-053000.
Edward M. Rudnic & Mary Kathryn Kottke, "Tablet Dosage Forms," in Modern Pharmaceutics 333, 359-364 (Gilbert S. Banker & Christopher T. Rhodes eds., 3d ed., revised and expanded, 1996).
H. Rupprecht & D. Regensburg, "XIV. Silicium Dioxide and Silicates in Drug Delivery," in Controlled Drug Delivery 197-225 (Bernd W. Müller ed. 1987).

Leroy A. Shervington & Amal Shervington, "Guaifenesin," in Analytical Profiles of Drug Substances and Excipients 121-164 (Harry G. Brittain ed. 1998) PGFSN 054626-054671.
Patrick J. Sinko & Gordon L. Amidon,"Characterization of the Oral Absorption of B-Lactam Antibiotics. I. Cephalosporins: Determination of Intrinsic Membrane Absorption Parameters in the Rat Intestine In Situ," Pharm. Research 5(10) 645-650 (1988).
J. P. Skelly et al., "Scaleup of Oral Extended-Release Dosage Forms," Pharm. Research 10(12):1800-1805 (1993).
Dennis Smith et al., "Design of Drugs Involving the Concepts and Theories of Drug Metabolism and Pharmacokinetics," Medicinal Research Reviews 16(3):243-266 (1996) PGFSN 054600-054625.
Dennis Smith, "Can We Design Drugs with Low Variability," in Variability in Human Drug Response 251-261 (G.T. Tucker ed. 1999) PGFSN 054727-054737.
Dennis Smith & Barry Jones, "Variability in Drug Response as a Factor in Drug Design," Current Opinion in Drug Discovery & Development 2(1):33-41 (1999) PGFSN 054672-054681.
Joel T. Smith & Dutt V. Vinjamoori, "Rapid Determination of Logarithmic Partition Coefficients Between n-Octanol and Water Using Micellar Electrokinetic Capillary Chromatography," J. Chromatography B: Biomed. Applications 669(1):59-66 (1995) PGFSN 054759-054768.
David O. Thueson, Thueson's Guide to Over-The-Counter Drugs 54-57 (1995).
Klara Valkó et al., "Chromatographic Hydrophobicity Index by Fast-Gradient RP-HPLC: A High-Throughput Alternative to log P/log D," Anal. Chem. 69:2022-2029 (1997).
Daniel L. Wagner & Vikram S. Patel, "Steady-State Human Pharmacokinetics and Bioavailability of Guaifenesin and Pseudoephedrine in a Sustained-Release Tablet Relative to Immediate-Release Liquids," Int'l J. Pharmaceutics 114:171-176 (1995) PGFSN 053117-053122 pris.
Zheng Wang et al., "In-Vivo and In-Vitro Evaluations of a Modified-Release Oral Dosage Form of Nifedipine by Hybridization of Hydroxypropyl-β-Cyclodextrin and Hydroxypropylcelluloses in Dogs," J. Pharm. Pharmacol. 46:505-507 (1994) PGFSN 052869-52871.
Hong Gi Yi et al., "Formulation of a Extended Release Tablet Containing Dexibuprofen," Arch. Pharm. Res. 31(12):1637-1643 (2008).
Lawrence X. Yu & Gordon L. Amidon, "A Compartmental Absorption and Transit Model for Estimating Oral Drug Absorption," Int'l J. Pharmaceutics 186:119-125 (1999).
Excipients and Delivery Systems for Pharmaceutical Formulations 123-124, 186-190 (D. R. Karsa & R. A. Stephenson eds. 1995).
Handbook of Pharmaceutical Excipients 252-261, 280-282, 424-427 (Ainley Wade & Paul J. Weller eds., 2d ed. 1994).
Handbook of Pharmaceutical Excipients 188-191 (Raymond C. Rowe et al. eds., 5th ed. 2006).
The Merck Index 716-717 (Susan Budavari et al. eds., 11th ed. 1989) PGFSN 054754-054758.
The Merck Index 776-777 (Susan Budavari et al. eds., 12th ed. 1996) PGFSN 054749-054753.
Pharmaceutical Dosage Forms, vol. 1, pp. 2, 241, 247-284 (Herbert A. Lieberman et al. eds., 2d ed., revised and expanded, 1989).
Pharmaceutical Dosage Forms, vol. 2, pp. 7-11, 13-20, 60-67 (Herbert A. Lieberman et al. eds., 2d ed., revised and expanded, 1990).
Physicians' Desk Reference to Pharmaceutical Specialties and Biologicals 216, 490-491 (5th ed. 1951) PGFSN 053917-053921.
Physicians' Desk Reference to Pharmaceutical Specialties and Biologicals 248, 517, 522, 570 (9th ed. 1955) PGFSN 053922-053927.
Physicians' Desk Reference to Pharmaceutical Specialties and Biologicals, 259, 636, 661, 687, 785, 787, 803, 805, 844, 846, 847, 869 (14th ed. 1960) PGFSN 053928-053941.
Physicians' Desk Reference to Pharmaceutical Specialties and Biologicals, 312, 313, 588, 614, 631, 632, 669, 682-686, 689, 749, 759, 760, 875, 877, 907-909, 955, 979, 1055, 1056, 1060, 1086-1088, 1097, 1149, 1161, 1212-1214, 1438, 1455, 1463, 1467, 1472, (25th ed. 1971) PGFSN 053942-053983.
Physicians' Desk Reference to Pharmaceutical Specialties and Biologicals, 313, 314, 563, 564, 576, 639, 647, 679, 685, 741, 742,

(56) References Cited

OTHER PUBLICATIONS 778, 779, 812, 815, 843-845, 850, 851, 856, 857, 862, 892, 893, 921, 922, 931, 957, 961, 1002, 1004, 1098, 1127-1129, 1131, 1283, 1343, 1356, 1390, 1405, 1419, 1421, 1422, 1443, 1444, 1517, 1533, 1542, 1568, 1581, 1735, 1736, 1794, 1795, 1797, 1808, 1821 (34th ed. 1980) PGFSN 053984-054044.
Physicians' Desk Reference to Pharmaceutical Specialties and Biologicals, 314, 406, 413, 420-423, 428, 432, 433, 442, 693-695, 702, 706, 739, 740, 836, 839, 886, 887, 909, 911, 912, 920, 921, 929, 948, 973, 974, 1001, 1024, 1025, 1058, 1059, 1072, 1182, 1233, 1234, 1235, 1236, 1378, 1379, 1394, 1395, 1421, 1431, 1432, 1445, 1486, 1570, 1589 1607, 1619, 1620, 1638-1640, 1645, 1664, 1685, 1749, 1750, 1759-1761, 1788, 1796-1798, 1824, 1828-1831, 1868, 1897, 2092, 2147, 2161, 2193, 2194 (39th ed. 1985) PGFSN 054045-054130.
Physicians' Desk Reference to Pharmaceutical Specialties and Biologicals, 311, 405, 411, 412, 416, 417, 419, 422, 426, 433, 556, 557, 662, 663, 670, 671, 674, 688, 702, 703, 784, 786, 829, 847, 849, 850, 856, 665, 880, 928, 948, 977, 990-993, 1074, 1111-1113, 1245, 1246, 1268, 1278, 1277, 1278, 1320, 1404, 1430-1432, 1447-1449, 1453, 1468, 1536, 1537, 1547, 1548, 1569, 1577, 1578, 1603, 1604, 1606, 1609, 1662, 1825, 1869, 1879, 1880, 1904, 1905, (40th ed. 1986) PGFSN 054131-054206.
*Reckitt Benckiser LLC v. Amneal Pharmaceuticals LLC, et al.*, Plaintiff Reckitt Benckiser's Responsive Markman Brief (D.N.J. Feb. 23, 2017).
*Reckitt Benckiser LLC v. Amneal Pharmaceuticals LLC, et al.*, Order Adopting Claim Construction (D.N.J. Mar. 30, 2017).
*Reckitt Benckiser LLC v. Dr. Reddy's Laboratories, Ltd., et al.*, *Reckitt Benckiser LLC v. Amneal Pharmaceuticals LLC, et al.*, Final Judgment (D.N.J. Aug. 22, 2017).
*Reckitt Benckiser LLC v. Amneal Pharmaceuticals LLC, Dr. Reddy's Laboratories, Inc.*, Dr. Reddy's Laboratories, Ltd., Non-Confidential Brief for Plaintiff (Fed. Cir. Dec. 20, 2017).
*Reckitt Benckiser LLC v. Amneal Pharmaceuticals LLC, Dr. Reddy's Laboratories, Inc.*, Dr. Reddy's Laboratories, Ltd., Brief for Defendants (Fed. Cir. Feb. 15, 2018).
*Reckitt Benckiser LLC v. Amneal Pharmaceuticals LLC, Dr. Reddy's Laboratories, Inc.*, Dr. Reddy's Laboratories, Ltd., Reply Brief for Plaintiff (Fed. Cir. Mar. 22, 2018).
*Reckitt Benckiser LLC v. Amneal Pharmaceuticals LLC, Dr. Reddy's Laboratories, Inc.*, Dr. Reddy's Laboratories, Ltd., Appeal Judgment (Fed. Cir. Sep. 10, 2018).
*Reckitt Benckiser LLC v. Dr. Reddy's Laboratories, Ltd., et al.*, *Reckitt Benckiser LLC v. Amneal Pharmaceuticals LLC, et al.*, Public Opinion (D.N.J. Sep. 10, 2018).
*Reckitt Benckiser LLC v. Amneal Pharmaceuticals LLC*, Opinion (D.N.J. Oct. 25, 2019).
21 C.F.R. 341 Cold, cough, allergy, bronchodilator and antiasthmatic drug products for over-the—counter human use, Fed. Reg. Vol. 54, No. 38 (1989).
Ansel, Howard C., "Introduction to Pharmaceutical Dosage Forms," Chapter 4 (8th ed. 1985).
Bodmeier, R., et al., "Prolonged release multiple unit dosage forms based on water soluble cellulosic polymers or aqueous latexes, Proceedings 18th International Symposium on controlled Release of Bioactive Materials" (1991).
Bodmeier, Roland et al., "Microencapsulation of drugs with aqueous colloidal polymer," J. Pharm. Sci., vol. 82, No. 2, 191-194 (1993).
Brock, Michael H. et al., "Use of In Vitro and In Vivo Data in the Design, Development, and Quality Control of Sustained-Release Decongestant Dosage Forms," 14 (4) 430-437 (1994).
Chai, Chih-Kun Pauline, "Determination of dextrorphan and gualfenesin by high performance liquid chromatography—pharmacokinetics of guaifenesin" (1994).
Davis, S. S. et al., "Transit of pharmaceutical dosage forms through the small intestine," http://gut.bmj.com/ (Aug. 22, 2016).
Dr. Crooks Second Declaration ('252 Re-Exam) (Aug. 21, 2006).

European Search Report issued in European Patent Application No. 16 785 649.1, dated Apr. 30, 2019.
FDA approved labeling for Mucinex® at ART0009679-86 (Jul. 12, 2002).
Ford, James L., "Design and Evaluation of Hydroxypropyl Methylcellulose Matrix Tablets for Oral Controlled Release: A Historical Perspective," American Association of Pharmaceutical Scientists, p. 17-51 (2014).
Gennaro, Alfonso R., "Remington: The Science and Practice of Pharmacy," 20th Ed. Ch. 53.
Gennaro, Alfonso R., "Remington: The Science and Practice of Pharmacy," Ch. 10, 36, 91 (18th ed., 1990).
Guaifenesin, Drug Bank https://www.drugbank.ca/drugs/DB00874 (Mar. 16, 2017).
Gudipati, Manga Raju, "In vitro/in vivo correlation approach for the development of drug delivery systems," (1990).
Haan, P. De, et al., "Oral Controlled Release Dosage Forms. A review," Pharmaceutisch Weekblad Scientific Edition, vol. 6 (1984).
Huber, et al., Journal of Pharmaceutical Sciences vol. 55, pp. 974-997 (1966).
Kim, C., "Controlled Release Dosage Form Design," Technomic Publishing Co.,Inc. (2000).
Klancar, Uros et al., "Determining the Polymer Threshold Amount for Achieving Robust Drug Release from HPMC and HPC Matrix Tablets Containing a High-Dose BCS Class I Model Drug: In Vitro and In Vivo Studies," American Association of Pharmaceutical Scientists (2015).
Lee, Peter I.D., et al., "Pharmacokinetic Analysis" Ch. 8 (1996).
Lipinski, Christopher A. et al., "Experimental and computational approaches to estimate solubility and permeability in drug discovery and development settings," Advanced Drug Delivery Reviews 46 3-26 (2001).
Melegari, Cecilia et al., "Ethylcellulose film coating of guaifenesin-loaded pellets: A comprehensive evaluation of the manufacturing process to prevent drug migration," European Journal of Pharmaceutics and Biopharmaceutics 100 15-26 (2016).
Pade, Vaishali, et al., "Bioavailability of pseudoephedrine from controlled release formulation in the presence of guaifensin in human volunteers, Biopharmaceutics & Drug Disposition," vol. 16, 381-391 (1995).
Physicians' Desk Reference to Pharmaceutical Specialties and Biologicals 3202 (53rd ed. 1999).
Sharmin, Nahid et al., "A Novel Method to Study the Effect of pH and Excipients on Water Uptake and Swelling Behaviour of Carbopol Polymers," Bangladesh Pharmaceutical Journal vol. 13, No. 2 (Jul. 2010).
The Merck Index, 13th ed. (2001), at p. 812, Appendix C of 252 Reexam, Aug. 21, 2006 Amendment.
Thompson, Gary A. et al., "Guaifensin Pharmacokinetics Following Single-Dose Oral Administration in Children Aged 2 to 17 Years," The Journal of Clinical Pharmacology 56(7) 894-901 (2016).
U.S. Department of Health and Human Services, Food and Drug Administration, Center for Drug Evaluation and Research (CDER), Guidance for Industry, "Bioavailability and Bioequivalence Studies for Orally Administered Drug Products—General Considerations" (Mar. 2003). (26 pages).
U.S. Department of Health and Human Services, Food and Drug Administration, Center for Drug Evaluation and Research (CDER), Guidance for Industry, "Bioavailability and Bioequivalence Studies Submitted in NDAs or INDs—General Considerations," (Mar. 2014). Draft; 29 pages.
Velasco, M. Victoria et al., "Influence of drug: hydroxypropylmethylcellulose ratio, drug and polymer particle size and compression force on the release of diclofenac sodium from HPMC tablets," Journal of Controlled Release 57 75-85 (1999).
*Reckitt Benckiser LLC v. Aurobindo Pharma Limited et al.*, Complaint (D. Del. Sep. 17, 2014).
*Reckitt Benckiser LLC v. Aurobindo Pharma Limited et al.*, Answer, Defenses and Counterclaims of Aurobindo Pharma Limited and Aurobindo Pharma USA, Inc. (D. Del. Nov. 17, 2014).
*Reckitt Benckiser LLC v. Aurobindo Pharma Limited et al.*, Reckitt Benckiser's Reply to Aurobindo Pharma Limited and Aurobindo Pharma USA, Inc.'s Counterclaims (D. Del. Dec. 11, 2014).

(56) References Cited

OTHER PUBLICATIONS

*Reckitt Benckiser LLC v. Aurobindo Pharma Limited et al.*, Plaintiff Reckitt Benckiser's Opening Claim Construction Brief (D. Del. Mar. 4, 2016).
*Reckitt Benckiser LLC v. Aurobindo Pharma Limited et al.*, Aurobindo Pharma Limited and Aurobindo Pharma USA, Inc.'s Opening Claim Construction Brief (D. Del. Mar. 10, 2016).
International Search Report issued in International Application No. PCT/US2016/056481, dated Nov. 29, 2016 (14 pages).
"Empty Capsule Size Chart," https://www.capsuline.com/empty-capsule-size-chart/ (retrieved Nov. 17, 2016).
Barbara G. Wells et al., Pharmacotherapy Handbook, 691-692 (8th ed. 2012).
"Package Insert Emplate for Guaifenesin, Tablet/Capsule/Syrup", http://npra.moh.gov.my/images/reg-and-noti-/PI/non-poison/GuaiphenesinFINAL.pdf, (2013).
Angiolillo et al., "Clinical Pharmacology and Cardiovascular Safety of Naproxen." Am. J. Cardiovasc. Drug, 17, pp. 97-107 (2017).
Mura et al., "Thermal Behavior and Dissolution Properties of Naproxen from Binary and Ternary Solid Dispersions." Drug Dev. Ind. Pharm., 25(3), 257-264 (1999).
*Adams Respiratory Therapeutics, Inc., et al. v. Perrigo Company, et al.*, Defendants' Reply Memorandum In Support Of Their Motion For Summary Judgment Of Non-Infringement (W.D. Mich. Dec. 28, 2009).
*Adams Respiratory Therapeutics, Inc., et al. v. Perrigo Company, et al.*, Opinion [regarding Plaintiffs' motion for reconsideration and Defendants' motion for summary judgment] (W.D. Mich. Feb. 11, 2010).
*Adams Respiratory Therapeutics, Inc., et al. v. Perrigo Company, et al.*, Order Reconsidering And Vacating In Part Opinion And Order Regarding Claim Construction (W.D. Mich. Mar. 3, 2010).
*Adams Respiratory Therapeutics, Inc., et al. v. Perrigo Company, et al.*, Non-Confidential Brief Of Plaintiffs-Appellants Adams Respiratory Therapeutics, Inc., Adams Respiratory Operations, Inc., And Adams Respiratory Products, Inc. (Fed. Cir. Mar. 24, 2010).
*Adams Respiratory Therapeutics, Inc., et al. v. Perrigo Company, et al.*, NonConfidential Brief For Defendants- Appellees (Fed. Cir. Apr. 23, 2010).
*Adams Respiratory Therapeutics, Inc., et al. v. Perrigo Company, et al.*, Non-Confidential Reply Brief Of Plaintiffs-Appellants (Fed. Cir. May 3, 2010).
*Adams Respiratory Therapeutics, Inc., et al. v. Perrigo Company, et al.*, Opinion (Fed. Cir. Aug. 5, 2010).
Drituss G and Q-Bid La, Qualitest 011, produced by Perrigo Company et al. in the *Adams Respiratory Therapeutics, Inc. et al. v. Perrigo Company et al.* (W.D. Mich.) litigation in Aug. 2008.
Drituss G and Q-Bid La, Vintage 011, produced by Perrigo Company et al. in the *Adams Respiratory Therapeutics, Inc. et al. v. Perrigo Company et al.* (W.D. Mich.) litigation in Aug. 2008.
Drituss G label, VINTAGE 012, Dec. 2001.
Drituss G label, VINTAGE 013, Dec. 2001.
Guaifenesin Long-Acting Tablets, VINTAGE 014, Dec. 2001.
Guaifenesin Sustained-Release Tablets And Guaifenesin/Dextromethorphan Hydrobromide Sustained-Release Tablets, VINTAGE 018, Mar. 2001.
Q-BID LA label, QUALITEST 015, Apr. 1994,.
Q-BID LA label, QUALITEST 017, May 1999.
Q-BID LA label, VINTAGE 015, Apr. 1994.
Q-BID LA label, VINTAGE 016, Feb. 1999.
Q-BID LA label, VINTAGE 017, May 1999.
*Reckitt Benckiser Inc. v. Watson Laboratories, Inc.*—Florida & Watson Pharmaceuticals, Inc., Amended Complaint For Patent Infringement (S.D. Fla, Oct. 23, 2009).
*Reckitt Benckiser Inc. v. Watson Laboratories, Inc*—Florida & Watson Pharmaceuticals, Inc., Defendants Watson Laboratories, Inc.—Florida And Watson Pharmaceuticals, Inc.'s Answer And Counterclaims To Plaintiff's Amended Complaint (S.D. Fla. Oct. 29, 2009).

*Reckitt Benckiser Inc. v. Watson Laboratories, Inc*—Florida & Watson Pharmaceuticals, Inc., Reckitt Benckiser's Answer To Watson Laboratories, Inc.—Florida And Watson Pharmaceuticals, Inc.'s Oct. 29, 2009 Counterclaims (S.D. Fla. Nov. 23, 2009).
Physicians' Desk Reference: For Nonprescription Drugs and Dietary Supplements 807 (Medical Economics Company, Inc., 20th ed. 1999).
Bauer et al., "Coated Pharmaceutical Dosage Forms," p. 83 (MedPharm Scientific Publishers 1998).
Request for Reexamination, filed Apr. 20, 2005, U.S. Pat. No. 6,372,252, Issued Apr. 16, 2002.
Welling, P.G., "Oral Controlled Drug Administration: Pharmacokinetic Considerations," Drug Dev. Ind. Pharm., 9, 1185-1225 (1983).
International Search Report dated Aug. 19, 2003 for International Application No. PCT/US03/11500, filed Apr. 15, 2003.
Bodmeier, R. et al., "Prolonged Release Multiple-Unit Dosage Forms Based On Water-Soluble Cellulosic Polymers or Aqueous Latexes," Proceed. Intern. Sump. Control. Rel. Bioact. Mater., 18 (1991), Controlled Release Society, Inc.
Lacy et al. Drug Information Handbook p. 481 (1999).
Ansel HC and Popovich NG, Pharmaceutical Dosage Forms and Drug Delivery Systems, Lea & Febiger, p. 64 (5th ed. 1990).
Bankser GS and Rhodes CT, Modern Pharmaceutics, Marcel Dekker, Inc., p. 83 (4th ed. 2002).
United Research Laboratories and Mutual Pharmaceutical Company, Press Release: United Research Laboratories/Mutual Pharmaceutical Company Announce ANDA Filing For Guaifenesin Extended-Release Tablets, 600 mg And 1200 mg (Aug. 18, 2006).
Correspondence from E. Brendan Magrab, Esq., Vice President, Intellectual Property, United Research Laboratories, Inc. and Mutual Pharmaceutical Company, Inc. to Michael J. Valentino, President & Chief Executive Officer, Adams Respiratory Therapeutics, Inc., including Exhibits A and B and additional attachments (Aug. 22, 2006).
United Research Laboratories and Mutual Pharmaceutical Company, Press Release: United Research Laboratories/Mutual Pharmaceutical Company Formally Notifies Adams Respiratory Therapeutics Of Its ANDA Filing For Guaifenesin Extended-Release Tablets, 600 mg And 1200 mg (Aug. 23, 2006).
Correspondence from Joseph M. O'Malley, Jr., Esq., Attorney, Fitzpatrick, Cella, Harper & Scinto to E. Brendan Magrab, Esq., Vice President, Intellectual Property, United Research Laboratories, Inc. and Mutual Pharmaceutical Company, Inc., including attachment (Aug. 31, 2006).
Correspondence from James D. Veltrop, Attorney, Axinn, Veltrop & Harkrider LLP to Joseph M. O'Malley, Jr., Esq., Attorney, Fitzpatrick, Cella, Harper & Scinto, including attachment (Sep. 6, 2006).
United Research Laboratories and Mutual Pharmaceutical Company, Press Release: United Research Laboratories/Mutual Pharmaceutical Company Views Legal Response From Adams As Excessive And Disengenuous [sic] Attempt To Delay Competition (Sep. 7, 2006).
Correspondence from James D. Veltrop, Attorney, Axinn, Veltrop & Harkrider LLP to Dominick A. Conde, Attorney, Fitzpatrick, Cella, Harper & Scinto (Sep. 28, 2006).
Declaration of Harry G. Brittain, Ph.D. (Sep. 28, 2006), available at http://www.urlmutual.com/guaifenesin7.pdf.
United Research Laboratories and Mutual Pharmaceutical Company, Press Release: Independent Expert Confirms View That Adams Has No. Legal Basis For Pursuing Legal Action Against Mutual Pharmaceutical Company For Its Guaifenesin Extended Release Tablets, 600 mg And 1200 mg (Sep. 28, 2006).
*Adams Respiratory Therapeutics, Inc. v. Pharmaceutical Holdings Corp.*, Complaint for Patent Infringement and Certification Pursuant to Local Rule 11.2, including Exhibit A (D.N.J. Oct. 2, 2006).
*Adams Respiratory Therapeutics, Inc. v. Pharmaceutical Holdings Corp.*, Complaint for Patent Infringement, including Exhibit A (E.D. Pa. Oct. 4, 2006).
*Adams Respiratory Therapeutics, Inc. v. Pharmaceutical Holdings Corp.*, Answer and Counterclaims (E.D. Pa. Oct. 10, 2006).
*Adams Respiratory Therapeutics, Inc. v. Pharmaceutical Holdings Corp.*, Defendants' Motion for Summary Judgment (E.D. Pa. Oct. 17, 2006).

(56) References Cited

OTHER PUBLICATIONS

*Adams Respiratory Therapeutics, Inc.* v. *Pharmaceutical Holdings Corp.,* Defendants' Memorandum of Law in Support of a Motion for Summary Judgment (E.D. Pa. Oct. 17, 2006).
United Research Laboratories and Mutual Pharmaceutical Company, Press Release: Mutual Pharmaceutical Company Files Counter Suit Against Adams Respiratory Therapeutics (Oct. 17, 2006).
U.S. Department of Health and Human Services, Approved Drug Products with Therapeutic Equivalence Evaluations, pp. ix-x (19th ed. 1999).
*Reckitt Benckiser LLC* v. *Aurobindo Pharma Limited et al.,* Aurobindo Pharma Limited and Aurobindo Pharma USA, Inc.'s Responsive Claim Construction Brief (D. Del. Mar. 29, 2016).
*Reckitt Benckiser LLC* v. *Aurobindo Pharma Limited et al.,* Declaration of Michael F. Nullet (D. Del. Mar. 29, 2016).
*Reckitt Benckiser LLC* v. *Aurobindo Pharma Limited et al.,* Plaintiff Reckitt Benckiser's Responsive Claim Construction Brief (D. Del. Mar. 29, 2016).
*Reckitt Benckiser LLC* v. *Aurobindo Pharma Limited et al.,* Order for Partial Dismissal of Claims (D. Del. Aug. 24, 2016).
*Reckitt Benckiser LLC* v. *Aurobindo Pharma Limited et al.,* Memorandum Opinion (D. Del. Nov. 3, 2016).
*Reckitt Benckiser LLC* v. *Aurobindo Pharma Limited et al.,* Order (D. Del. Nov. 3, 2016).
*Reckitt Benckiser LLC* v. *Aurobindo Pharma Limited et al.,* Oral Order (D. Del. Dec. 21, 2016).
*Reckitt Benckiser LLC* v. *Aurobindo Pharma Limited et al.,* Aurobindo Pharma Limited and Aurobindo Pharma USA, Inc.'s Brief in Support of its Motion for Summary Judgment (D. Del. Dec. 29, 2016).
*Reckitt Benckiser LLC* v. *Aurobindo Pharma Limited et al.,* Plaintiff Reckitt Benckiser LLC's Answering Brief in Opposition to Defendants' Motion for Summary Judgment (D. Del. Jan. 24, 2017).
*Reckitt Benckiser LLC* v. *Aurobindo Pharma Limited et al.,* Aurobindo Pharma Limited and Aurobindo Pharma USA, Inc.'s Reply in Support of its Motion for Summary Judgment ( (D. Del. Jan. 31, 2017).
*Reckitt Benckiser LLC* v. *Aurobindo Pharma Limited et al.,* Memorandum Opinion (D. Del. Mar. 6, 2017).
*Reckitt Benckiser LLC* v. *Aurobindo Pharma Limited et al.,* Order (D. Del. Mar. 6, 2017).
*Reckitt Benckiser LLC* v. *Aurobindo Pharma Limited et al.,* Final Judgment Order (D. Del. Mar. 13, 2017).
European Examination Report issued Jul. 19, 2019, in counterpart application EP 15791011.8 (3 pages).
*Adams Respiratory Therapeutics, Inc., et al.* v. *Perrigo Company, et al.,* Docket Entries (W.D. Mich.).
*Adams Respiratory Therapeutics, Inc., et al.* v. *Perrigo Company, et al.,* Opinion (W.D. Mich. Jan. 11, 2012).
*Reckitt Benckiser Inc.* v. *Watson Laboratories, Inc.*—Florida & Watson Pharmaceuticals, Inc., Docket Entries (S.D. Fla.).
*Reckitt Benckiser Inc.* v. *Watson Laboratories, Inc.*—Florida & Watson Pharmaceuticals, Inc., Plaintiff Reckitt's Responses to Defendant Watson Laboratories, Inc.—Florida's First Set of Interrogatories (Nos. 1-4) (S.D. Fla. Oct. 19, 2009).
*Reckitt Benckiser Inc.* v. *Watson Laboratories, Inc.*—Florida & Watson Pharmaceuticals, Inc., Plaintiff Reckitt's Supplemental Responses to Defendant Watson Laboratories, Inc.—Florida's First Set of Interrogatories (Nos. 1-4) (S. D. Fla. May 19, 2010).
*Reckitt Benckiser Inc.* v. *Watson Laboratories, Inc.*—Florida & Watson Pharmaceuticals, Inc., Defendant Watson Laboratories, Inc.— Florida's Declaration of Gilbert S. Banker in Support of Watson Florida's Claim Construction Brief (S.D. Fla. Sep. 10, 2010).
*Reckitt Benckiser Inc.* v. *Watson Laboratories, Inc.*—Florida & Watson Pharmaceuticals, Inc., Defendant Watson Laboratories, Inc.— Florida's Claim Construction Brief (S.D. Fla. Sep. 10, 2010).
*Reckitt Benckiser Inc.* v. *Watson Laboratories, Inc.*—Florida & Watson Pharmaceuticals, Inc., Defendant Watson Laboratories, Inc.—

Florida's Declaration of Thomas Dowling in Support of Defendant Watson Florida's Claim Construction Brief (S.D. Fla. Sep. 10, 2010).
*Reckitt Benckiser Inc.* v. *Watson Laboratories, Inc.*—Florida & Watson Pharmaceuticals, Inc., Supplemental Declaration Of Dr. Thomas Foster (S.D. Fla. Sep. 24, 2010).
*Reckitt Benckiser Inc.* v. *Watson Laboratories, Inc.*—Florida & Watson Pharmaceuticals, Inc., Declaration Of Dr. Gordon Amidon (S.D. Fla. Sep. 24, 2010).
*Reckitt Benckiser Inc.* v. *Watson Laboratories, Inc.*—Florida & Watson Pharmaceuticals, Inc., Defendant Watson Laboratories, Inc.— Florida's Supplemental Declaration of Thomas Dowling in Support of Defendant Watson Florida's Reply in Support of Claim Construction Brief (S.D. Fla. Oct. 1, 2010).
*Reckitt Benckiser Inc.* v. *Watson Laboratories, Inc.*—Florida & Watson Pharmaceuticals, Inc., Defendant Watson Laboratories, Inc.— Florida's Reply in Support of Claim Construction Brief (S.D. Fla. Oct. 1, 2010).
*Reckitt Benckiser Inc.* v. *Watson Laboratories, Inc.*—Florida & Watson Pharmaceuticals, Inc., Reckitt's Memorandum In Support Of Its Motion For Summary Judgment Of No. Inequitable Conduct— Redacted (S.D. Fla. Nov. 12, 2010).
*Reckitt Benckiser Inc.* v. *Watson Laboratories, Inc.*—Florida & Watson Pharmaceuticals, Inc., Watson Laboratories, Inc.—Florida's Motion For Summary Judgment Of Non-Infringement and Supporting Memorandum of Law (S.D. Fla. Nov. 12, 2010).
*Reckitt Benckiser Inc.* v. *Watson Laboratories, Inc.*—Florida & Watson Pharmaceuticals, Inc., Order Approving Notices of Withdrawal; Withdrawing Motions (S.D. Fla. Dec. 6, 2010).
*Reckitt Benckiser Inc.* v. *Watson Laboratories, Inc.*—Florida & Watson Pharmaceuticals, Inc., Claim Construction Order (S.D. Fla. Jan. 12, 2011).
*Reckitt Benckiser Inc.* v. *Watson Laboratories, Inc.*—Florida & Watson Pharmaceuticals, Inc., Final Judgment For Defendant (S.D. Fla. Feb. 9, 2011).
*Reckitt Benckiser Inc.* v. *Watson Laboratories, Inc.*—Florida & Watson Pharmaceuticals, Inc., Watson Laboratories, Inc.—Florida of Proposed Redacted Findings of Fact and Conclusions of Law (S.D. Fla. Feb. 16, 2011).
*Reckitt Benckiser Inc.* v. *Watson Laboratories, Inc.*—Opinion (Fed. Cir. Jul. 7, 2011).
*Reckitt Benckiser LLC* v. *Perrigo Company and Perrigo Research and Development Company,* Complaint for Patent Infringement (D.N.J. Mar. 26, 2015).
*Reckitt Benckiser LLC* v. *Perrigo Company and Perrigo Research and Development Company,* Consent Judgment and Stipulation of Dismissal (D.N.J. Aug. 6, 2015).
*Reckitt Benckiser LLC* v. *Dr. Reddy's Laboratories, Inc.,* Docket Entries (D.N.J.).
*Reckitt Benckiser LLC* v. *Dr. Reddy's Laboratories, Inc. and Dr. Reddy's Laboratories, Ltd.,* Complaint for Patent Infringement (D.N.J. Jun. 26, 2015).
*Reckitt Benckiser LLC* v. *Dr. Reddy's Laboratories, Inc. and Dr. Reddy's Laboratories, Ltd.,* Answer and Counterclaims of Dr. Reddy's Laboratories, Inc. and Dr. Reddy's Laboratories, Ltd. (D.N.J. Sep. 4, 2015).
*Reckitt Benckiser LLC* v. *Dr. Reddy's Laboratories, Inc. and Dr. Reddy's Laboratories, Ltd.,* Plaintiffs' Opposition to Motion for Judgment on the Pleadings (D.N.J. Sep. 18, 2015).
*Reckitt Benckiser LLC* v. *Dr. Reddy's Laboratories, Inc. and Dr. Reddy's Laboratories, Ltd.,* Reckitt's Reply to Dr. Reddy's Laboratories, Inc.'s and Dr. Reddy's Laboratories, LTD.'s Counterclaims (D.N.J. Sep. 28, 2015).
*Reckitt Benckiser LLC* v. *Dr. Reddy's Laboratories, Inc. and Dr. Reddy's Laboratories, Ltd.,* Dr. Reddy's Laboratories' Preliminary Invalidity Contentions (D.N.J. Oct. 21, 2015).
*Reckitt Benckiser LLC* v. *Dr. Reddy's Laboratories, Inc. and Dr. Reddy's Laboratories, Ltd.,* Reckitt's Opposition to Defendants' Motion for Judgment on the Pleadings (D.N.J. Oct. 23, 2015).
*Reckitt Benckiser LLC* v. *Dr. Reddy's Laboratories, Inc. and Dr. Reddy's Laboratories, Ltd.,* Reckitt's Preliminary Responses to Defendants' Invalidity Contentions (D.N.J. Dec. 7, 2015).

(56) References Cited

OTHER PUBLICATIONS

*Reckitt Benckiser LLC* v. *Amneal Pharmaceuticals LLC*, Docket Entries (D.N.J.).
*Reckitt Benckiser LLC* v. *Amneal Pharmaceuticals LLC*, Complaint for Patent Infringement (D.N.J. Mar. 26, 2015).
*Reckitt Benckiser LLC* v. *Amneal Pharmaceuticals LLC*, Ameani Pharmaceuticals LLC's Answer, Affirmative Defenses, and Counterclaims (D.N.J. Jun. 15, 2015).
*Reckitt Benckiser LLC* v. *Amneal Pharmaceuticals LLC*, Reckitt Benckiser's Reply to Amneal Pharmaceuticals LLC's Counterclaims (D.N.J. Jul. 9, 2015).
*Reckitt Benckiser LLC* v. *Amneal Pharmaceuticals LLC*, Defendant Amneal Pharmaceuticals LLC's Rule 12(c) Motion for Judgment on the Pleadings to Plaintiff's Claims for Infringement (D.N.J. Aug. 14, 2015).
*Reckitt Benckiser LLC* v. *Amneal Pharmaceuticals LLC*, Amneal Pharmaceuticals LLC's Non-Infringement Contentions (D.N.J. Aug. 28, 2015).
*Reckitt Benckiser LLC* v. *Amneal Pharmaceuticals LLC*, Amneal Pharmaceuticals LLC's Invalidity Contentions (D.N.J. Aug. 28, 2015).
*Reckitt Benckiser LLC* v. *Amneal Pharmaceuticals LLC*, Plaintiff Reckitt Benckiser's Opposition to Defendant Amneal's Rule 12(c) Motion for Judgment on the Pleadings (D.N.J. Sep. 18, 2015).
*Reckitt Benckiser LLC* v. *Amneal Pharmaceuticals LLC*, Amneal Pharmaceuticals LLC's Answers to Plaintiff Reckitt Benckiser LLC's First Set of Interrogatories (Nos. 1-7) (D.N.J. Oct. 20, 2015).
*Reckitt Benckiser LLC* v. *Amneal Pharmaceuticals LLC*, Amneal Pharmaceuticals LLC's Supplemental Invalidity Contentions (D.N.J. Oct. 21, 2015).
*Reckitt Benckiser LLC* v. *Dr. Reddy's Laboratories, Ltd., et al., Reckitt Benckiser LLC* v. *Amneal Pharmaceuticals LLC, et al.*, Order Denying Judgment on the Pleadings (D.N.J. Jan. 15, 2016).
*Reckitt Benckiser LLC* v. *Amneal Pharmaceuticals LLC*, Stipulation of Dismissal of Claims, Defenses and Counterclaims for U.S. Pat. No. 6,372,252 (D.N.J. May 25, 2016).
*Reckitt Benckiser LLC* v. *Amneal Pharmaceuticals LLC*, Stipulation of Dismissal of Claims, Defenses and Counterclaims for U.S. Pat. Nos. 6,372,252 and 6,955,821 (D.N.J. May 25, 2016).
*Reckitt Benckiser LLC* v. *Amneal Pharmaceuticals LLC*, Reckitt's Opposition to Defendant's Motion for Summary Judgment of Non-Infringement (D.N.J. Jun. 17, 2016).
*Reckitt Benckiser LLC* v. *Amneal Pharmaceuticals LLC*, Supplemental Brief in Support of Defendants' Motion for Summary Judgment of Non-Infringement (D.N.J. Nov. 14, 2016).
*Reckitt Benckiser LLC* v. *Amneal Pharmaceuticals LLC, Reckitt Benckiser LLC* v. *Dr. Reddy's Laboratories, Ltd.*, Order Denying Defendant's Motion for Summary Judgment of Non-Infringement (D.N.J. Dec. 22, 2016).
*Reckitt Benckiser LLC* v. *Amneal Pharmaceuticals LLC*, Joint Claim Construction and Prehearing Statement (D. N.J. Jan. 12, 2017).
*Reckitt Benckiser LLC* v. *Amneal Pharmaceuticals LLC*, Defendants' Opening Claim Construction Brief (D.N.J. Feb. 2, 2017).
*Reckitt Benckiser LLC* v. *Amneal Pharmaceuticals LLC*, Expert Declaration of Dr. Martyn C. Davies (D.N.J. Feb. 23, 2017).

DG 1

PHARMACEUTICAL FORMULATION

PHARMACEUTICAL FORMULATION

This application is a continuation of U.S. application Ser. No. 15/291,061, filed Oct. 11, 2016, which claims the benefit of U.S. Provisional Patent Application Nos. 62/239,775 and 62/239,780, both filed Oct. 9, 2015, the contents of each of which are incorporated by reference herein in their entirety.

TECHNICAL FIELD

The present invention relates to a pharmaceutical formulation. In particular, the present invention is directed to a formulation for oral administration comprising an expectorant, an analgesic, and at least one additional active ingredient which is capable of sustaining a therapeutic effect for each of the actives for at least twelve hours.

BACKGROUND

Pharmaceutical compositions comprising combinations of actives are well-known in the prior art. For example, many over the counter cold and flu remedies include an anti-inflammatory together with an antitussive or cough suppressant. In addition, there are a number of pain killers which are based on a combination of one or more of ibuprofen, aspirin, paracetamol and codeine. There are also available immediate release products which combine more than two actives. For example, the Tylenol® range includes products which combine paracetamol, dextromethorphan and guaifenesin. However, as these products are immediate release products, re-dosing is required every 4 to 6 hours in order to maintain a therapeutic effect.

There is no specific teaching in the prior art of a sustained release dosage form containing guaifenesin, an analgesic and at least one other pharmaceutically active agent which is capable of sustaining a therapeutic effect for each of the actives for at least twelve hours.

Such a combination would be advantageous to develop as it would provide an individual relief from the symptoms of a cough, cold, or flu for an extended period of up to 12 hours. In particular, it would be desirable to develop a product which contains actives that can provide relief from the symptoms of a cough or cold as well as an analgesic. The low solubility of analgesics, however, can impact the dissolution of other active compounds in a combination product. This is particularly true in conventional extended release products where release control is dependent on the erosion of a polymer matrix. Naproxen is an analgesic known in the art to present dissolution/release challenges when formulating the same, especially in combination with other active ingredients.

SUMMARY OF THE INVENTION

The invention is directed to a pharmaceutical composition comprising a pharmaceutically effective amount of each of guaifenesin, naproxen and dextromethorphan.

The invention is further directed to pharmaceutical composition comprising:
 (a) 55-65% guaifenesin;
 (b) 1-5% dextromethorphan or a pharmaceutically acceptable salt thereof;
 (c) 5-15% naproxen or a pharmaceutically acceptable salt thereof;
 (d) 1-10% at least one sustained release polymer;
 (e) 0.1-10% at least one binder;
 (f) 0.1-10% at least one disintegrant;
 (g) 5-25% at least one diluent; and
 (h) up to 1% at least one lubricant.

The invention is still further directed to a pharmaceutical composition comprising:
 (a) 55-65% guaifenesin;
 (b) 1-5% dextromethorphan or a pharmaceutically acceptable salt thereof;
 (c) 5-15% naproxen or a pharmaceutically acceptable salt thereof;
 (d) 1-8% hypromellose;
 (e) 5-10% microcrystalline cellulose;
 (f) 0.1-2% sodium lauryl sulfate;
 (g) 1-10% sodium bicarbonate;
 (h) 0.1-4.0% croscarmellose sodium;
 (i) 0.1-10% polyethylene glycol 4000;
 (j) 1-2% hydroxyethyl cellulose; and
 (k) 0.5-1% magnesium stearate.

The invention is also directed to a pharmaceutical composition comprising guaifenesin, naproxen and dextromethorphan and at least one pharmaceutically acceptable component, wherein about 100% of naproxen dissolves within 30 minutes in a pH 6.8 phosphate buffer.

The invention is also directed to a pharmaceutical composition comprising guaifenesin, naproxen and dextromethorphan and at least one pharmaceutically acceptable component, wherein the pharmaceutical composition provides a mean $C_{max}$ and at least one of a mean $AUC_{inf}$ and a mean $AUC_{0-12}$ for naproxen under fasted conditions based on single-dose administration that are from 80% to 125% of the mean $C_{max}$ and at least one of the mean $AUC_{inf}$ and the mean $AUC_{0-12}$ for naproxen provided by a pharmaceutical composition comprising (a) 58-63% guaifenesin; (b) 2-3.5% dextromethorphan or a pharmaceutically acceptable salt thereof; (c) 10-12% naproxen or a pharmaceutically acceptable salt thereof; (d) 1-3% hypromellose; (e) 5-8% microcrystalline cellulose; (f) 1-2% hydroxyethyl cellulose; (g) 0.5-2.5% croscarmellose sodium; (h) 0.5-1.5% sodium lauryl sulfate; (i) 5-8% sodium bicarbonate; (j) 5-8% polyethylene glycol 4000; and (k) 0.5-1% magnesium stearate.

Preferred embodiments of the invention include pharmaceutical compositions which comprise an immediate release portion and a modified release portion; wherein the dissolution profile of each of the guaifenesin and the dextromethorphan are substantially the same as the dissolution profile of each of guaifenesin and dextromethorphan in a pharmaceutical composition which does not contain naproxen; wherein the dissolution profile of naproxen is substantially the same as the dissolution profile of naproxen in a pharmaceutical composition which does not contain guaifenesin and dextromethorphan; wherein the dissolution of naproxen occurs independently of guaifenesin and dextromethorphan; wherein the dissolution of guaifenesin and dextromethorphan occurs independently of naproxen; wherein an immediate release portion comprises sodium lauryl sulfate and sodium bicarbonate; wherein a ratio of guaifenesin:naproxen:dextromethorphan is from about 40:8:1 to about 10:3:1; wherein the pharmaceutical composition is a bilayer tablet; wherein the pharmaceutical composition is produced by a non-aqueous granulation process; wherein less than 1% of particles comprising an immediate release portion have a particle size diameter of greater than 1000 µm; and/or wherein the pharmaceutical composition provides a therapeutic effect in respect of each of guaifenesin, naproxen and dextromethorphan for a period of up to 12 hours.

DETAILED DESCRIPTION OF THE INVENTION

Figure 1:
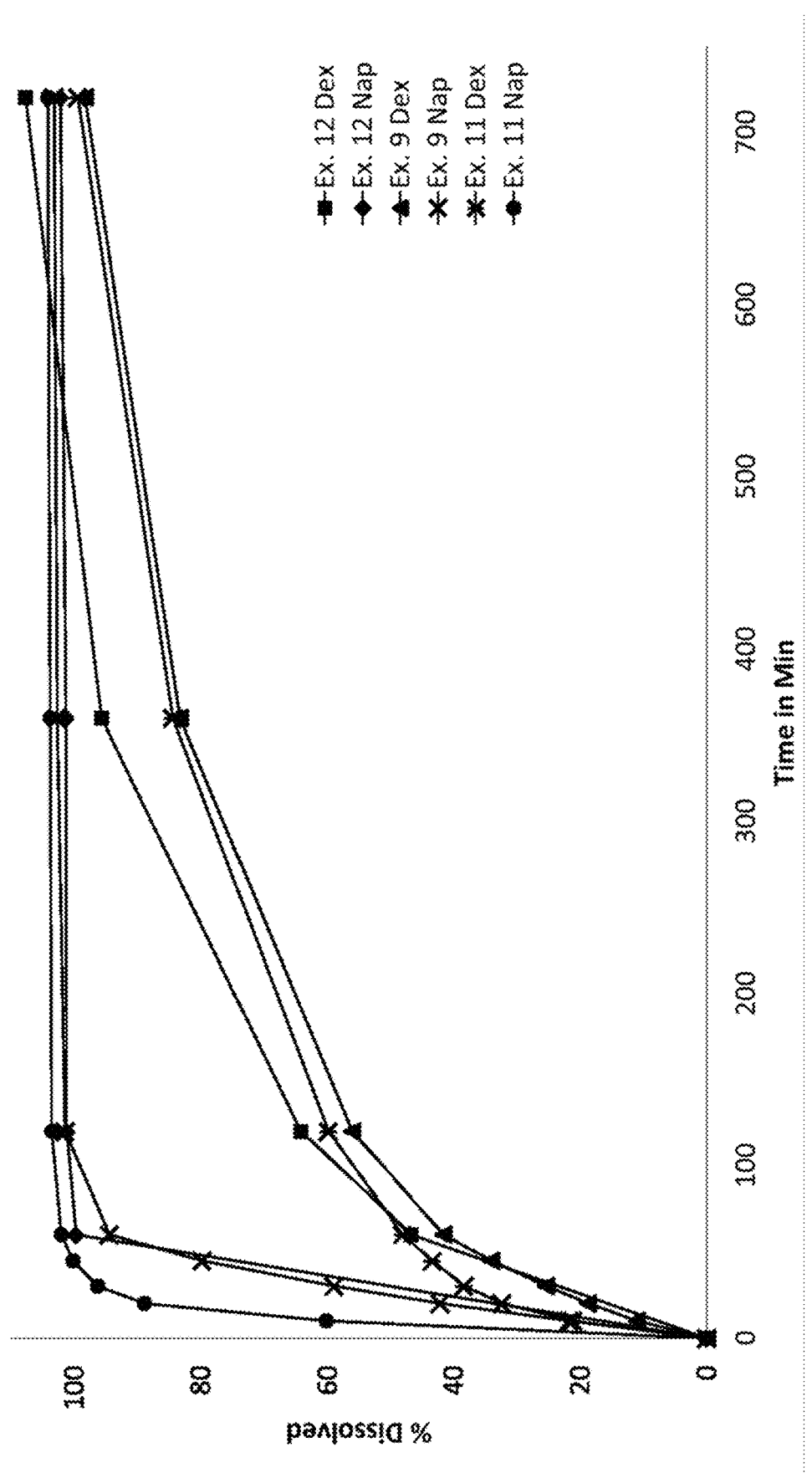
FIG. 1 shows dextromethorphan and naproxen dissolution results at pH 5.0 (simulated fed state) for embodiments of the present invention.
Figure 2:
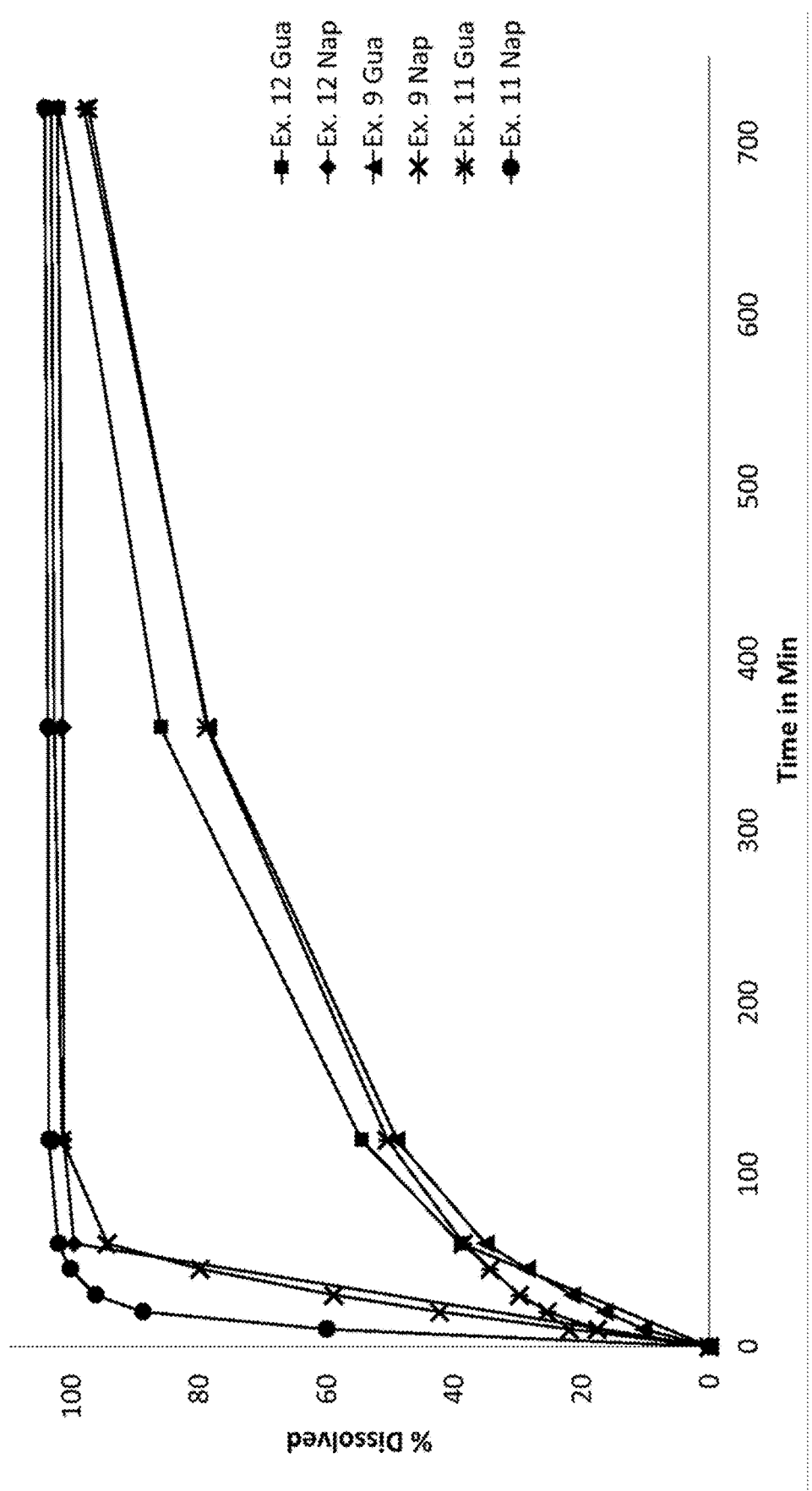
FIG. 2 shows guaifenesin and naproxen dissolution results at pH 5.0 (simulated fed state) for embodiments of the present invention.
Figure 3:
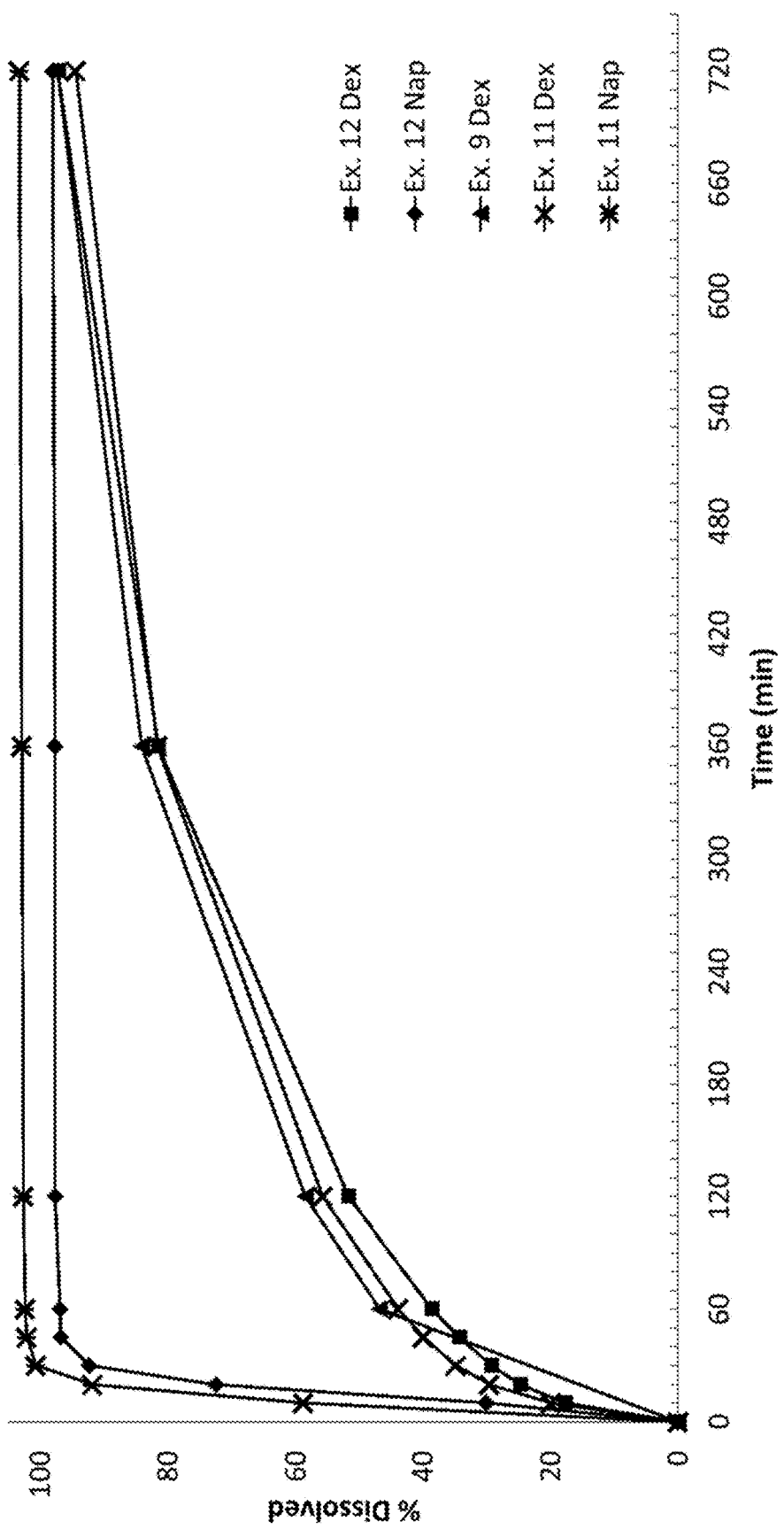
FIG. 3 shows dextromethorphan and naproxen dissolution results at pH 6.8 (simulated fasted state) for embodiments of the present invention.
Figure 4:
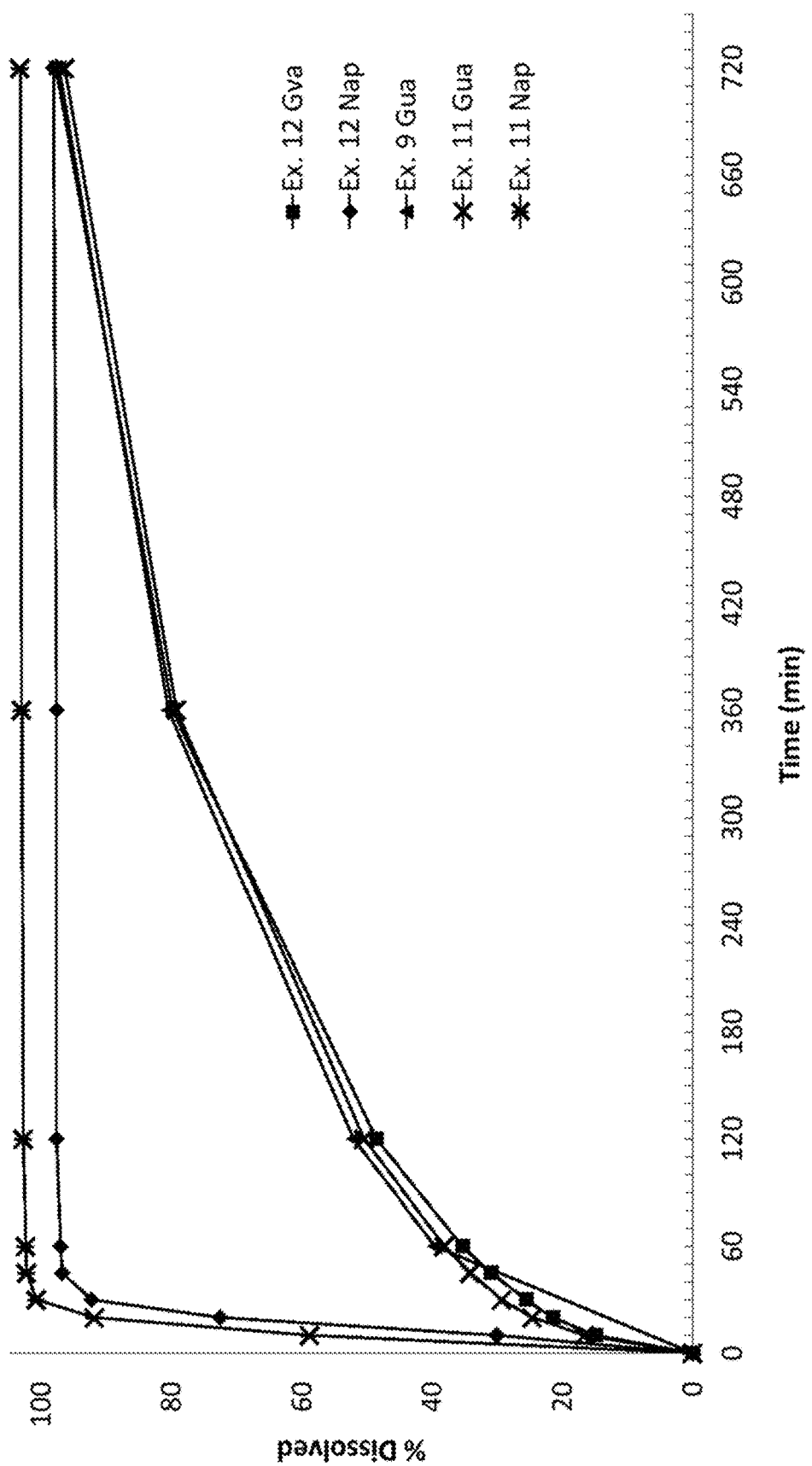
FIG. 4 shows guaifenesin and naproxen dissolution results at pH 6.8 (simulated fasted state) for embodiments of the present invention.

According to a first aspect of the present invention, there is provided a pharmaceutical composition comprising a pharmaceutically effective amount of at least three different pharmaceutical actives—an expectorant, an analgesic and at least one additional active ingredient which is an antitussive, a decongestant or an antihistamine. Preferably the composition provides a therapeutic effect in respect of each active for a period of up to 12 hours.

For the avoidance of any doubt, reference to a pharmaceutically active compound includes all enantiomers and stereoisomers thereof, and also all pharmaceutically acceptable salts or esters thereof. For example, naproxen includes naproxen sodium, pseudoephedrine includes pseudoephedrine hydrochloride, and dextromethorphan includes dextromethorphan hydrobromide. All pharmaceutical actives suitable for use in the present invention can be made according to known synthetic procedures or obtained from known commercial sources. In addition, all % amounts referred to herein refer to % by weight of either a total composition or a portion or layer thereof as indicated.

The expectorant according to the first aspect of the invention is selected from ambroxol, acetylcysteine, carboxycysteine, erdosteine, potassium guaiacolsulfonate, potassium iodide, guaifenesin, and combinations thereof. Guaifenesin is preferred for use in the present invention. The pharmaceutically effective amount of expectorant in the pharmaceutical composition can range from about 200 mg to 2400 mg, more preferably about 600 mg to 1200 mg, and most preferably is 600 mg or 1200 mg.

The analgesic according to the first aspect of the invention is a non-steroidal anti-inflammatory drug, preferably selected from naproxen, ketoprofen, diclofenac, ibuprofen, flurbiprofen and combinations thereof. The pharmaceutically effective amount of analgesic in the pharmaceutical composition can range from about 5 mg to 4000 mg, more preferably about 110 mg to 220 mg, and most preferably is 110 mg or 220 mg.

The at least one additional active ingredient according to the first aspect of the invention is an antitussive, a decongestant or an antihistamine. Suitable antitussives include, without limitation, dextromethorphan, codeine, codeine phosphate, codeine sulphate, diphenhydramine citrate, diphenhydramine hydrochloride, and combinations thereof. Suitable decongestants include, without limitation, phenylephrine hydrochloride, phenylpropanolamine hydrochloride, pseudoephedrine, ephedrine, and combinations thereof. Suitable antihistamines include, without limitation, chlorpheniramine maleate, brompheniramine maleate, phenindamine tartrate, pyrilamine maleate, doxylamine succinate, phenyltoloxamine citrate, diphenhydramine hydrochloride, promethazine, clemastine fumerate, tripolidine, and combinations thereof. According to a preferred embodiment, the at least one additional active ingredient is dextromethorphan or pseudoephedrine.

When the at least one additional active ingredient is dextromethorphan, the pharmaceutically effective amount of dextromethorphan in the pharmaceutical composition can range from about 10 mg to 120 mg, more preferably about 15 mg to 60 mg, still more preferably about 25 mg to 35 mg, and most preferably is 30 mg or 60 mg. When the at least one additional active ingredient is pseudoephedrine, the total amount of pseudoephedrine in the pharmaceutical composition can range from about 10 mg to 240 mg, and more preferably about 60 mg to 120 mg.

In a preferred embodiment, the expectorant is guaifenesin, the analgesic is naproxen and the antitussive is dextromethorphan. In such an embodiment, the ratio of guaifenesin:naproxen:dextromethorphan can be from about 40:8:1 to about 10:3:1, more preferably from 22:4:1 to 17:3:1, and most preferably is 20:3.67:1. In such an embodiment, the ratio of guaifensin:naproxen can be from about 1:1 to about 10:1, more preferably from about 2:1 to about 7:1, still more preferably from about 4:1 to about 6:1, and most preferably is about 5.45:1. In such an embodiment, the ratio of the naproxen:dextromethorphan can be from about 1:1 to about 10:1, more preferably from about 2:1 to about 7:1, still more preferably from about 3:1 to about 5:1, and most preferably is about 3.67:1.

When an active other than dextromethorphan is used as the at least one additional active ingredient, the ratio of naproxen:antitussive/decongestant/antihistamine can be from 10:1 to 2:1.

When flurbiprofen is the analgesic, the ratio of expectorant:analgesic:antitussive/decongestant/antihistamine can be from 25:5:1 to 5:0.5:1, with the ratio of expectorant:analgesic from 10:1 to 5:1, and the ratio of analgesic:antitussive/decongestant/antihistamine from 1:1.5 to 1:0.2.

When ibuprofen is the analgesic, the ratio of expectorant:analgesic:antitussive/decongestant/antihistamine can be from 25:30:1 to 5:5:1, with the ratio of expectorant:analgesic from 1:1 to 1:5, and the ratio of analgesic:antitussive/decongestant/antihistamine from 30:1 to 5:1.

When diclofenac is the analgesic, the ratio of expectorant:analgesic:antitussive/decongestant/antihistamine can be from 25:5:1 to 5:0.5:1, with the ratio of expectorant:analgesic from 20:1 to 5:1, and the ratio of analgesic:antitussive/decongestant/antihistamine from 1:2 to 1:0.2.

When ketoprofen is the analgesic, the ratio of expectorant:analgesic:antitussive/decongestant/antihistamine can be from 25:5:1 to 5:0.5:1, with the ratio of expectorant:analgesic from 10:1 to 5:1, and the ratio of analgesic:antitussive/decongestant/antihistamine from 1:1.5 to 1:0.2.

The pharmaceutical composition of the first aspect of the invention can be in the form of one or more tablets, caplets, or capsules, gel, elixir, suspension, syrup, emulsion, powder, or granules. Capsules can be soft capsules or hard capsules. When the composition is in the form of one or more than one tablets or caplets, the tablet(s) or caplet(s) may be contained within a single capsule. A capsule can be made of any suitable material, but is typically made of a gelatin material, hydroxyl propyl methyl cellulose or an alginate. In a preferred embodiment, the capsule is obtained from two shells of hard gelatin which are sealed together around the combined tablets. Alternatively, the capsule can be a one-piece capsule. Soft gelatin capsules are usually prepared from gelatin, glycerin and water, and can absorb several times their own weight in water. Other non-limiting materials for making capsules of the present invention include cellulose esters and/or ethers such as, e.g., hydroxypropylmethylcellulose (HPMC).

Typically, the one or more than one tablets are not in the form of a powdered or granulated composition. Preferably the one or more than one tablets do not comprise a natural gum, such as xanthan gum. After dissolution of the capsule, the one or more than one tablets release the active pharmaceutical ingredients contained therein comparably to each of the at least two tablets being administered individually.

The one or more than one tablets can have the same or a different geometric form, the same or a different weight, and the same or a different volume with the proviso that at least one of the geometric form, weight or volume is different between the tablets. For the avoidance of doubt, in the event that the dosage form comprises three or more tablets, then two or more of the tablets can have the same dimensions. The one or more than one tablets can be coated or uncoated.

The dimensions of the capsule can be selected such that the pharmaceutical dosage form has a shape which is compatible with easy swallowing. The capsule can generally be in the shape of a sphere or an elongated sphere (oblong form). The capsule can have a length of up to 35 mm, a width of up to 15 mm and a depth of up to 15 mm. In a preferred embodiment, the capsule can have a length of 25-30 mm, a width of 8-10, and a depth of 8-10 mm.

The one or more than one tablets can have a surface that is complementary to the face of an adjacent tablet, the two faces being intended to be opposite one another in the final pharmaceutical dosage form. The two faces can be planar or substantially planar. Alternatively, the one or more than one tablets can have a round or ovoid/oval geometry.

Figure 22:
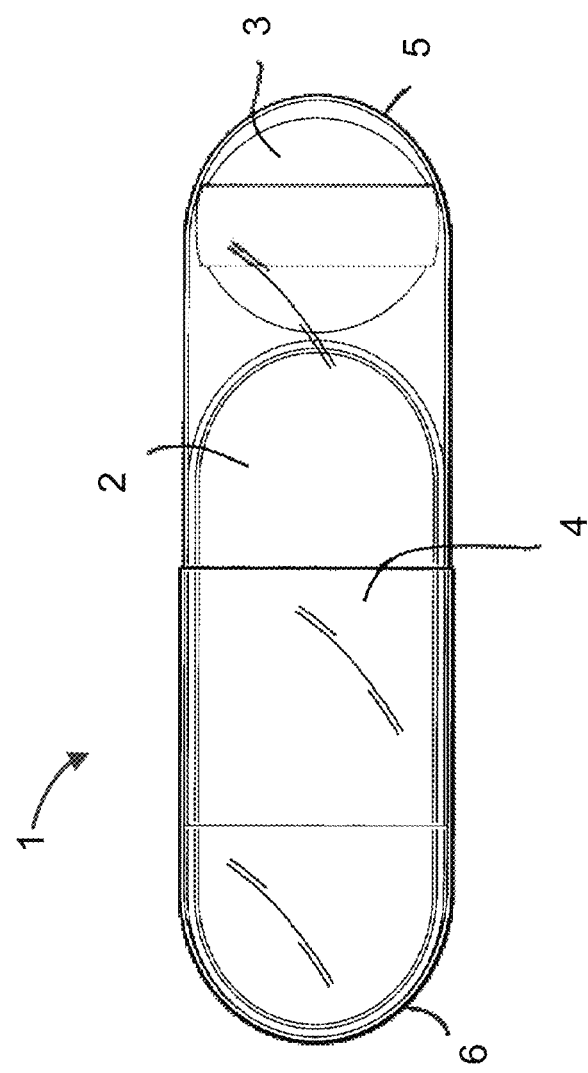
FIGS. 22-25 show example embodiments of a capsule formulation according to the present invention.
Figure 23:
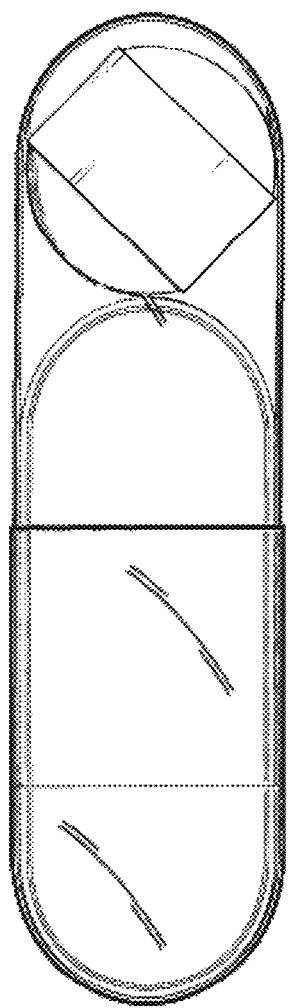
Figure 24:
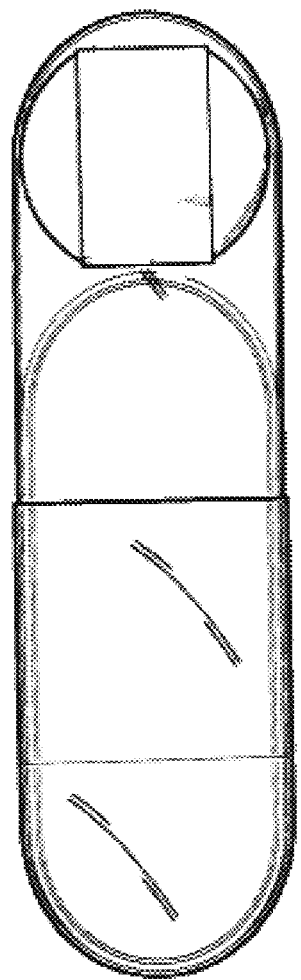
Figure 25:
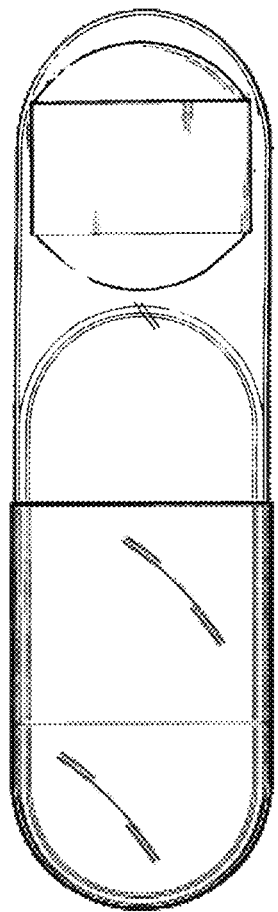

Referring firstly to FIG. 22, a pharmaceutical dosage form in accordance with the present invention is generally depicted at 1. The dosage form 1 comprises a first tablet 2 and a second tablet 3. The tablets 2 and 3 are encased in a gelatin or HPMC capsule 4. The gelatin or HPMC capsule comprises two separate shells 5 and 6. The capsule shells 5 and 6 have different dimensions such that one of the shells is larger than the other. Each of the shells 5 and 6 are provided with means in the form of grooves that allow the shells to reversibly engage with each other. The pharmaceutical dosage form 1 is made by inserting the tablets into the longer shell 5. Shell 6 is then connected to shell 5 to form the final dosage form 1. The tablets of the example embodiments of the present invention can be used using standard tableting procedures well-known to the man skilled in the art. FIGS. 23-25 illustrate alternative embodiments of the present invention in which the tablets are different.

The geometric form of the one or more than one tablets is adapted to the needs of the final dosage form. For example, an existing tablet can be used but its dimensions can be altered without changing the qualitative and quantitative composition of the original tablet.

The pharmaceutical composition preferably comprises immediate and sustained release portions. As set forth herein, "portion" means a part of a whole, either separated or integrated with it. Thus, a product with two or more portions may have, but does not necessarily require, separate or discrete structural elements, e.g., layers. In a particularly preferred embodiment of the invention, the pharmaceutical composition is an oral solid dosage form that is a bilayer tablet. As further set forth herein "sustained release" refers to a pharmaceutical formulation designed to inhibit, retard, or extend release of the active pharmaceutical ingredient(s); "immediate release" refers to a pharmaceutical formulation designed to rapidly release the active pharmaceutical ingredient(s); and "modified release" refers to a pharmaceutical formulation comprising both a sustained release quantity of active pharmaceutical ingredient and an immediate release quantity of active pharmaceutical ingredient, i.e., having both sustained release and immediate release properties. The amount of sustained release quantity and immediate release quantity may or may not be readily measured or numerically quantified.

The analgesic can be incorporated into the composition such that it is the sole active in the portion in which it is contained. Typically, the composition is provided with both sustained release and immediate release portions comprising the expectorant.

A preferred embodiment of the first aspect of the invention is a pharmaceutical composition which comprises at least three distinct portions wherein two of the portions have immediate release characteristics and a third has sustained release characteristics, wherein one of the immediate release portions comprises an expectorant and an additional active ingredient which is an antitussive or a decongestant, and the second immediate release portion comprises an analgesic having a half-life of twelve hours, and wherein the sustained release portion comprises guaifenesin and an additional active ingredient which is an antitussive or a decongestant. This pharmaceutical composition may comprise a first composition which comprises both immediate and sustained release portions of the expectorant and the additional active ingredient which is an antitussive or a decongestant and a second composition which comprises an analgesic having a therapeutic effect of twelve hours.

In a further preferred embodiment of the first aspect of the invention, the pharmaceutical composition comprises a first immediate release portion which comprises guaifenesin and a decongestant or an antitussive, a second immediate release portion which comprises naproxen, and a sustained release portion which comprises guaifenesin and a decongestant or an antitussive. In further preferred embodiments, the antitussive can be dextromethorphan or the decongestant can be pseudoephedrine.

In still another preferred embodiment, a first immediate release portion and a sustained release portion constitute a bilayer tablet and a second immediate release portion is another tablet. In a more preferred embodiment, the bilayer tablet and the another tablet are contained in a capsule.

In another preferred embodiment, the pharmaceutical composition takes the form of a bilayer tablet, which can be manufactured according to any method known to those of ordinary skill in the art. The resulting tablet may comprise the two portions compressed against one another so that the face of each portion is exposed as either the top or bottom of the tablet, or the resulting tablet may comprise the sustained release portion in the center coated by the immediate release portion so that only the immediate release portion is exposed. In a more preferred embodiment, a bilayer tablet of the present invention comprises the two portions compressed against one another so that the face of each portion is exposed.

As would be readily understood by one of ordinary skill in the art, the pharmaceutical compositions of the first aspect of the present invention may comprise at least one pharmaceutically acceptable component in addition to the three different pharmaceutical actives. Such components include, without limitation, polymers as binders, lubricants, colorants, other binders, surface active agents, disintegrants, diluents, glidants, preservatives, stabilizers, fillers, antiadherents, coatings and any other component known to one of ordinary skill in the art. When present, these components are present in an amount which can be readily determined by one of ordinary skill in the art. As would be further readily understood by one of ordinary skill in the art, one or more of these components may be more suited for inclusion in a sustained release portion or an immediate release portion, when such portions are present in the pharmaceutical composition of the present invention. For example, a sustained release portion of a pharmaceutical composition may additionally preferably comprise one or more of polymers as binders, lubricants, colorants, other binders, glidants, surface active agents, and preservatives, while an immediate release portion may additionally preferably comprise one or more of disintegrants, lubricants, colorants, binders, glidants, surface active agents, preservatives, and stabilizers.

Sustained release polymers suitable for use as binders in the pharmaceutical compositions of the present invention include, without limitation, acacia, adipic acid, agar, alginic acid, aliphatic polyesters, calcium alginate, carbomer, carrageenan, castor oil, cellaburate, cellulose acetate, ceratonia, colophony, copovidone, glyceryl behenate, glyceryl monooleate, glyceryl monostearate, glyceryl palmitostearate, hydroxypropyl betadex, hydroxypropyl cellulose, hydroxyethyl cellulose, hypromellose, hypromellose acetate succinate, methylcellulose, polacrilin potassium, polycarbophil, polydextrose, poly methacrylates, polyoxylglycerides, polyvinyl acetate dispersion, shellac, sodium alginate, sodium hyaluronate, modified starch, sucrose stearate, microcrystalline wax, white wax, yellow wax, xanthan gum, zein, and combinations thereof. As would be readily appreciated by one of ordinary skill in the art, such sustained release polymers are best suited for inclusion in a sustained release portion of a pharmaceutical composition.

Hydrophilic polymers suitable for use, especially in a sustained release portion, in a pharmaceutical composition of the present invention include, without limitation, one or more natural or partially or totally synthetic hydrophilic gums such as acacia, gum tragacanth, locust bean gum, guar gum, and karaya gum; modified cellulosic substances such as methylcellulose, hydroxy methylcellulose, hydroxypropyl methylcellulose, hydroxyethyl cellulose, hydroxypropyl cellulose, hydroxyethylcellulose, carboxyethylcellulose; proteinaceous substances such as agar, pectin, carrageen, and alginates; and other hydrophilic polymers such as carboxypolymethylene, gelatin, casein, zein, bentonite, magnesium aluminium silicate, polysaccharides, and modified starch derivatives, and other hydrophilic polymers known to those of skill in the art and combinations thereof.

These hydrophilic polymers gel and dissolve slowly in aqueous acidic media thereby allowing the expectorant, e.g., guaifenesin to diffuse from the gel in the stomach. When the gel reaches the intestines, it dissolves in controlled quantities in the higher pH medium, where the guaifenesin itself is fairly absorbable, to allow sustained release of guaifenesin throughout the digestive tract. Preferred hydrophilic polymers are the hydroxypropyl methylcelluloses such as those manufactured by the Dow Chemical Company and known as METHOCEL™ ethers. In one preferred embodiment of a sustained release formulation, the hydrophilic polymer is a METHOCEL™ ether known as METHOCEL™ E10M.

Water-insoluble polymers suitable for use, especially in a sustained release portion, in a pharmaceutical composition of the present invention are polymers which generally do not dissolve in solutions of a pH below 5 and dissolve more slowly in basic solutions than the hydrophilic polymers. Because the polymer is insoluble in low pH environments such as those found in gastric fluid, it aids in retarding drug release in those regions. Likewise, because the polymer dissolves more slowly in solutions of higher pH than hydrophilic polymers, it aids in retarding drug release throughout the intestines. This overall delayed release results in a more uniform serum concentration of expectorant, e.g., guaifenesin.

Water-insoluble polymers suitable for use then include, without limitation, polyacrylic acids, acrylic resins, acrylic latex dispersions, cellulose acetate phthalate, polyvinyl acetate phthalate, hydroxypropyl methylcellulose phthalate, carbomer, other polymers known to those of skill in the art, and combinations thereof. In a preferred embodiment, a sustained release portion comprises the acrylic resin CARBOPOL® 974P supplied by BF Goodrich.

Other suitable binders include, without limitation, attapulgite, calcium carbonate, calcium lactate, ceratonia, colophony, copovidone, ethylcellulose, ethylene glycol and vinyl alcohol grafted copolymer, gelatin, glucose, hydroxethylmethyl celluose, magnesium aluminium silicate, methylcellulose, poly carbophil, poly dextrose, polyethylene oxide, polymethacrylates, povidone, pullulan, vitamin E polyethylene glycol succinate, sucrose, lactose, starch paste, acacia, tragacanth, povidone, polyethylene glycol, corn syrup and combinations thereof.

Lubricants suitable for use include, without limitation, magnesium stearate, calcium stearate, zinc stearate, powdered stearic acid, hydrogenated vegetable oils, talc, polyethylene glycol, mineral oil and combinations thereof. calcium stearate, glyceryl behenate, leucine, magnesium stearate, mineral oil, myristic acid, palm oil, palmitic acid, poloxamer, polyethylene glycol, potassium benzoate, sodium benzoate, sodium lauryl sulfate, sodium stearate, sodium stearyl fumarate, stearic acid, sucrose stearate, talc, vegetable oil, zinc stearate Colorants suitable for use include, without limitation, emerald green lake, FD&C Red #40, FD&C Yellow #6, FD&C Yellow #10, FD&C Blue #1 and combinations thereof. In one preferred embodiment, a sustained release portion further comprises magnesium stearate and emerald green lake. In another preferred embodiment, a sustained release formulation further comprises magnesium stearate and FD&C Blue #1 aluminum lake dye.

Glidants suitable for use include, without limitation, colloidal silicon dioxide, talc and combinations thereof.

Surface active agents suitable for use include, without limitation, sodium lauryl sulfate, dioctyl sodium sulfosuccinate, triethanolamine, polyoxyethylene sorbitan, poloxalkol, quarternary ammonium salts and combinations thereof.

Preservatives suitable for use include, without limitation, benzyl alcohol, parabens, cetylpyridine chloride, glycerin, potassium sorbate, sodium benzoate, sorbic acid, sodium propionate, and combinations thereof.

Stabilizers suitable for use include, without limitation, alginate, colloidal silicone dioxide, corn starch, glycerin, hydroxypropyl celluloses, hydroxypropyl methylcelluloses, propylene glycol, saccharin sodium, and combinations thereof.

Suitable disintegrants include, without limitation, carboxy methylcellulose calcium, carboxymethylcellulose sodium, chitosan, colloidal silicon dioxide, croscarmellose sodium, crospovidone, glycine, guar gum, lactose, magnesium aluminum silicate, polacrilin potassium, povidone, sodium alginate, sodium starch glycolate.

Suitable diluents include, without limitation, calcium carbonate, calcium lactate, calcium phosphate, calcium silicate, calcium sulfate, cellaburate, cellulose acetate, microcrystalline cellulose, silicified microcrystalline cellulose, corn syrup solids, dextrates, dextrin, dextrose, erythritol, ethylcellulose, fructose, inulin, isomalt, kaolin, lactitol, lactose, magnesium carbonate, magnesium oxide, maltitol, maltodextrin, maltose, mannitol, triglycerides, polydextrose, simethicone, sodium bicarbonate, sodium carbonate, sodium chloride, sorbitol, sucrose, sugar, sulfobutylether β-cyclodextrin, sunflower oil, talc, trehalose, xylitol, and combinations thereof.

Other excipients suitable for use include, without limitation, lactose, mannitol, glucose, fructose, xylose, galactose, sucrose, maltose, xylitol, sorbitol, chloride, sulfate and phosphate salts of potassium, sodium, and magnesium, and combinations thereof.

In an alternative embodiment, the immediate release portion which comprises guaifenesin may further comprise the additional or more actives in the form of a drug/active-resin complex.

The pharmaceutical composition of the first aspect of the present invention may be made by any known formulary technique. For example, when the pharmaceutical composition takes the form of a tablet, the tablets can be made using standard tableting procedures well-known to the person of ordinary skill in the art.

The pharmaceutical composition according to the first aspect may comprise:
(a) 50-85% guaifenesin;
(b) up to 5% dextromethorphan or a pharmaceutically acceptable salt thereof; and
(c) 5-30% naproxen or a pharmaceutically acceptable salt thereof.

The pharmaceutical composition according to the first aspect may comprise:
(a) 55-65% guaifenesin;
(b) 1-5% dextromethorphan or a pharmaceutically acceptable salt thereof;
(c) 5-15% naproxen or a pharmaceutically acceptable salt thereof;
(d) 1-10% sustained release polymers;
(e) 0.1-10% binders;
(f) 0.1-5% disintegrants;
(g) 5-25% diluents; and
(h) up to 1% lubricants.

A preferred embodiment of the composition according to the first aspect may comprise:
(a) 55-65% guaifenesin;
(b) 1-5% dextromethorphan or a pharmaceutically acceptable salt thereof;
(c) 5-15% naproxen or a pharmaceutically acceptable salt thereof;
(d) 1-8% hypromellose;
(e) 10-25% microcrystalline cellulose;
(f) 0.1-2.5% povidone;
(g) 0.1-4.0% croscarmellose sodium;
(h) 0.1-2.0% hydroxy ethyl cellulose; and
(i) up to 1% magnesium stearate.

Another preferred pharmaceutical composition may comprise:
(a) 58-63% guaifenesin;
(b) 2-3.5% dextromethorphan or a pharmaceutically acceptable salt thereof;
(c) 10-12% naproxen or a pharmaceutically acceptable salt thereof;
(d) 1-2% hypromellose;
(e) 15-25% microcrystalline cellulose;
(f) 1-2% povidone;
(g) 0.5-2.5% croscarmellose sodium;
(h) 0.5-1% hydroxyethyl cellulose; and
(i) up to 0.5% magnesium stearate.

In still another preferred embodiment, the pharmaceutical composition may comprise:
(a) 55-65% guaifenesin;
(b) 1-5% dextromethorphan or a pharmaceutically acceptable salt thereof;
(c) 5-15% naproxen or a pharmaceutically acceptable salt thereof;
(d) 1-8% hypromellose;
(e) 10-25% microcrystalline cellulose;

(f) 0.1-2.5% povidone;
(g) 0.1-2.0% carbomer;
(h) 0.1-2.0% sodium starch glycolate; and
(i) up to 1% magnesium stearate.

In a still further preferred embodiment, the pharmaceutical composition may comprise:
(a) 59-65% guaifenesin;
(b) 3-5% dextromethorphan or a pharmaceutically acceptable salt thereof;
(c) 10-12% naproxen or a pharmaceutically acceptable salt thereof;
(d) 1-6% hypromellose;
(e) 10-20% microcrystalline cellulose;
(f) 0.3-1% povidone;
(g) 0.5-1% carbomer;
(h) 0.1-0.5% sodium starch glycolate; and
(i) up to 1% magnesium stearate.

In another preferred embodiment, the pharmaceutical composition may comprise:
(a) 59-65% guaifenesin;
(b) 3-5% dextromethorphan or a pharmaceutically acceptable salt thereof;
(c) 10-12% naproxen or a pharmaceutically acceptable salt thereof;
(d) 1-6% hypromellose;
(e) 10-20% microcrystalline cellulose;
(f) 0.3-1% povidone;
(g) 0.5-1% carbomer;
(h) 1-2% croscarmellose sodium;
(i) 0.1-0.5% sodium starch glycolate; and
(j) up to 1% magnesium stearate.

In a preferred embodiment of the first aspect of the present invention, an analgesic-containing immediate release portion can comprise:
(a) 50-52% naproxen or a pharmaceutically acceptable salt thereof;
(b) 35-40% microcrystalline cellulose;
(c) up to 5% povidone;
(d) 5-8% croscarmellose sodium; and
(e) up to 1% magnesium stearate.

In alternative preferred embodiments of the first aspect of the invention, an analgesic-containing immediate release portion can comprise:
(a) 70-75% naproxen or a pharmaceutically acceptable salt thereof;
(b) 20-25% microcrystalline cellulose;
(c) up to 5% povidone;
(d) up to 1% magnesium stearate.

In a preferred embodiment of the first aspect of the present invention, a guaifenesin-containing immediate release portion can comprise:
(a) 30-40% guaifenesin;
(b) up to 5% dextromethorphan or a pharmaceutically acceptable salt thereof;
(c) 50-60% microcrystalline cellulose;
(d) up to 7% povidone;
(e) up to 7% croscarmellose sodium; and
(f) up to 1% magnesium stearate.

In alternative preferred embodiments of the first aspect of the present invention, a guaifenesin-containing immediate release portion can comprise:
(a) 40-50% guaifenesin;
(b) up to 5% dextromethorphan or a pharmaceutically acceptable salt thereof;
(c) 40-50% microcrystalline cellulose;
(d) up to 5% hypromellose;
(e) up to 5% sodium starch glycolate; and
(f) up to 1% magnesium stearate.

In a preferred embodiment of the first aspect of the present invention, a sustained release portion can comprise:
(a) 80-90% guaifenesin;
(b) up to 5% dextromethorphan or a pharmaceutically acceptable salt thereof;
(c) up to 10% hypromellose;
(d) up to 5% carbomer; and
(e) up to 1.55% magnesium stearate.

In alternative preferred embodiments of the first aspect of the present invention, a sustained release portion can comprise:
(a) 80-90% guaifenesin;
(b) 3-6% dextromethorphan or a pharmaceutically acceptable salt thereof;
(c) up to 5% hypromellose;
(d) up to 2% hydroxyethyl cellulose;
(e) up to 5% microcrystalline cellulose; and
(f) up to 1% magnesium stearate.

According to a second aspect of the present invention, there is provided a sustained-release polymer matrix which consists essentially of a combination of a hydroxypropylmethyl cellulose having a molecular weight of 100,000-500,000 and a hydroxyethyl cellulose having a molecular weight of 500,000-2,000,000. This polymer matrix is suitable for use in a sustained release portion of a pharmaceutical composition according to the first aspect of the invention.

The molecular weight of the hydroxypropylmethyl cellulose is more preferably 200,000 to 300,000, and most preferably is 250,000. The molecular weight of the hydroxyethyl cellulose is more preferably 1,000,000 to 1,500,000, and most preferably is 1,300,000. A ratio of the hydroxypropylmethyl cellulose:hydroxyethyl cellulose ranges from 1:1 to 3:1, more preferably from 2:1 to 2.5:1, and most preferably is 2.1:1 or 1:1.

According to a third aspect of the present invention, there is provided a pharmaceutical composition comprising a pharmaceutically effective amount of each of guaifenesin, naproxen and dextromethorphan. Amounts of each of these active ingredients, ratios of inclusion, and sources are the same for the third aspect of the invention as noted above with regard to the first aspect of the invention.

Ideally the dissolution profile of each of the guaifenesin and the dextromethorphan is substantially the same as the dissolution profile of each of guaifenesin and dextromethorphan in a pharmaceutical composition which does not contain naproxen, e.g., Mucinex® DM. Likewise, the dissolution profile of naproxen is substantially the same as the dissolution profile of naproxen in a pharmaceutical composition which does not contain guaifenesin and dextromethorphan. As used herein, "substantially the same" refers to having a dissolution profile that is the same or better than a comparitor naproxen product that does not contain guaifenesin and dextromethorphan, e.g., Aleve®. In other words, the dissolution or release of naproxen occurs independently of the dissolution or release of guaifenesin and dextromethorphan and/or the dissolution or release of guaifenesin and dextromethorphan occurs independently of the dissolution or release of naproxen. In still other words, the dissolution of naproxen is not affected by the presence of guaifenesin and dextromethorphan and/or the dissolution of guaifenesin and dextromethorphan is not affected by the presence of naproxen.

As in the first aspect of the invention, the pharmaceutical composition of the third aspect can be in the form of one or more tablets, caplets, or capsules, gel, elixir, suspension, syrup, emulsion, powder, or granules. Details with regard to these dosage forms are the same for the third aspect as noted above with regard to the first aspect. A preferred embodiment of the third aspect is directed to an oral solid dosage form such as a tablet. Both matrix tablets and tablets having discrete portions are included in this aspect of the invention. A more preferred embodiment is directed to a bilayer tablet.

In a preferred embodiment of the third aspect of the invention, the pharmaceutical composition comprises an immediate release portion and a modified release portion as defined above with regard to the first aspect. In a further preferred embodiment, substantially all of the naproxen is contained in the immediate release portion. As used herein, "substantially all" refers to at least 90%, more preferably at least 95%, and most preferably 100%, of the amount included. In a still further preferred embodiment, a substantial amount of the guaifenesin is contained in the modified release portion and/or a substantial amount of the dextromethorphan is contained in the modified release portion. As used herein, "a substantial amount" refers to at least 65%, more preferably at least 75%, and most preferably about 83%, of the amount included with regard to guaifenesin and at least 55%, more preferably at least 65%, and most preferably about 73% with regard to dextromethorphan. In another preferred embodiment, guaifenesin is contained in both the immediate release portion and the modified release portion and/or dextromethorphan is contained in both the immediate release portion and the modified release portion. Pharmaceutical compositions of the third aspect having immediate and sustained release portions exhibit the same independent dissolution for each of guaifenesin, dextromethorphan and naproxen explained above.

In another preferred embodiment of the third aspect, the pharmaceutical composition takes the form of a matrix tablet which exhibits the same independent dissolution for each of guaifenesin, dextromethorphan and naproxen explained above.

The pharmaceutical compositions of the third aspect of the invention may include additional components such as, without limitation, polymers as binders, lubricants, colorants, other binders, surface active agents, disintegrants, diluents, glidants, preservatives, stabilizers, fillers, anti-adherents, coatings, and any other component known to one of ordinary skill in the art. Details for these components, i.e., potential identities and amounts, are the same as detailed above with respect to the first aspect of the invention.

A preferred embodiment of the third aspect of the invention is directed to a pharmaceutical composition comprising sodium lauryl sulfate and sodium bicarbonate. In a more preferred embodiment, the pharmaceutical composition comprising sodium lauryl sulfate and sodium bicarbonate comprises an immediate release layer containing substantially all of the naproxen. When present, sodium lauryl sulfate and sodium bicarbonate are typically used in a ratio of sodium lauryl sulfate:sodium bicarbonate preferably ranging from about 1:1 to about 1:10, more preferably from about 3:4 to about 3:25, still more preferably from about 2:5 to about 7:50, and most preferably is about 1:6. Sodium lauryl sulfate is typically present in an amount ranging from about 1 mg to about 50 mg, more preferably from about 3 mg to about 25 mg, still more preferably from about 5 mg to about 15 mg, and most preferably about 10 mg. Sodium bicarbonate is typically present in an amount ranging from about 25 mg to about 100 mg, more preferably from about 35 mg to about 80 mg, still more preferably from about 45 mg to about 75 mg, and most preferably about 60 mg.

Preferably the pharmaceutical composition of the third aspect is a tablet made using a wet granulation or a non-aqueous granulation. More preferably a non-aqueous granulation is used to make a tablet of the third aspect of the invention: most preferably the non-aqueous granulation is used to make an immediate release portion of a tablet pharmaceutical composition.

In traditional wet granulation, active ingredients and other components are combined, water is added, the wet mass is granulated using a suitable granulator, and then dried. In non-aqueous granulation, or hot-melt granulation, active ingredients and other components are combined, molten polymer is added as a binder, and the mass is granulated using a suitable granulator. Non-aqueous granulation is preferred herein since it involves fewer process steps and it reduces the amount of hydration, which has been found by the present inventors to negatively interfere with the dissolution and assay of the naproxen and to present processing issues, i.e., undesirable hard build-up of material on the granulator walls.

In further preferred embodiments of the third aspect of the invention, the molten polymer has a temperature ranging from about 50-80° C. since the melting point of guaifenesin is about 75-80°. Any way-type excipient or use material can be used as the molten binder. The wax material is used in an immediate release portion or layer only and has a use range of between 0 and 30% in the immediate release portion or layer. In a preferred embodiment, polyethylene glycol is used as the hot-melt polymer binder in the non-aqueous granulation; more preferably, any grade of high molecular weight polyethylene glycol that is solid or semi-solid at room temperature is used: most preferably, polyethylene glycol 4000 is used. Furthermore, the amount of polyethylene glycol used in the hot-melt granulation ranges from about 5% to about 30%, more preferably from about 10% to about 20%, still more preferably from about 10% to about 15%, and is most preferably about 12.5%, by weight of an immediate release portion. In other words, the ratio of polyethylene glycol to other components in an immediate release portion ranges from about 1:19 to about 3:7, more preferably from about 1:9 to about 1:4, still more preferably from about 1:9 to about 3:17, and is most preferably about 1:7. The amount of polyethylene glycol, then, in a pharmaceutical composition of the third aspect of the invention preferably ranges from about 1% to about 10%, more preferably from about 3% to about 8%, and most preferably from about 4% to about 6%, by weight of a pharmaceutical composition.

According to a preferred embodiment of the third aspect of the invention, less than 1% of particles comprising the immediate release portion have a particle size diameter of greater than 1000 μm.

When the hot-melt or non-aqueous granulation is used to make the pharmaceutical composition of the third aspect of the invention, additional binder materials may be used. Preferably these binders are selected from polyoxyl stearates, stearic acid, cetyl or stearyl alcohol, various waves, mono-di- and triglycerides, and combinations thereof.

As part of the hot-melt or non-aqueous granulation, it is possible to subdivide the granulation materials to add to the granulator in portions, to premix an active ingredient with certain excipients prior to adding them to the granulator (e.g., premixing naproxen with sodium bicarbonate and sodium lauryl sulfate), and to reserve a portion or all of certain excipients (e.g., microcrystalline cellulose, croscarmellose sodium and magnesium stearate) to add to the granulator after granules have been formed with the rest of the excipients and active ingredients. One of ordinary skill in the art will readily understand that additional steps such as screening and basing may also be used herein.

Embodiments according to the third aspect of the invention, not unlike embodiments of the first aspect of the invention, provide multi-symptom cough/cold/flu relief for a period of about 12 hours. In other words, the pharmaceutical compositions provide a therapeutic effect in respect of each active for a period of up to 12 hours.

A preferred embodiment of the pharmaceutical composition according to the third aspect may comprise:
(a) 55-65% guaifenesin;
(b) 1-5% dextromethorphan or a pharmaceutically acceptable salt thereof;
(c) 5-15% naproxen or a pharmaceutically acceptable salt thereof;
(d) 1-10% sustained release polymers;
(e) 0.1-10% binders;
(f) 0.1-10% disintegrants;
(g) 5-25% diluents; and
(h) up to 1% lubricants.

Another preferred embodiment of the composition according to the third aspect may comprise:
(a) 55-65% guaifenesin;
(b) 1-5% dextromethorphan or a pharmaceutically acceptable salt thereof;
(c) 5-15% naproxen or a pharmaceutically acceptable salt thereof;
(d) 1-8% hypromellose;
(e) 5-10% microcrystalline cellulose;
(f) 0.1-2% sodium lauryl sulphate;
(g) 1-10% sodium bicarbonate;
(h) 0.1-4.0% croscarmellose sodium;
(i) 0.1-10% polyethylene glycol 4000;
(j) 1-2% hydroxy ethyl cellulose; and
(k) 0.5-1% magnesium stearate.

Another preferred pharmaceutical composition may comprise:
(a) 58-63% guaifenesin;
(b) 2-3.5% dextromethorphan or a pharmaceutically acceptable salt thereof;
(c) 10-12% naproxen or a pharmaceutically acceptable salt thereof;
(d) 1-3% hypromellose;
(e) 5-8% microcrystalline cellulose;
(f) 1-2% hydroxyethyl cellulose;
(g) 0.5-2.5% croscarmellose sodium;
(h) 0.5-1.5% sodium lauryl sulphate;
(i) 5-8% sodium bicarbonate;
(j) 5-8% polyethylene glycol 4000; and
(k) 0.5-1% magnesium stearate.

A preferred composition for a sustained release portion of a pharmaceutical composition of the third aspect of the invention may comprise:
(a) 80-90% guaifenesin;
(b) 3-6% dextromethorphan or a pharmaceutically acceptable salt thereof;
(c) up to 5% hypromellose;
(d) up to 5% hydroxy ethylcellulose;
(e) up to 5% microcrystalline cellulose; and
(f) up to 1% magnesium stearate.

A preferred embodiment of the third aspect of the present invention is directed to a pharmaceutical composition comprising guaifenesin, naproxen and dextromethorphan and at least one pharmaceutically acceptable component, wherein about 100% of naproxen dissolves within 30 minutes in a pH 6.8 phosphate buffer. In another preferred embodiment, at least about 90% of naproxen dissolves within 20 minutes in a pH 6.8 phosphate buffer. A further preferred embodiment according to the third aspect is directed to a pharmaceutical composition having the noted dissolution properties and comprising:
(a) 58-63% guaifenesin;
(b) 2-3.5% dextromethorphan or a pharmaceutically acceptable salt thereof;
(c) 10-12% naproxen or a pharmaceutically acceptable salt thereof;
(d) 1-3% hypromellose;
(e) 5-8% microcrystalline cellulose;
(f) 1-2% hydroxyethyl cellulose;
(g) 0.5-2.5% croscarmellose sodium;
(h) 0.5-1.5% sodium lauryl sulfate;
(i) 5-8% sodium bicarbonate;
(j) 5-8% polyethylene glycol 4000; and
(k) 0.5-1% magnesium stearate.

A still further preferred embodiment is directed to a pharmaceutical composition having the noted dissolution properties and comprising the components noted in any of the below examples, e.g., Examples 9, 11, 13, etc.

Still another preferred embodiment of the third aspect of the invention is directed to a pharmaceutical composition comprising guaifenesin, naproxen and dextromethorphan and at least one pharmaceutically acceptable component, wherein the pharmaceutical composition provides a mean $C_{max}$ and at least one of a mean $AUC_{inf}$ and a mean $AUC_{0-12}$ for naproxen under fasted conditions based on single-dose administration that are from 80% to 125% of the mean $C_{max}$ and at least one of the mean $AUC_{inf}$ and the mean $AUC_{0-12}$ for naproxen provided by a pharmaceutical composition comprising (a) 58-63% guaifenesin; (b) 2-3.5% dextromethorphan or a pharmaceutically acceptable salt thereof; (c) 10-12% naproxen or a pharmaceutically acceptable salt thereof; (d) 1-3% hypromellose; (e) 5-8% microcrystalline cellulose; (f) 1-2% hydroxyethyl cellulose; (g) 0.5-2.5% croscarmellose sodium; (h) 0.5-1.5% sodium lauryl sulfate; (i) 5-8% sodium bicarbonate; (j) 5-8% polyethylene glycol 4000; and (k) 0.5-1% magnesium stearate. A further preferred embodiment is directed to the same pharmaceutical composition wherein the comparison is at a 90% confidence interval. A still further preferred embodiment is directed to a pharmaceutical composition having the noted mean $C_{max}$ and at least one of a mean $AUC_{inf}$ and a mean $AUC_{0-12}$ properties and comprising the components noted in any of the below examples, e.g., Examples 9, 11, 13, etc.

A fourth aspect of the present invention is directed to the non-aqueous granulation process described above with regard to the third aspect of the invention. More specifically, the fourth aspect is directed to a process of making a pharmaceutical composition comprising a pharmaceutically effective amount of each of guaifenesin, naproxen and dextromethorphan, said process comprising the step of hot-melt granulating a mixture of guaifenesin, naproxen, dextromethorphan and at least one pharmaceutically acceptable binder. Details regarding suitable binders, amounts of active ingredients, etc. are as set forth above with regard to the first and third aspects of the invention. The hot-melt granulation process preferably provides an immediate release portion containing naproxen of a pharmaceutical composition according to the third aspect.

According to a fifth aspect of the present invention, there is provided a method of providing relief from the symptoms of bronchial conditions, coughing and symptoms or diseases associated with coughing comprising administering to an individual a pharmaceutical composition as described in the first and third aspects of the invention set forth above. The preferred dosages are as follows: 220 mg naproxen, 60 mg dextromethorphan and 1200 mg guaifenesin. The dosage may be administered as one discrete pharmaceutical composition according to the invention, or more preferably is administered as more than one, most preferably two, discrete pharmaceutical compositions. In other words, the dosage may be administered as, for example, one tablet containing the entire dosage or as more than one tablet containing a portion of the entire dosage. In a most preferred embodiment, the entire dosage is administered in two tablets.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

As used herein, the term "consisting essentially of" means the composition contains the indicated components and may contain additional components provided that the additional components that are non-active and do not materially affect the composition's basic characteristics. As used herein, the term "consisting of" means the composition contains the only indicated components and excludes other components. The terms "composition" and "formulation" are used interchangeably throughout the present application.

For the avoidance of doubt when the composition of the present invention is in the form of a tablet or tablets, the values given for both the ranges and amounts of the components in the compositions of the present invention refer to uncoated tablets. Additional coatings can be added as required.

Various preferred embodiments of the present invention may be used in various combinations with other preferred embodiments of the invention except where stated otherwise and except where to do so would be inconsistent. For example, a preferred embodiment of the third aspect of the invention related to the inclusion of sodium lauryl sulfate and sodium bicarbonate can be combined with a preferred embodiment of the third aspect of the invention related to the inclusion of polyethylene glycol. Likewise a preferred embodiment of the first aspect of the invention may be combined with a preferred embodiment of the third aspect of the invention, etc.

Specific embodiments of the invention will now be demonstrated by reference to the following examples. It should be understood that these examples are disclosed solely by way of illustrating the invention and should not be taken in any way to limit the scope of the present invention.

Example 1

A pharmaceutical composition according to the present invention was made by inserting Tablet 1 and Tablet 2 below in a gelatin capsule which is then sealed. Tablets 1 and 2 were made according to a known wet granulation tableting method, i.e., excipients and actives were dry blended, water was added, and the mixture was granulated.

| Ingredient | mg/tablet | % Weight |
|---|---|---|
| Tablet 1: Naproxen | | |
| Naproxen Sodium | 110.0 | 73.33 |
| Microcrystalline Cellulose | 34.45 | 22.96 |
| Povidone | 4.50 | 3.0 |
| Mg Stearate | 1.05 | 0.7% |
| Total Tablet | 150.0 | 100.0 |
| Tablet 2: Immediate/Sustained Release Dextromethorphan and Guaifenesin | | |
| Guaifenesin | 600.0 | 76.41 |
| Hypromellose | 50.00 | 6.37 |
| MCC | 87.52 | 11.15 |
| Dextromethorphan HBr | 30.0 | 3.82 |
| Carbomer | 7.50 | 0.96 |
| Sodium Starch Glycolate | 3.98 | 0.51 |
| Colorant | 0.20 | 0.025 |
| Mg Stearate | 6.0 | 0.76 |
| Total Tablet | 785.2 | 100.0 |

Example 2

A pharmaceutical composition according to the present invention was made by inserting Tablet 1 and Tablet 2 below in a gelatin capsule which is then sealed. Tablets 1 and 2 were made according to a known wet granulation tableting method, i.e., excipients and actives were dry blended, water was added, and the mixture was granulated.

| Ingredient | mg/tablet | % Weight |
|---|---|---|
| Tablet 1: Naproxen | | |
| Naproxen Sodium | 110.0 | 51.16 |
| Microcrystalline Cellulose | 81.00 | 37.67 |
| Crospovidone | 7.50 | 3.49 |
| Croscarmellose sodium | 15.00 | 6.98 |
| Mg Stearate | 1.50 | 0.7 |
| Total Tablet | 215.0 | 100.0 |
| Tablet 2: Immediate/Sustained Release Dextromethorphan and Guaifenesin | | |
| Guaifenesin | 600.0 | 74.77 |
| Hypromellose | 19.00 | 2.37 |
| MCC | 129.40 | 16.12 |
| Dextromethorphan HBr | 30.0 | 3.74 |
| Povidone | 7.00 | 0.87 |
| Croscarmellose Sodium | 6.00 | 0.74 |
| Hydroxy ethyl cellulose | 9.00 | 1.12 |
| Colorant | 0.20 | 0.025 |
| Mg Stearate | 1.9 | 0.24 |
| Total Layer | 802.5 | 100.0 |

Example 3

A composite tablet according to the present invention was made having the below-listed components. Each layer was made according to a known wet granulation tableting method, i.e., excipients and actives were dry blended, water was added, and the mixture was granulated. The immediate release layer and the sustained release layer were combined by compression.

| Ingredient | mg/tablet | % Weight |
|---|---|---|
| Immediate Release Layer | | |
| Guaifenesin | 140 | 28.58 |
| Dextromethorphan HBr | 8 | 1.63 |
| Naproxen Sodium | 110 | 22.45 |
| Microcrystalline Cellulose | 60 | 12.24 |
| Povidone | 11 | 2.25 |
| Croscarmellose sodium | 26 | 5.31 |
| Crospovidone | 9.8 | 2.00 |
| Sodium lauryl sulfate | 25 | 5.10 |
| Bicarbonate | 100 | 20.41 |
| Mg Stearate | 0.1 | 0.02 |
| Total Tablet | 489.9 | 100.0 |
| Modified Release Layer | | |
| Guaifenesin | 460 | 84.73 |
| Dextromethorphan HBr | 22 | 4.05 |
| Hypromellose | 28 | 5.16 |
| Hydroxy ethyl cellulose | 14 | 2.58 |
| Microcrystalline Cellulose | 17 | 3.13 |
| Colorant | 0.1 | 0.02 |
| Mg Stearate | 1.8 | 0.33 |
| Total Layer | 542.9 | 100.0 |

Example 4

A composite tablet according to the present invention was made having the below-listed components. Each layer was made according to a known wet granulation tableting method, i.e., excipients and actives were dry blended, water was added, and the mixture was granulated. The immediate release layer and the sustained release layer were combined by compression.

| Ingredient | mg/tablet | % Weight |
|---|---|---|
| Immediate Release Layer | | |
| Guaifenesin | 200 | 45.25 |
| Dextromethorphan HBr | 10 | 2.26 |
| Naproxen Sodium | 110 | 24.89 |
| Microcrystalline Cellulose | 45 | 10.18 |
| Povidone | 11 | 2.49 |
| Crospovidone | 65 | 14.71 |
| Mg Stearate | 1 | 0.23 |
| Total Tablet | 442 | 100.0 |
| Modified Release Layer | | |
| Guaifenesin | 400 | 84.54 |
| Dextromethorphan HBr | 20 | 4.23 |
| Hypromellose | 24.5 | 5.18 |
| Hydroxy ethyl cellulose | 12.25 | 2.59 |
| Microcrystalline Cellulose | 14.75 | 3.12 |
| Colorant | 0.1 | 0.02 |
| Mg Stearate | 1.55 | 0.33 |
| Total Layer | 473.15 | 100.0 |

Example 5

A pharmaceutical composition according to the present invention was made by inserting Tablet 1 and Tablet 2 below in a gelatin capsule which is then sealed. Tablets 1 and 2 were made according to a known wet granulation tableting method, i.e., excipients and actives were dry blended, water was added, and the mixture was granulated. The immediate release layer and the sustained release layer were combined by compression.

| Ingredient | mg/tablet | % Weight |
|---|---|---|
| Tablet 1: Naproxen | | |
| Naproxen Sodium | 110.0 | 73.33 |
| Microcrystalline Cellulose | 14.55 | 9.7 |
| Lactose | 12.65 | 8.4 |
| Povidone | 4.65 | 3.1 |
| Croscarmellose sodium | 7.15 | 4.8 |
| Mg Stearate | 1 | 0.7 |
| Total Tablet | 150.0 | 100.0 |
| Tablet 2: Immediate/Sustained Release Dextromethorphan and Guaifenesin | | |
| Immediate Release Layer | | |
| Guaifenesin | 200 | 63.77 |
| Dextromethorphan HBr | 10 | 3.19 |
| Microcrystalline Cellulose | 85 | 27.10 |
| Povidone | 10 | 3.19 |
| Croscarmellose Sodium | 8.5 | 2.71 |
| Mg Stearate | 0.15 | 0.05 |
| Total Layer | 313.6 | 100.00 |
| Sustained Release Layer | | |
| Guaifenesin | 400 | 84.54 |
| Dextromethorphan HBr | 20 | 4.23 |
| Hypromellose (K100M) | 24.5 | 5.18 |
| Hydroxyethylcellulose | 12.25 | 2.59 |
| Microcrystalline Cellulose | 14.75 | 3.12 |
| Colorant | 0.1 | 0.02 |
| Mg Stearate | 1.55 | 0.33 |
| Total Layer | 473.15 | 100.0 |
| Total Tablet | 786.8 | 100.0 |

Example 6

A pharmaceutical composition according to the present invention was made by inserting Tablet 1 and Tablet 2 below in a gelatin capsule which is then sealed. Tablets 1 and 2 were made according to a known wet granulation tableting method, i.e., excipients and actives were dry blended, water was added, and the mixture was granulated. The immediate release layer and the sustained release layer were combined by compression.

| Ingredient | mg/tablet | % Weight |
|---|---|---|
| Tablet 1: Naproxen | | |
| Naproxen Sodium | 110 | 73.33 |
| Microcrystalline Cellulose | 6 | 4.00 |
| Lactose | 5 | 3.33 |
| Povidone | 3 | 2.00 |
| Sodium lauryl sulfate | 25 g | 16.67 |
| Mg Stearate | 1 | 0.67 |
| Total Tablet | 150.0 | 100.0 |
| Tablet 2: Immediate/ Sustained Release Dextromethorphan and Guaifenesin | | |
| Immediate Release Layer | | |
| Guaifenesin | 200 | 63.77 |
| Dextromethorphan HBr | 10 | 3.19 |
| Microcrystalline Cellulose | 85 | 27.10 |
| Povidone | 10 | 3.19 |
| Croscarmellose Sodium | 8.5 | 2.71 |
| Mg Stearate | 0.15 | 0.05 |
| Total Layer | 313.65 | 100.00 |

| Ingredient | mg/tablet | % Weight |
| --- | --- | --- |
| Sustained Release Layer | | |
| Guaifenesin | 400 | 84.54 |
| Dextromethorphan HBr | 20 | 4.23 |
| Hypromellose (K100M) | 24.5 | 5.18 |
| Hydroxyethylcellulose | 12.25 | 2.59 |
| Microcrystalline Cellulose | 14.75 | 3.12 |
| Colorant | 0.1 | 0.02 |
| Mg Stearate | 1.55 | 0.33 |
| Total Layer | 473.15 | 100.00 |
| Total Tablet | 786.8 | 100.0 |

Example 7

A pharmaceutical composition according to the present invention was made by inserting Tablet 1 and Tablet 2 below in a gelatin capsule which is then sealed. Tablets 1 and 2 were made according to a known wet granulation tableting method, i.e., excipients and actives were dry blended, water was added, and the mixture was granulated. The immediate release layer and the sustained release layer were combined by compression.

| Ingredient | mg/tablet | % Weight |
| --- | --- | --- |
| Tablet 1: Naproxen | | |
| Naproxen Sodium | 110.0 | 73.33 |
| Microcrystalline Cellulose | 14.55 | 9.7 |
| Lactose | 12.65 | 8.4 |
| Povidone | 4.65 | 3.1 |
| Croscarmellose sodium | 7.15 | 4.8 |
| Mg Stearate | 1 | 0.7 |
| Total Tablet | 150.0 | 100.0 |
| Tablet 2: Immediate/ Modified Release Dextromethorphan and Guaifenesin | | |
| Immediate Release Layer | | |
| Guaifenesin | 130 | 54.83 |
| Dextromethorphan HBr | 7.00 | 2.95 |
| Microcrystalline Cellulose | 85.00 | 35.85 |
| Povidone | 8.00 | 3.37 |
| Croscarmellose Sodium | 7.00 | 2.95 |
| Mg Stearate | 0.10 | 0.04 |
| Total Layer | 237.10 | 100.00 |
| Sustained Release Layer | | |
| Guaifenesin | 470 | 86.35 |
| Dextromethorphan HBr | 23 | 4.23 |
| Hypromellose (K100M) | 17 | 3.12 |
| Hydroxyethylcellulose | 17 | 3.12 |
| Microcrystalline Cellulose | 15.5 | 2.85 |
| Colorant | 0.1 | 0.02 |
| Mg Stearate | 1.7 | 0.31 |
| Total Layer | 544.3 | 100.00 |
| Total Tablet | 781.40 | 100.0 |

Example 8

A pharmaceutical composition according to the present invention was made by inserting Tablet 1 and Tablet 2 below in a gelatin capsule which is then sealed. Tablets 1 and 2 were made according to a known wet granulation tableting method, i.e., excipients and actives were dry blended, water was added, and the mixture was granulated. The immediate release layer and the sustained release layer were combined by compression.

| Ingredient | mg/tablet | % Weight |
| --- | --- | --- |
| Tablet 1: Naproxen | | |
| Naproxen Sodium | 110 | 73.33 |
| Microcrystalline Cellulose | 6 | 4.00 |
| Lactose | 5 | 3.33 |
| Povidone | 3 | 2.00 |
| Sodium lauryl sulfate | 25 | 16.67 |
| Mg Stearate | 1 | 0.67 |
| Total Tablet | 150.0 | 100.0 |
| Tablet 2: Immediate/ Sustained Release Dextromethorphan and Guaifenesin | | |
| Immediate Release Layer | | |
| Guaifenesin | 130 | 54.83 |
| Dextromethorphan HBr | 7.00 | 2.95 |
| Microcrystalline Cellulose | 85.00 | 35.85 |
| Povidone | 8.00 | 3.37 |
| Croscarmellose Sodium | 7.00 | 2.95 |
| Mg Stearate | 0.10 | 0.04 |
| Total Layer | 237.10 | 100.00 |
| Sustained Release Layer | | |
| Guaifenesin | 470 | 86.35 |
| Dextromethorphan HBr | 23 | 4.23 |
| Hypromellose (K100M) | 17 | 3.12 |
| Hydroxyethylcellulose | 17 | 3.12 |
| Microcrystalline Cellulose | 15.5 | 2.85 |
| Colorant | 0.1 | 0.02 |
| Mg Stearate | 1.7 | 0.31 |
| Total Layer | 544.3 | 100.00 |
| Total Tablet | 781.40 | 100.0 |

Example 9

A composite tablet according to the present invention was made having the below-listed components. The immediate release layer was made according to the hot-melt granulation method described herein, and the sustained release layer was made according to a known wet granulation tableting method, i.e., excipients and actives were dry blended, water was added, and the mixture was granulated. The immediate release layer and the sustained release layer were combined by compression.

| Ingredient | mg/tablet | % Weight |
| --- | --- | --- |
| Immediate Release Layer | | |
| Guaifenesin | 100 | 24.30429 |
| Dextromethorphan HBr | 8 | 1.944343 |
| Naproxen Sodium | 110 | 26.73472 |
| Microcrystalline Cellulose | 45 | 10.93693 |
| Croscarmellose sodium | 23 | 5.589987 |
| Sodium lauryl sulfate | 10 | 2.430429 |
| Sodium bicarbonate | 60 | 14.58257 |
| Polyethylene glycol 4000 | 51.45 | 12.50456 |
| Mg Stearate | 4 | 0.972172 |
| Total Tablet | 411.45 | 100.0 |

| Ingredient | mg/tablet | % Weight |
|---|---|---|
| Sustained Release Layer | | |
| Guaifenesin | 500 | 85.77653 |
| Dextromethorphan HBr | 22 | 3.774168 |
| Hypromellose | 28 | 4.803486 |
| Hydroxy ethyl cellulose | 14 | 2.401743 |
| Microcrystalline Cellulose | 16.29 | 2.7946 |
| Colorant | 0.82 | 0.140674 |
| Mg Stearate | 1.8 | 0.308796 |
| Total Layer | 582.91 | 100.0 |

Example 10

A composite tablet according to the present invention was made having the below-listed components. The immediate release layer was made according to the hot-melt granulation method described herein, and the sustained release layer was made according to a known wet granulation tableting method, i.e., excipients and actives were dry blended, water was added, and the mixture was granulated. The immediate release layer and the sustained release layer were combined by compression.

| Ingredient | mg/tablet | % Weight |
|---|---|---|
| Immediate Release Layer | | |
| Guaifenesin | 100 | 24.30429 |
| Dextromethorphan HBr | 8 | 1.94434 |
| Naproxen Sodium | 110 | 26.73472 |
| Microcrystalline Cellulose | 45 | 10.93693 |
| Croscarmellose sodium | 23 | 5.58999 |
| Sodium lauryl sulfate | 10 | 2.43043 |
| Sodium bicarbonate | 60 | 14.58257 |
| Polyethylene glycol 4000 | 51.45 | 12.50456 |
| Mg Stearate | 4 | 0.97217 |
| Total Tablet | 411.45 | 100.0 |
| Sustained Release Layer | | |
| Guaifenesin | 505 | 89.3489 |
| Dextromethorphan HBr | 22.5 | 3.98089 |
| Methocel E10 | 25 | 4.42322 |
| Carbomer Homopolymer Type B NF | 7.5 | 1.32696 |
| Colorant | 0.2 | 0.03539 |
| Mg Stearate | 5 | 0.88464 |
| Total Layer | 565.2 | 100.0 |

Example 11

A composite tablet according to the present invention was made having the below-listed components in a scaled-up manufacture. The immediate release layer was made according to the hot-melt granulation method described herein, and the sustained release layer was made according to a known wet granulation tableting method, i.e., excipients and actives were dry blended, water was added, and the mixture was granulated. The immediate release layer and the sustained release layer were combined by compression.

| Ingredient | mg/tablet | % Weight |
|---|---|---|
| Immediate Release Layer | | |
| Guaifenesin | 100 | 24.30429 |
| Dextromethorphan HBr | 8 | 1.944343 |
| Naproxen Sodium | 110 | 26.73472 |
| Microcrystalline Cellulose | 45 | 10.93693 |
| Croscarmellose sodium | 23 | 5.58999 |
| Sodium lauryl sulfate | 10 | 2.43043 |
| Sodium bicarbonate | 60 | 14.58257 |
| Polyethylene glycol 4000 | 51.45 | 12.50456 |
| Mg Stearate | 4 | 0.97217 |
| Total Tablet | 411.45 | 100.0 |
| Sustained Release Layer | | |
| Guaifenesin | 500 | 85.77653 |
| Dextromethorphan HBr | 22 | 3.774168 |
| Hypromellose | 28 | 4.803486 |
| Hydroxy ethyl cellulose | 14 | 2.401743 |
| Microcrystalline Cellulose | 16.29 | 2.7946 |
| Colorant | 0.82 | 0.140674 |
| Mg Stearate | 1.8 | 0.308796 |
| Total Layer | 582.91 | 100.0 |

Example 12

A pharmaceutical composition according to the present invention was made by inserting Tablet 1 and Tablet 2 below in a gelatin capsule which is then sealed. Tablets 1 and 2 were made according to a known wet granulation tableting method, i.e., excipients and actives were dry blended, water was added, and the mixture was granulated. The immediate release layer and the sustained release layer were combined by compression.

| Ingredient | mg/tablet |
|---|---|
| Tablet 1: Naproxen | |
| Naproxen Sodium | 110 |
| Microcrystalline Cellulose | 81 |
| Povidone | 7.50 |
| Croscarmellose sodium | 15 |
| Magnesium stearate | 1.50 |
| Total Tablet | 215.0 |
| Tablet 2: Immediate/Sustained Release Dextromethorphan and Guaifenesin Immediate Release Layer | |
| Guaifenesin | 70.00 |
| Dextromethorphan HBr | 4.50 |
| Microcrystalline Cellulose | 112.40 |
| Povidone | 7.00 |
| Croscarmellose Sodium | 6.00 |
| Mg Stearate | 0.10 |
| Total Layer | 200.00 |
| Sustained Release Layer | |
| Guaifenesin | 530 |
| Dextromethorphan HBr | 25.5 |
| Hypromellose (K100M) | 19.00 |
| Hydroxyethylcellulose | 9.0 |
| Microcrystalline Cellulose | 17.0 |
| Colorant | 0.20 |
| Mg Stearate | 1.8 |
| Total Layer | 602.5 |

Example 13

A composite tablet according to the present invention was made having the below-listed components. The immediate release layer was made according to the hot-melt granulation method described herein, and the sustained release layer was made according to a known wet granulation tableting method, i.e., excipients and actives were dry blended, water was added, and the mixture was granulated. The immediate release layer and the sustained release layer were combined by compression.

| Ingredient | mg/tablet | % Weight |
|---|---|---|
| Immediate Release Layer | | |
| Guaifenesin | 100 | 24.30429 |
| Dextromethorphan HBr | 8 | 1.944343 |
| Naproxen Sodium | 110 | 26.73472 |
| Microcrystalline Cellulose | 45 | 10.93693 |
| Croscarmellose sodium | 23 | 5.589987 |
| Sodium lauryl sulfate | 10 | 2.430429 |
| Sodium bicarbonate | 60 | 14.58257 |
| Polyethylene glycol 4000 | 51.45 | 12.50456 |
| Mg Stearate | 4 | 0.972172 |
| Total Tablet | 411.45 | 100.0 |
| Sustained Release Layer | | |
| Guaifenesin | 500 | 85.77653 |
| Dextromethorphan HBr | 22 | 3.774168 |
| Hypromellose | 18 | 3.17511 |
| Hydroxy ethyl cellulose | 8 | 1.41116 |
| Microcrystalline Cellulose | 16.29 | 2.7946 |
| Colorant | 0.82 | 0.140674 |
| Mg Stearate | 1.8 | 0.308796 |
| Total Layer | 566.91 | 100.0 |

Example 14

An immediate release layer for a composite tablet according to the present invention was made according to a known wet granulation tableting method, i.e., excipients and actives were dry blended, water was added, and the mixture was granulated. The immediate release layer can be combined with a suitable sustained release layer by compression.

| Ingredient | mg/tablet |
|---|---|
| Guaifenesin | 100.00 |
| Dextromethorphan HBr | 8.00 |
| Naproxen Sodium | 110.00 |
| Microcrystalline Cellulose | 45.00 |
| Croscarmellose sodium | 23.00 |
| Povidone | 11.00 |
| Sodium lauryl sulfate | 10.00 |
| Sodium bicarbonate | 30.00 |
| Mg Stearate | 4.00 |
| Total Tablet | 371.00 |

The naproxen, sodium lauryl sulfate and sodium bicarbonate were separately pre-blended.

Example 15

An immediate release layer for a composite tablet according to the present invention was made according to a known wet granulation tableting method, i.e., excipients and actives were dry blended, water was added, and the mixture was granulated. The immediate release layer can be combined with a suitable sustained release layer by compression.

| Ingredient | mg/tablet | % Weight |
|---|---|---|
| Guaifenesin | 100.00 | 60.60606 |
| Dextromethorphan HBr | 8.00 | 4.84848 |
| Microcrystalline Cellulose | 30.00 | 18.18182 |
| Croscarmellose sodium | 15.00 | 9.09091 |
| Povidone | 12.00 | 7.27273 |
| Total | 165.00 | 100.00 |

The above ingredients were dry blended and then dry blended with the diluent microcrystalline cellulose and the disintegrant croscarmellose sodium and with a further wet granulation having the following components:

| Ingredient | mg/tablet | % Weight |
|---|---|---|
| Naproxen sodium | 110.00 | 51.76471 |
| Microcrystalline Cellulose | 25.00 | 11.76471 |
| Povidone | 7.50 | 3.52941 |
| Sodium lauryl sulfate | 10.00 | 4.70588 |
| Sodium bicarbonate | 60.00 | 28.23529 |
| Total | 212.50 | 100.00 |
| Croscarmellose Sodium | 10.50 | 36.842105 |
| Microcrystalline Cellulose | 18.00 | 63.157895 |

The above dry blended wet granulations with diluent and disintegrant are then dry blended with the lubricant Magnesium stearate to yield a total formula:

| Ingredient | mg/tablet | % Weight |
|---|---|---|
| Guaifenesin | 100.00 | 24.39024 |
| Dextromethorphan HBr | 8.00 | 1.95122 |
| Naproxen Sodium | 110.00 | 26.82927 |
| Microcrystalline Cellulose | 62.00 | 15.12196 |
| Croscarmellose sodium | 36.50 | 8.90244 |
| Povidone | 19.50 | 4.75610 |
| Sodium Bicarbonate | 60.00 | 14.63415 |
| Sodium Lauryl Sulfate | 10.00 | 2.43902 |
| Magnesium Stearate | 4.00 | 0.97561 |
| Total Tablet | 410.00 | |

Example 16

An immediate release layer for a composite tablet according to the present invention was made according to the hot-melt granulation method described herein. The immediate release layer can be combined with a suitable sustained release layer by compression.

| Ingredient | mg/tablet | % Weight |
|---|---|---|
| Guaifenesin | 100.00 | 22.91 |
| Dextromethorphan HBr | 8.00 | 1.83 |
| Naproxen Sodium | 110.00 | 25.20 |
| Microcrystalline Cellulose | 45.00 | 10.31 |
| Croscarmellose sodium | 34.00 | 7.79 |
| Sodium lauryl sulfate | 10.00 | 2.29 |
| Sodium bicarbonate | 60.00 | 13.75 |

| Ingredient | mg/tablet | % Weight |
| --- | --- | --- |
| Polyethylene glycol 4000 | 65.45 | 15.00 |
| Mg Stearate | 4.00 | 0.92 |
| Total Tablet | 436.45 | 100.0 |

Example 17

An immediate release layer for a composite tablet according to the present invention was made according to the hot-melt granulation method described herein. The immediate release layer can be combined with a suitable sustained release layer by compression.

| Ingredient | mg/tablet | % Weight |
| --- | --- | --- |
| Guaifenesin | 100.00 | 23.61 |
| Dextromethorphan HBr | 8.00 | 1.89 |
| Naproxen Sodium | 110.00 | 25.97 |
| Microcrystalline Cellulose | 45.00 | 10.62 |
| Croscarmellose sodium | 23.00 | 5.43 |
| Sodium lauryl sulfate | 10.00 | 2.36 |
| Sodium bicarbonate | 60.00 | 14.17 |
| Polyethylene glycol 4000 | 63.55 | 15.00 |
| Mg Stearate | 4.00 | 0.94 |
| Total Tablet | 423.55 | 100.0 |

Example 18

An immediate release layer for a composite tablet according to the present invention was made according to the hot-melt granulation method described herein. The immediate release layer can be combined with a suitable sustained release layer by compression.

| Ingredient | mg/tablet | % Weight |
| --- | --- | --- |
| Guaifenesin | 100.00 | 25.60623 |
| Naproxen Sodium | 110.00 | 28.16685 |
| Dextromethorphan HBr | 8.00 | 2.04850 |
| Microcrystalline Cellulose | 45.00 | 11.52280 |
| Croscarmellose sodium | 23.00 | 5.88943 |
| Povidone | 11.00 | 2.81669 |
| Sodium Lauryl Sulfate | 10.00 | 2.56062 |
| Sodium bicarbonate | 60.00 | 15.36374 |
| Polyethylene glycol 4000 | 19.51 | 5.00090 |
| Mg Stearate | 4.00 | 1.02425 |
| Total Tablet | 390.51 | 100 |

Example 19

An immediate release layer for a composite tablet according to the present invention was made according to the hot-melt granulation method described herein. The immediate release layer can be combined with a suitable sustained release layer by compression.

| Ingredient | mg/tablet | % Weight |
| --- | --- | --- |
| Guaifenesin | 100.00 | 24.25830 |
| Naproxen Sodium | 110.00 | 26.68413 |
| Dextromethorphan HBr | 8.00 | 1.94066 |
| Microcrystalline Cellulose | 45.00 | 10.91624 |
| Croscarmellose sodium | 23.00 | 5.57941 |
| Povidone | 11.00 | 2.66841 |
| Sodium Lauryl Sulfate | 10.00 | 2.42583 |
| Sodium bicarbonate | 60.00 | 14.55498 |
| Polyethylene glycol 4000 | 41.23 | 10.00170 |
| Mg Stearate | 4.00 | 0.97033 |
| Total Tablet | 412.23 | 100 |

Example 20

An immediate release layer for a composite tablet according to the present invention was made according to the hot-melt granulation method described herein. The immediate release layer can be combined with a suitable sustained release layer by compression.

| Ingredient | mg/tablet | % Weight |
| --- | --- | --- |
| Guaifenesin | 100.00 | 22.25140 |
| Naproxen Sodium | 110.00 | 24.47654 |
| Dextromethorphan HBr | 8.00 | 1.78011 |
| Microcrystalline Cellulose | 45.00 | 10.01313 |
| Croscarmellose sodium | 34.00 | 7.56547 |
| Sodium lauryl sulfate | 10.00 | 2.22514 |
| Sodium bicarbonate | 60.00 | 13.35084 |
| Polyethylene glycol 4000 | 67.41 | 14.99967 |
| Mg Stearate | 4.00 | 0.89006 |
| Total Tablet | 436.47 | 100.00 |

Example 21

An immediate release layer for a composite tablet according to the present invention was made according to the hot-melt granulation method described herein. The immediate release layer can be combined with a suitable sustained release layer by compression.

| Ingredient | mg/tablet | % Weight |
| --- | --- | --- |
| Guaifenesin | 100.00 | 23.61108 |
| Naproxen Sodium | 110.00 | 25.97219 |
| Dextromethorphan HBr | 8.00 | 1.88889 |
| Microcrystalline Cellulose | 45.00 | 10.62499 |
| Croscarmellose sodium | 23.00 | 5.43055 |
| Sodium Lauryl Sulfate | 11.00 | 2.36111 |
| Sodium bicarbonate | 60.00 | 14.16665 |
| Polyethylene Glycol 6000 | 63.55 | 15.00012 |
| Mg Stearate | 4.00 | 0.94444 |
| Total Tablet | 423.55 | 100.00 |

Example 22

An immediate release layer for a composite tablet according to the present invention was made according to the hot-melt granulation method described herein. The immediate release layer can be combined with a suitable sustained release layer by compression.

| Ingredient | mg/tablet | % Weight |
|---|---|---|
| Guaifenesin | 100.00 | 23.61108 |
| Naproxen Sodium | 110.00 | 25.97219 |
| Dextromethorphan HBr | 8.00 | 1.88889 |
| Microcrystalline Cellulose | 45.00 | 10.62499 |
| Croscarmellose sodium | 23.00 | 5.43055 |
| Sodium Lauryl Sulfate | 11.00 | 2.36111 |
| Sodium bicarbonate | 60.00 | 14.16665 |
| Polyethylene Glycol 3350 | 63.55 | 15.00012 |
| Mg Stearate | 4.00 | 0.94444 |
| Total Tablet | 423.55 | 100.00 |

Example 23

A composite tablet according to the present invention was made having the below-listed components. Each layer was made according to a known wet granulation tableting method, i.e., excipients and actives were dry blended, water was added, and the mixture was granulated. The immediate release layer and the sustained release layer were combined by compression.

| Ingredient | mg/tablet | % Weight |
|---|---|---|
| Immediate Release Layer | | |
| Guaifenesin | 100 | 26.95418 |
| Dextromethorphan HBr | 8 | 2.15633 |
| Naproxen Sodium | 110 | 29.64960 |
| Microcrystalline Cellulose | 45 | 12.12938 |
| Povidone | 11 | 2.96496 |
| Croscarmellose sodium | 23 | 6.19946 |
| Sodium lauryl sulfate | 10 | 2.69542 |
| Sodium bicarbonate | 60 | 16.17251 |
| Mg Stearate | 4 | 1.07817 |
| Total Tablet | 371 | 100.0 |
| Modified Release Layer | | |
| Guaifenesin | 500 | 85.7780 |
| Dextromethorphan HBr | 22 | 3.7742 |
| Hypromellose | 28 | 4.8036 |
| Hydroxy ethyl cellulose | 14 | 2.4018 |
| Microcrystalline Cellulose | 16.29 | 2.7946 |
| Colorant | 0.81 | 0.1390 |
| Mg Stearate | 1.8 | 0.3088 |
| Total Layer | 582.9 | 100.0 |

TESTING

Dissolution Testing

Dissolution tests for each of guaifenesin, naproxen and dextromethorphan were run at pH 5.0 and 6.8 for each of Examples 12, 9 and 11. The same dissolution test was run for commercially available Aleve® containing naproxen. Dissolution testing at pH 6.8 was performed for Mucinex® DM containing guaifenesin and dextromethorphan HBr. Dissolution tests for the immediate release layers of Examples 12, 16, and 23 were also run. The results are shown in FIGS. 1-4 and 8-12 and in Tables 1-14 below.

Test Method D8247706 [2.0]
    Dissolution Medium, also used as diluent—50 Mm Phosphate Buffer, pH6.8
    Mobile Phase: A—0.1% $H_3PO_4$ in Water
        B—0.1% $H_3PO_4$ in Methanol
    Stock Solution: Dextromethorphan HBr—0.425 mg/Ml
    Naproxen Sodium—1 mg/mL

TABLE 1

Dissolution at pH 5.0 for Example 12.

| | Time (min) | | | | |
|---|---|---|---|---|---|
| | 0 | 60 | 120 | 360 | 720 |
| Guaifenesin | 0 | 38.92 | 54.72 | 86.05 | 102.14 |
| Dextromethorphan | 0 | 46.75 | 64.28 | 95.76 | 107.79 |
| Naproxen | 0 | 99.66 | 101.23 | 101.4 | 102.28 |

TABLE 2

Dissolution at pH 5.0 for Example 9.

| | Time (min) | | | | |
|---|---|---|---|---|---|
| | 0 | 60 | 120 | 360 | 720 |
| Guaifenesin | 0 | 35.12 | 49.11 | 78.6 | 98.13 |
| Dextromethorphan | 0 | 41.6 | 56.11 | 83.34 | 98.33 |
| Naproxen | 0 | 94.42 | 101.48 | 102.75 | 103.26 |

TABLE 3

Dissolution at pH 5.0 for Example 11.

| | Time (min) | | | | |
|---|---|---|---|---|---|
| | 0 | 60 | 120 | 360 | 720 |
| Guaifenesin | 0 | 38.5 | 50.5 | 78.8 | 97.4 |
| Dextromethorphan | 0 | 48.1 | 59.9 | 84.5 | 99.5 |
| Naproxen | 0 | 102.1 | 103.6 | 103.8 | 104.2 |

TABLE 4

Dissolution at pH 6.8 for Example 12.

| | Time (min) | | | | |
|---|---|---|---|---|---|
| | 0 | 60 | 120 | 360 | 720 |
| Guaifenesin | 0 | 35.33333 | 48.66667 | 79.83333 | 97.83333 |
| Dextromethorphan | 0 | 38.666667 | 51.83333 | 81.5 | 97.33333 |
| Naproxen | 0 | 97 | 97.66667 | 97.66667 | 98.16667 |

TABLE 5

Dissolution at pH 6.8 for Example 9.

| | Time (min) | | | | |
|---|---|---|---|---|---|
| | 0 | 60 | 120 | 360 | 720 |
| Guaifenesin | 0 | 39.59125 | 52.145 | 80.46625 | 97.27625 |
| Dextromethorphan | 0 | 46.8 | 58.6175 | 84.12 | 97.3025 |
| Naproxen | 0 | 98.47 | 98.88175 | 97.935 | 98.7225 |

TABLE 6

Dissolution at pH 6.8 for Example 11.

| | | | | | | | | | |
|---|---|---|---|---|---|---|---|---|---|
| Time (min) | 0 | 10 | 20 | 30 | 45 | 60 | 120 | 360 | 720 |
| Guaifenesin | 0 | 16.7 | 24.6 | 29.4 | 34.1 | 38.1 | 50.5 | 79.2 | 96.4 |

TABLE 6-continued

Dissolution at pH 6.8 for Example 11.

| | | | | | | | | |
|---|---|---|---|---|---|---|---|---|
| Dextromethorphan | 0 | 20 | 29.7 | 34.9 | 40 | 43.8 | 55.8 | 81.7 | 94.4 |
| Naproxen | 0 | 58.8 | 91.8 | 100.7 | 102.2 | 102.4 | 102.7 | 103 | 103.3 |

TABLE 7

Dissolution at pH 6.8 for Aleve ®

| Time (min) | 0 | 10 | 20 | 30 | 45 | 60 |
|---|---|---|---|---|---|---|
| Naproxen | 0 | 81.19 | 93.92667 | 93.55 | 93.60333 | 93.9 |

TABLE 8

Dissolution at pH 5.0 for Aleve ®

| Time (min) | 0 | 10 | 20 | 30 | 45 | 60 |
|---|---|---|---|---|---|---|
| Naproxen | 0 | 16.6 | 33.6 | 42.7 | 51.4 | 58.5 |

TABLE 9

Dissolution at pH 6.8 for Example 23.

| Time (min) | 0 | 10 | 20 | 30 | 45 | 60 |
|---|---|---|---|---|---|---|
| Naproxen | 0 | 75 | 90 | 95 | 97 | 98 |

TABLE 10

Dissolution Data at pH 6.8 for Example 16 (immediate release layer only).

| Time (min) | 0 | 10 | 20 | 30 | 45 | 60 |
|---|---|---|---|---|---|---|
| Guaifenesin | 0 | 46.4 | 75.9 | 92.7 | 99.1 | 100.4 |
| Dextromethorphan | 0 | 40.0 | 65.7 | 86.5 | 93.5 | 94.4 |
| Naproxen | 0 | 48.4 | 75.6 | 92.7 | 99.0 | 99.6 |

TABLE 11

Dissolution Data at pH 5.0 for Example 16 (immediate release layer only).

| Time (min) | 0 | 10 | 20 | 30 | 45 | 60 |
|---|---|---|---|---|---|---|
| Guaifenesin | 0 | 49.0 | 79.6 | 96.9 | 101.3 | 101.0 |
| Dextromethorphan | 0 | 22.2 | 39.6 | 56.8 | 102.5 | 103.2 |
| Naproxen | 0 | 42.2 | 70.7 | 77.4 | 75.9 | 76.9 |

TABLE 12

Dissolution Data at pH 6.8 for Example 11 (immediate release layer only).

| Time (min) | 0 | 10 | 20 | 30 | 45 | 60 |
|---|---|---|---|---|---|---|
| Guaifenesin | 0 | 58.8 | 88.8 | 102.2 | 102.4 | 101.8 |
| Dextromethorphan | 0 | 54.3 | 79 | 88.3 | 92.9 | 91.3 |
| Naproxen | 0 | 57.3 | 84.9 | 96.7 | 96.9 | 96.5 |

TABLE 13

Dissolution Data at pH 5.0 for Example 11 (immediate release layer only).

| Time (min) | 0 | 10 | 20 | 30 | 45 | 60 |
|---|---|---|---|---|---|---|
| Guaifenesin | 0 | 66.4 | 92.6 | 96.8 | 97.7 | 97.2 |
| Dextromethorphan | 0 | 57.4 | 83.1 | 91 | 93.3 | 93.3 |
| Naproxen | 0 | 57.3 | 84.9 | 96.7 | 96.9 | 96.5 |

TABLE 14

Dissolution at pH 6.8 for Mucinex ® DM.

| Time (min) | 0 | 10 | 20 | 30 | 45 | 60 | 120 | 360 | 720 |
|---|---|---|---|---|---|---|---|---|---|
| Guaifenesin | 0 | 23.66667 | 29 | 35.16667 | 40.33333 | 43.83333 | 54.16667 | 78.33333 | 95.83333 |
| Dextromethorphan | 0 | 17.66667 | 22.33333 | 27.83333 | 33 | 36.5 | 47.83333 | 75.33333 | 95 |

Figure 5:
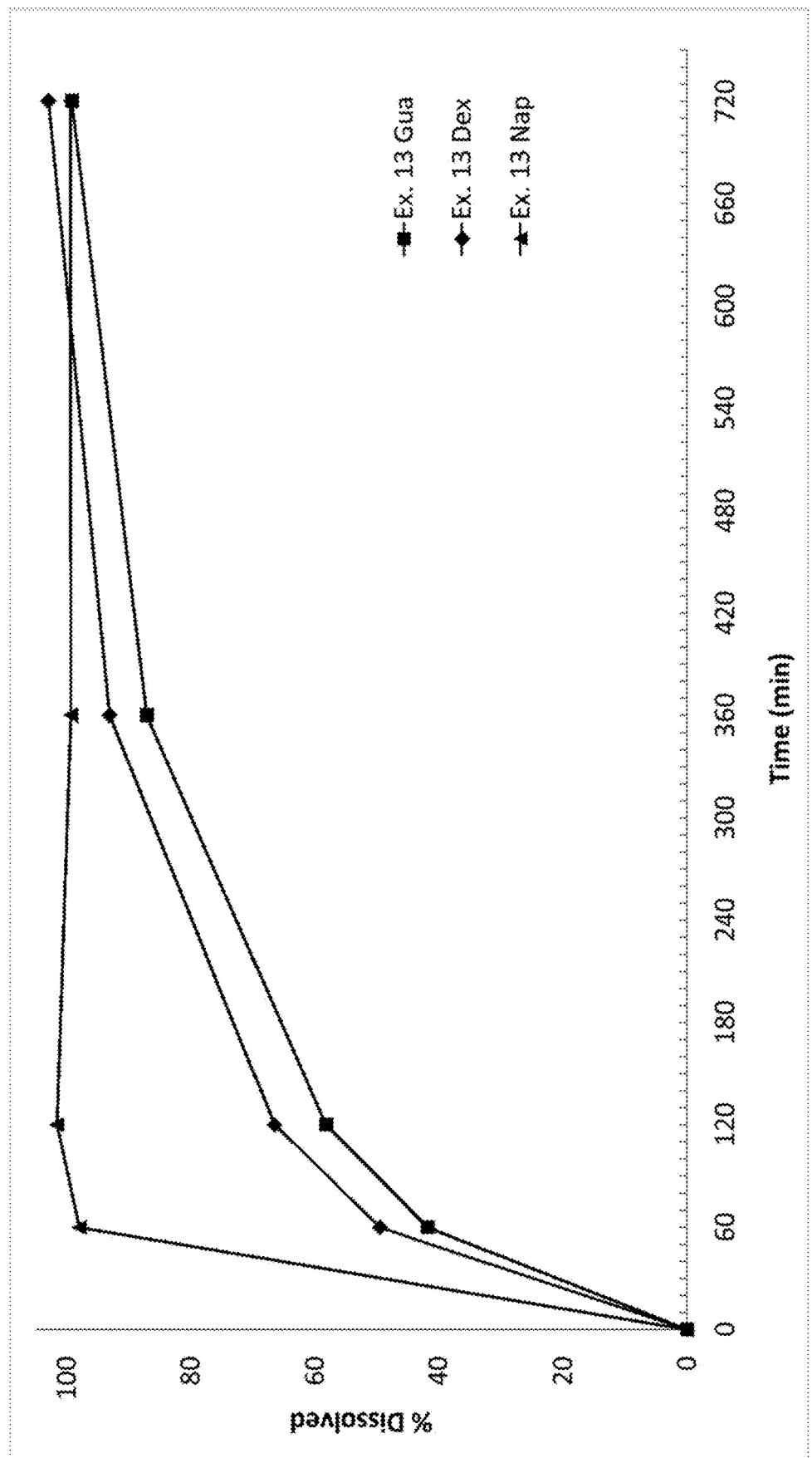
FIG. 5 shows dextromethorphan, guaifenesin and naproxen dissolution results at pH 6.8 for an embodiment of the present invention.

Dissolution tests for each of guaifenesin, naproxen and dextromethorphan were run at pH 6.8 for Example 13. The results are shown in FIG. 5 and in Table 15 below.

Test Method D8247706 [2.0]
  Dissolution Medium, also used as diluent—50 Mm Phosphate Buffer, pH6.8
  Mobile Phase: A—0.1% $H_3PO_4$ in Water
  B—0.1% $H_3PO_4$ in Methanol
  Stock Solution: Dextromethorphan HBr—0.425 mg/Ml
  Naproxen Sodium—1 mg/mL

TABLE 15

Dissolution at pH 6.8 for Example 13.

| | | Time (min) | | | |
|---|---|---|---|---|---|
| | 0 | 60 | 120 | 360 | 720 |
| Guaifenesin | 0 | 41.71 | 58.25 | 87.14 | 99.23 |
| Dextromethorphan | 0 | 49.5 | 66.55 | 93.09 | 102.93 |
| Naproxen | 0 | 97.91 | 101.54 | 99.32 | 99.41 |

Figure 13:
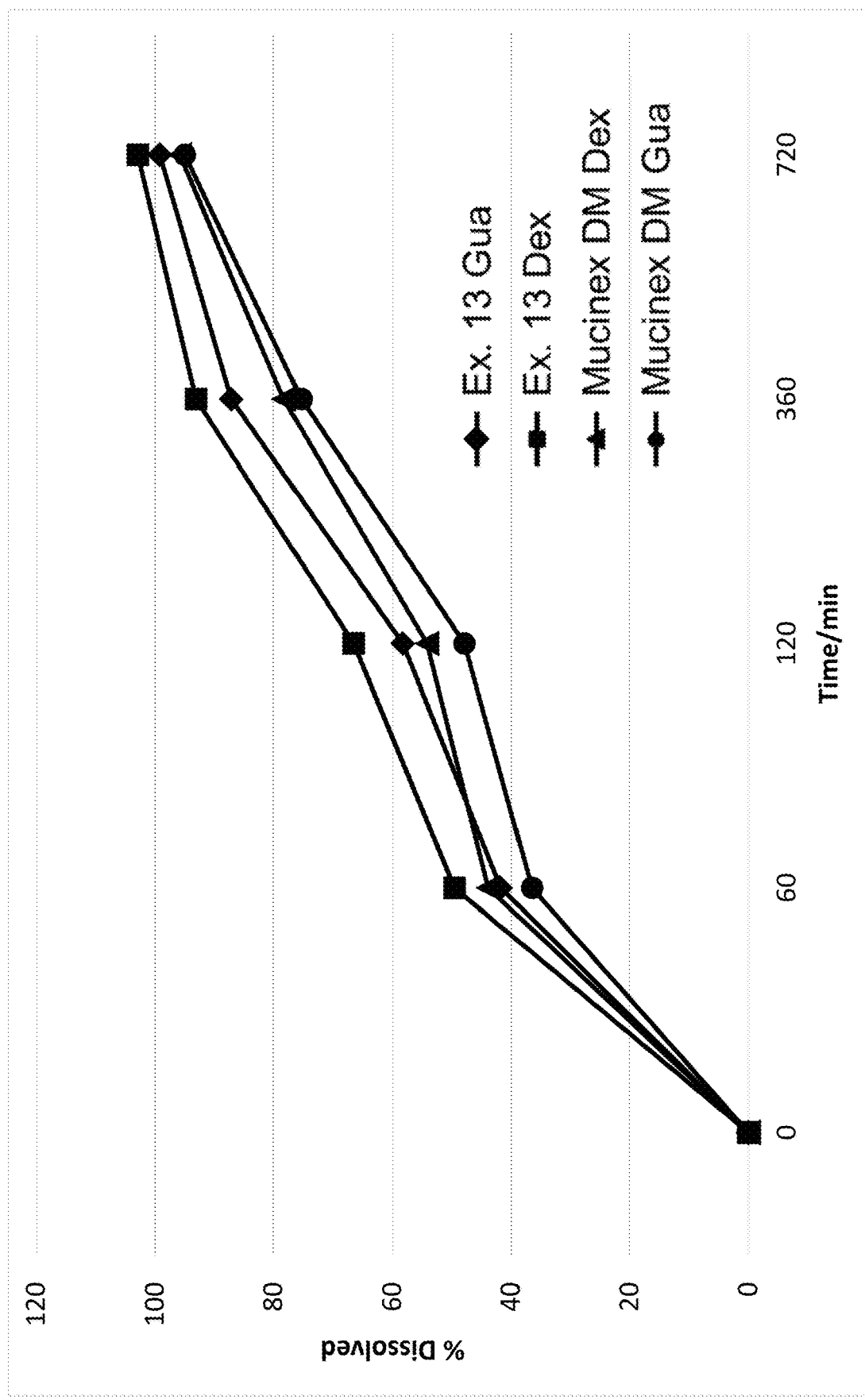
FIG. 13 shows guaifenesin and dextromethorphan dissolution results at pH 6.8 (simulated fasted state) for an embodiment of the present invention as well as commercially available Mucinex® DM.

Dissolution results for Example 13 found to release expectorant and antitussive quicker than current marketed product (Table 14) due to decrease in polymeric content (FIG. 13).

Figure 7:
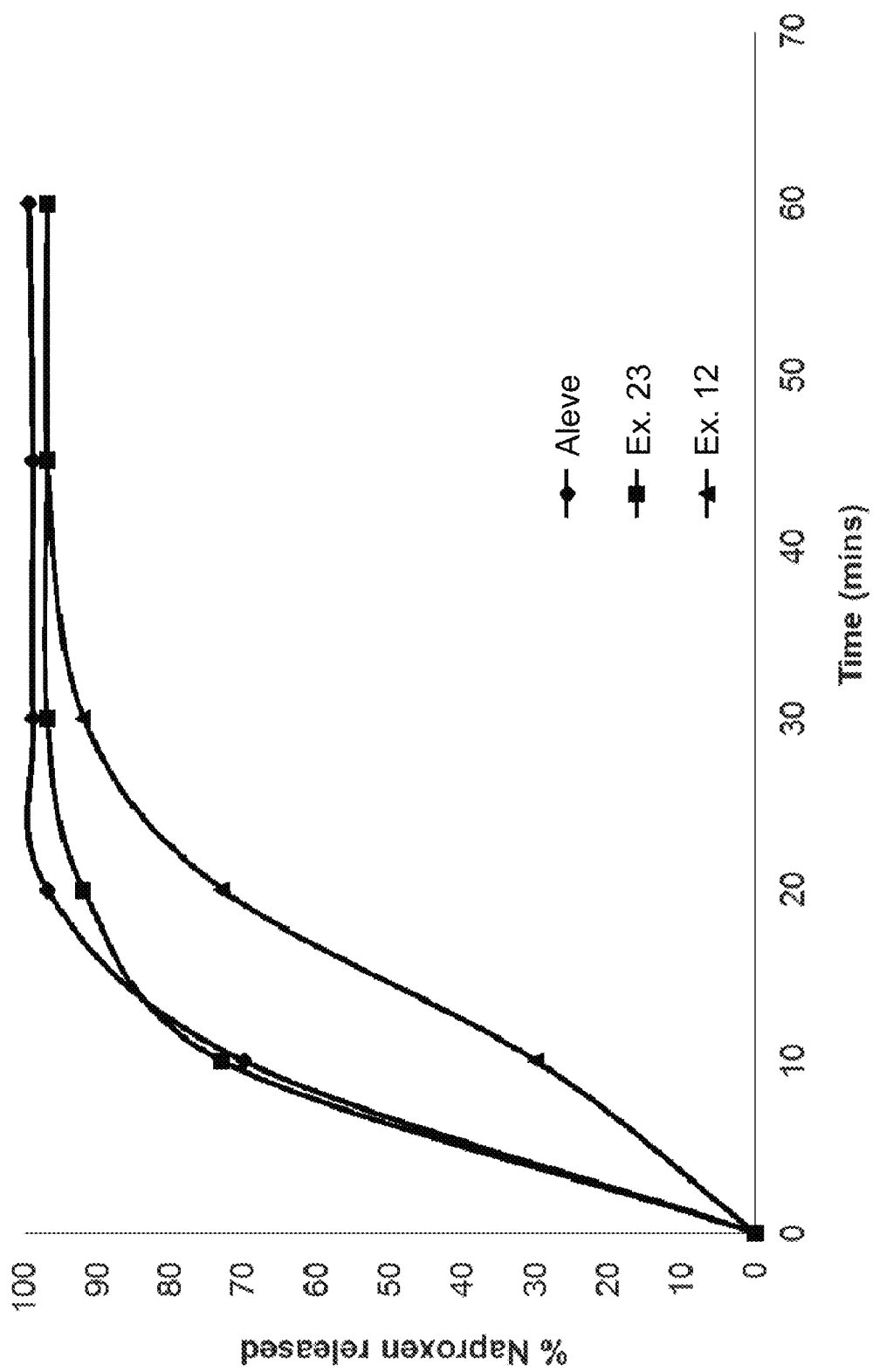
FIG. 7 shows naproxen dissolution results at pH 6.8 (simulated fasted state) for embodiments of the present invention as well as commercially available Aleve®.
Figure 8:
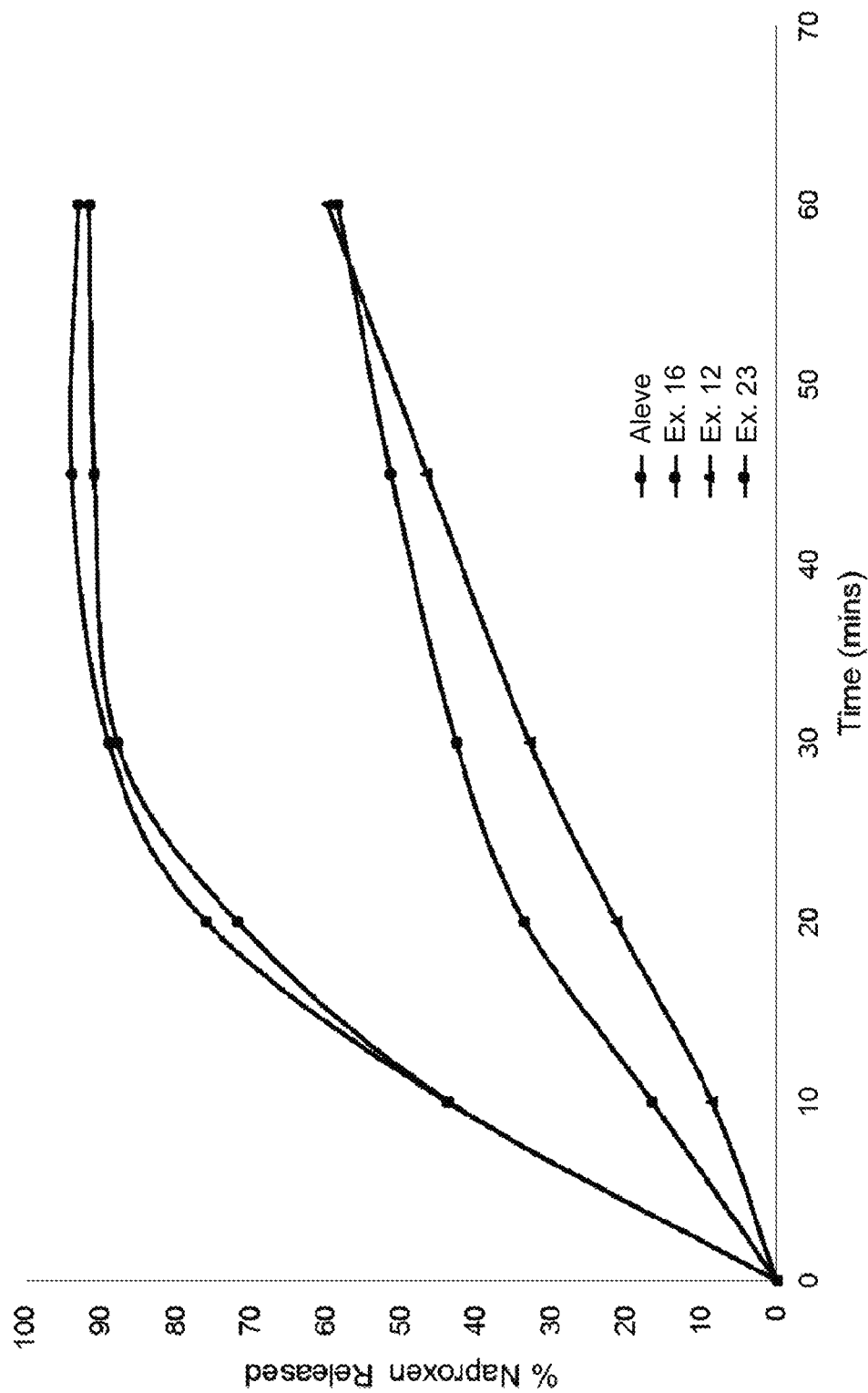
FIG. 8 shows naproxen dissolution results at pH 5.0 (simulated fed state) for embodiments of the present invention as well as commercially available Aleve®.
Figure 9:
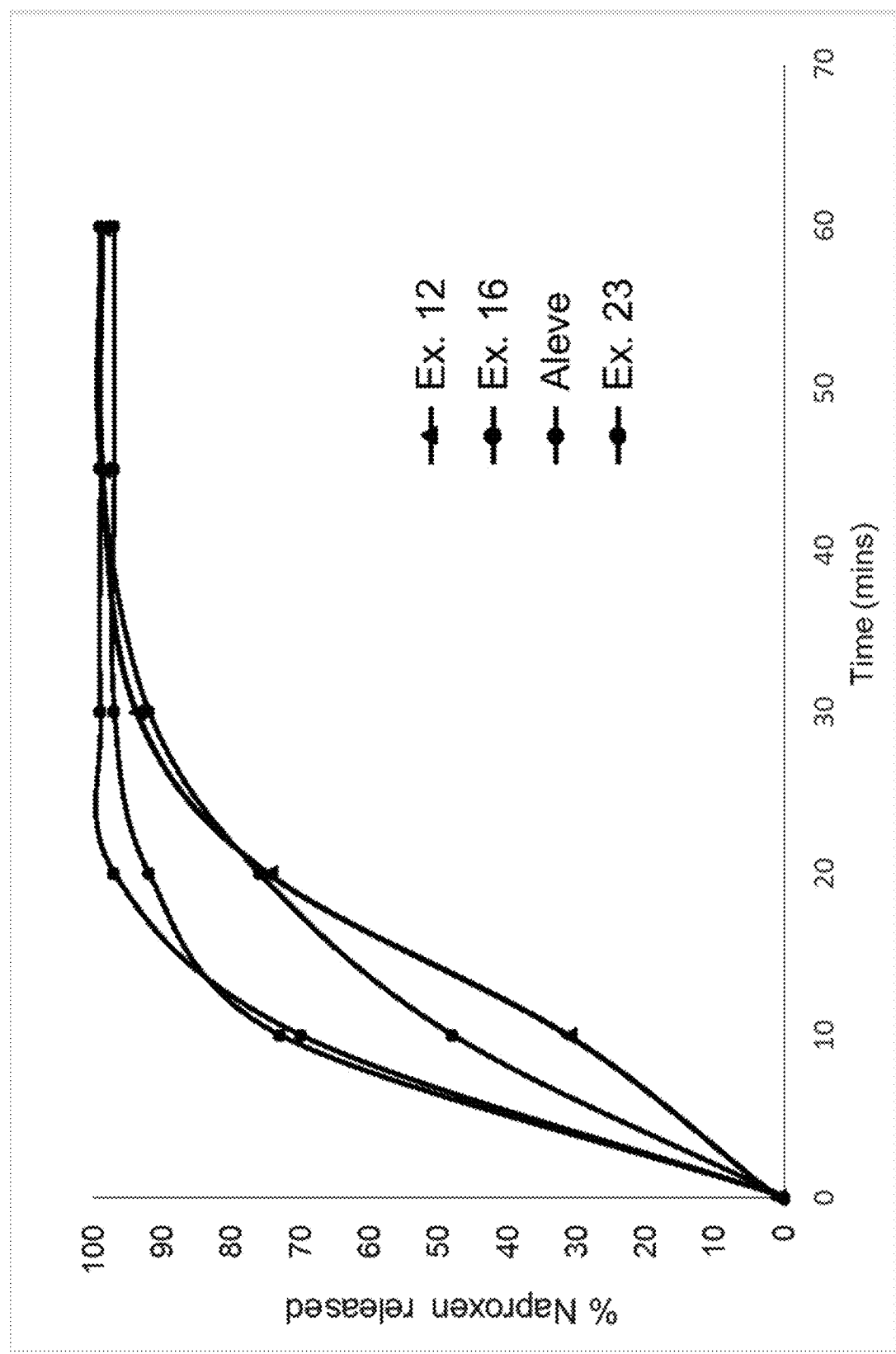
FIG. 9 shows naproxen dissolution results at pH 6.8 (simulated fasted state) for embodiments of the present invention as well as commercially available Aleve®.
Figure 10:
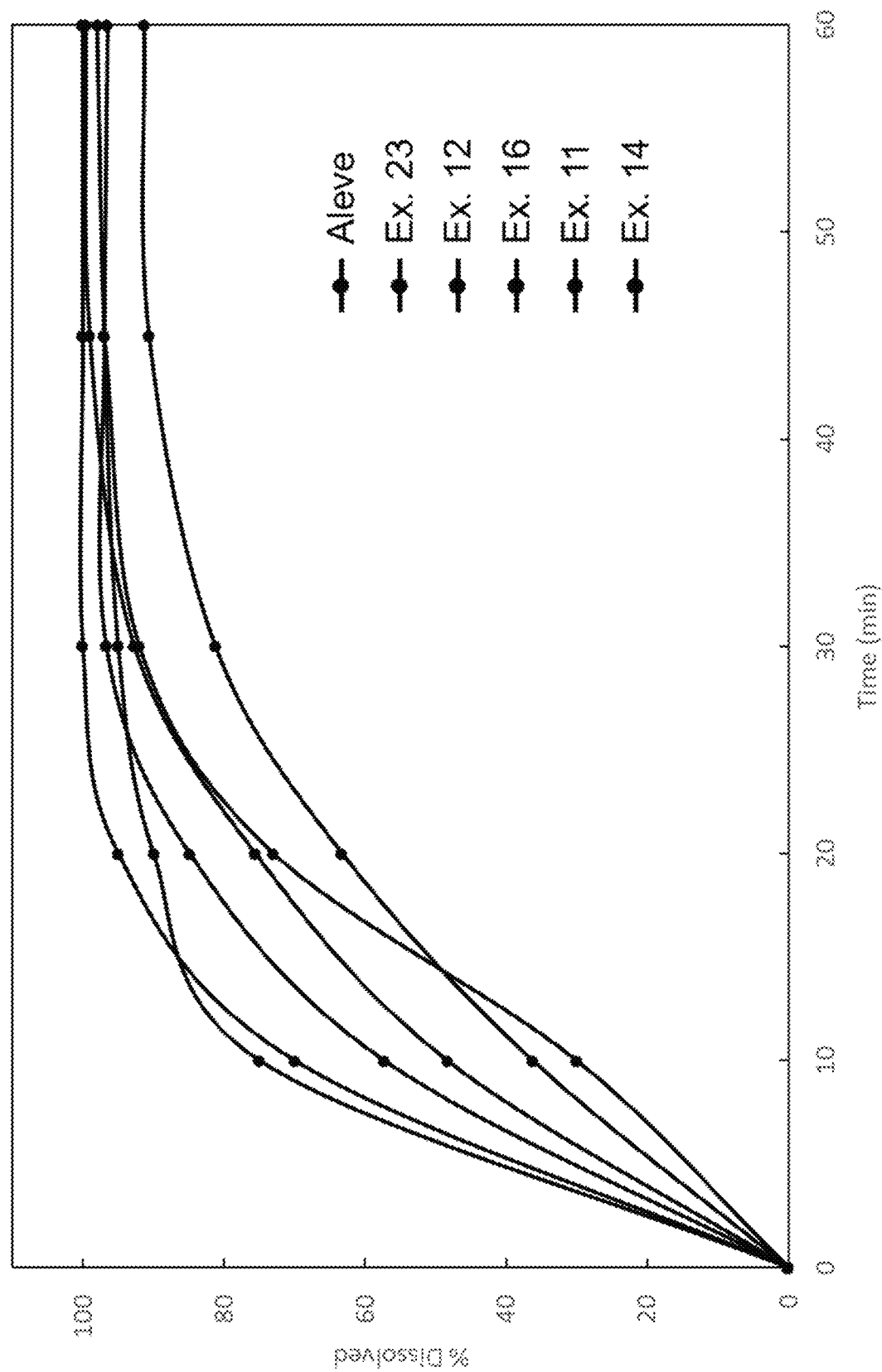
FIG. 10 shows naproxen dissolution results at pH 6.8 (simulated fasted state) for embodiments of an immediate release layer of the present invention as well as commercially available Aleve®.
Figure 11:
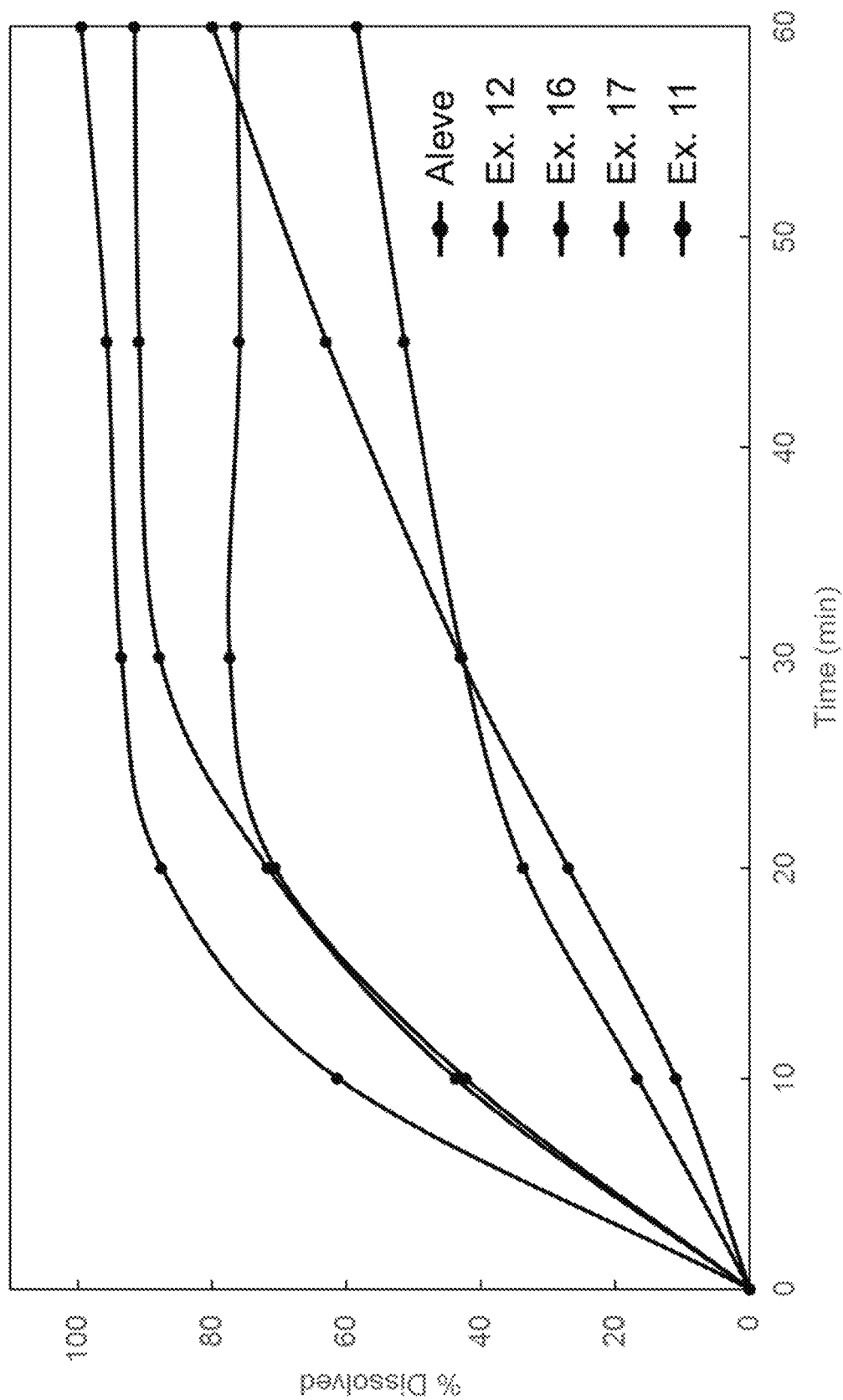
FIG. 11 shows naproxen dissolution results at pH 5.0 (simulated fed state) for embodiments of an immediate release layer of the present invention as well as commercially available Aleve®.
Figure 12:
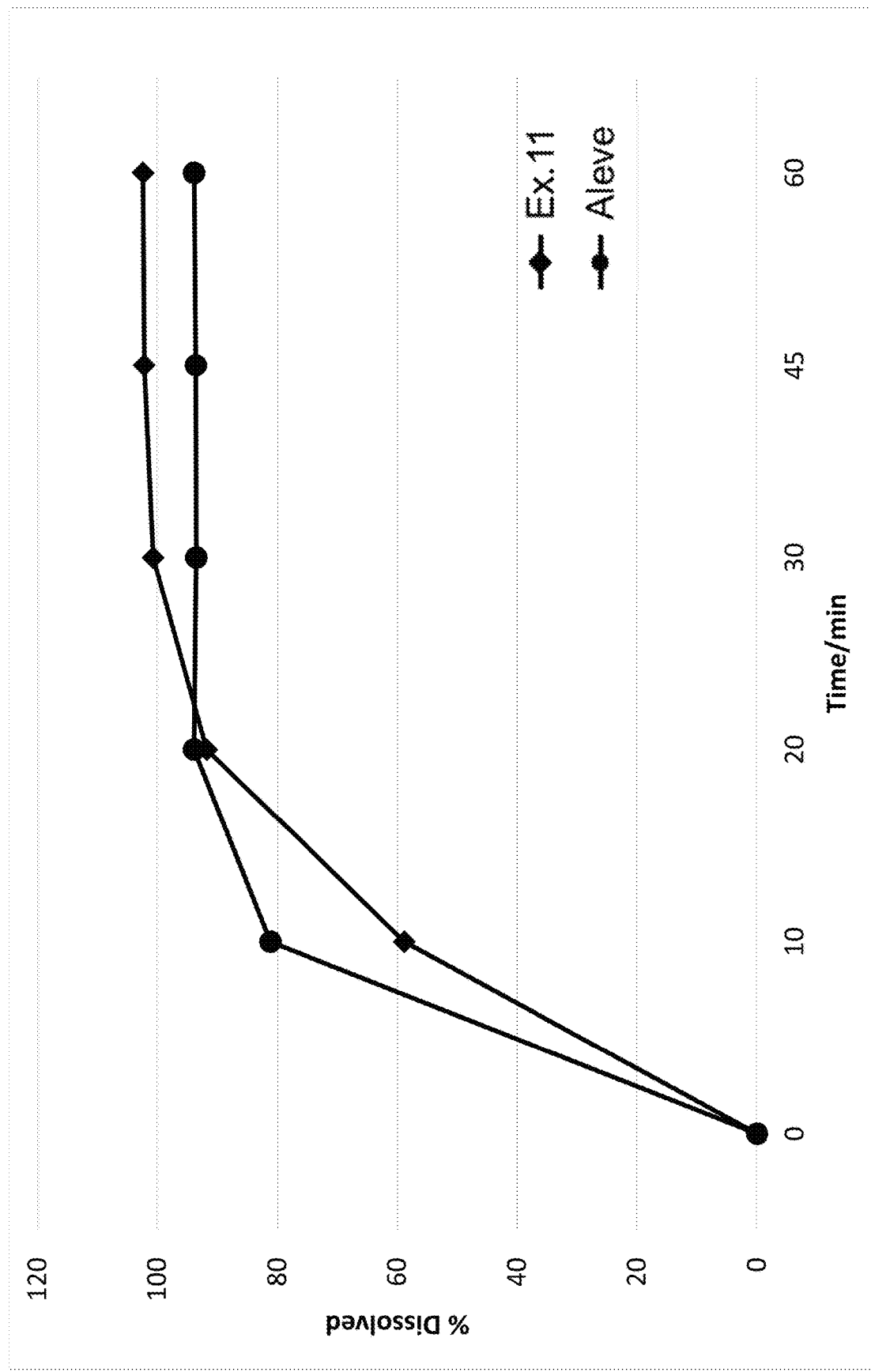
FIG. 12 shows naproxen dissolution results at pH 6.8 (simulated fasted state) for an embodiment of the present invention as well as commercially available Aleve®.

In addition, naproxen dissolution results comparing Aleve®, Example 23 and Example 12 are as shown in FIG. 7.

Particle Size Distribution Testing

Figure 6:
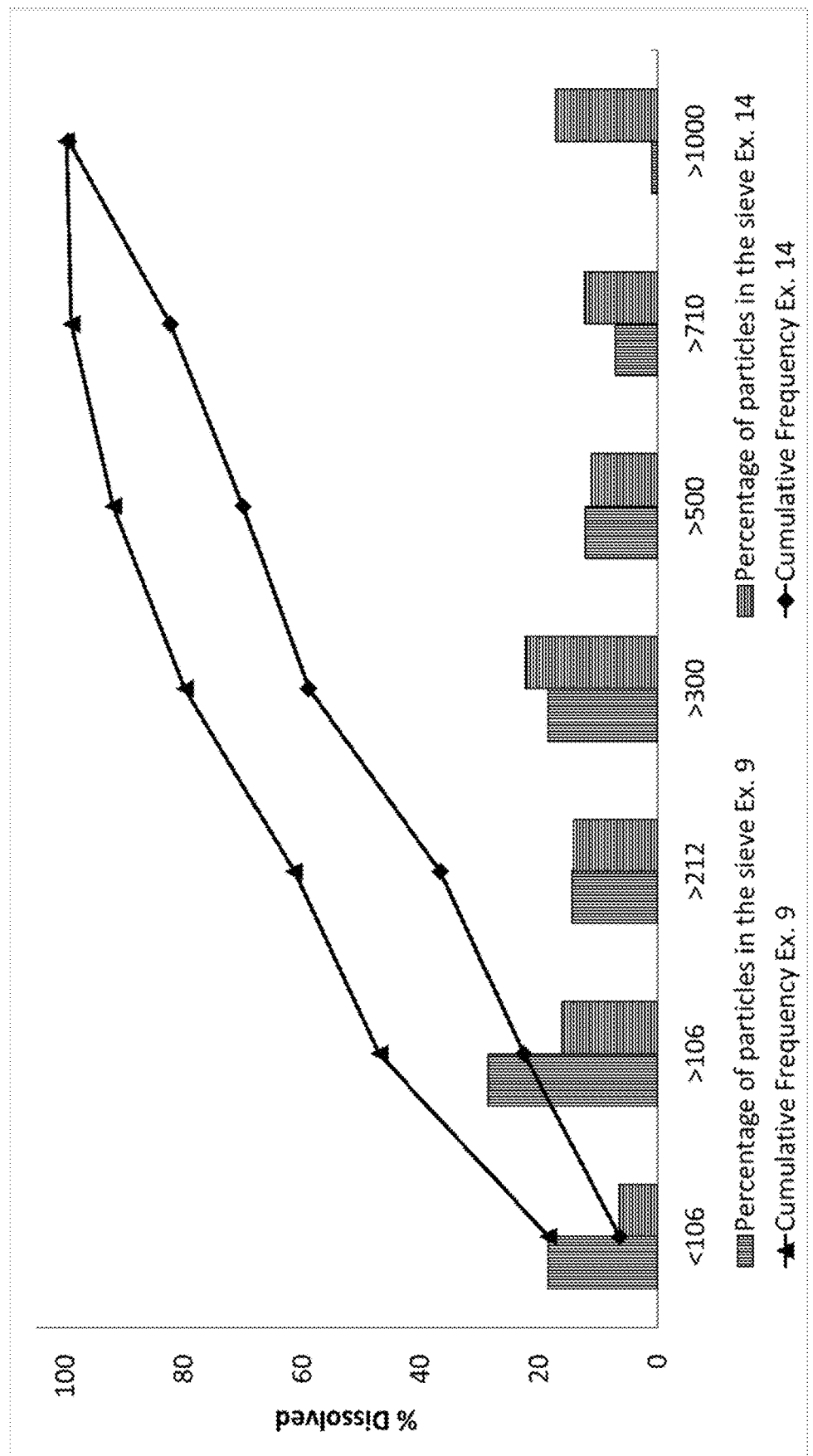
FIG. 6 shows a comparison of particle size distribution between different embodiments of the present invention.

Particle size distribution tests (USP General Test 786: agitate sieve for 5 minutes, weigh each sieve before sieving without material, and after sieving with material contained) were conducted for the immediate release layers of Examples 9 and 14. The results are shown in FIG. 6 and in Tables 16-17 below.

TABLE 16

Example 9

| Particle Size (μm) | Initial Sieve Weight | Final Sieve Weight | Mass of particles in sieve | Percentage of particles in the sieve | Cumulative Frequency |
|---|---|---|---|---|---|
| <106 | 247.27 | 265.66 | 18.39 | 18.48241206 | 18.48241206 |
| >106 | 422.27 | 450.61 | 28.34 | 28.48241206 | 46.96482412 |
| >212 | 445.68 | 460.01 | 14.33 | 14.40201005 | 61.36683417 |
| >300 | 453.16 | 471.49 | 18.33 | 18.42211055 | 79.78894472 |
| >500 | 480.22 | 492.28 | 12.06 | 12.12060302 | 91.90954774 |
| >710 | 505.54 | 512.58 | 7.04 | 7.075376884 | 98.98492462 |
| >1000 | 497.03 | 497.90 | 0.87 | 0.874371859 | 99.85929648 |
| Total Weight Added | 99.5 | | | | |

TABLE 17

Example 14
Wet Granulation

| Particle Size (μm) | Initial Sieve Weight | Final Sieve Weight | Mass of particles in sieve | Percentage of particles in the sieve | Cumulative Frequency |
|---|---|---|---|---|---|
| <106 | 248.06 | 254.48 | 6.42 | 6.419358064 | 6.419358064 |
| >106 | 418.75 | 434.87 | 16.12 | 16.11838816 | 22.53774623 |
| >212 | 278.22 | 292.30 | 14.08 | 14.07859214 | 36.61633837 |
| >300 | 451.04 | 473.31 | 22.27 | 22.26777322 | 58.88411159 |
| >500 | 477.67 | 488.76 | 11.09 | 11.08889111 | 69.9730027 |
| >710 | 503.6 | 515.91 | 12.31 | 12.30876912 | 82.28177182 |
| >1000 | 496.56 | 513.75 | 17.19 | 17.18828117 | 99.47005299 |
| Total Weight Added | 100.01 | | | | |

Bioavailability Testing

A pilot, phase I, open label, single dose, randomized, 5-period, 5-sequence, crossover relative bioavailability study of two combination modified-release formulations of 600 mg guaifenesin, 110 mg naproxen sodium and 30 mg dextromethorphan hydrobromide, dosed each as two capsules under fasted and fed conditions compared to a combination of Mucinex® DM and naproxen sodium reference products under fasted conditions was conducted.

As used herein, $C_{max}$ is the maximum blood serum concentration that is achieved from a dose and is a measure of how quickly a drug is released and absorbed. As used herein, AUC is the area under the curve in a concentration vs. time profile and is a measure of how much total drug a person is exposed to. As used herein, CI (confidence interval) is a range that a certain percentage of data points falls within and is a measure of the variability of the sample set. FDA guidance stipulates that $C_{max}$ and AUC mean values and 90% CI must be within 80%-125% to establish bioequivalency.

The following study treatment arms were used:

TABLE 18

| Treatment | Formula | Conditions |
|---|---|---|
| A | DG2/N1 | FASTED |
| B | DG2/N1 | FED |
| C | DG1/N2 | FASTED |
| D | DG1/N2 | FED |
| E | REFERENCE* | FASTED |

*Reference treatment is 2 Mucinex ® DM 600/30 mg tablets and 1 Aleve ® 220 mg tablet.

The following are descriptions of the study treatment arms:

Treatment A—Capsule DG2/N1 (After 10-hour Fast): Two (2) capsules each containing an extended-release bi-layer tablet with 600 mg guaifenesin and 30 mg dextromethorphan hydrobromide and a "fast" immediate-release tablet with 110 mg naproxen sodium, administered with 240 ml of water after an overnight fast of at least 10 hours.

Treatment B—Capsule DG2/N1 (After a High-Fat Meal): Two (2) capsules each containing an extended-release bi-layer tablet with 600 mg guaifenesin and 30 mg dextromethorphan hydrobromide and a "fast" immediate-release tablet with 110 mg naproxen sodium, administered with 240 ml of water 30 minutes after the beginning of the consumption of a high-fat standardized breakfast, preceded by an overnight fast of at least 10 hours.

Treatment C—Capsule DG1/N2 (After 10-hour Fast): Two (2) capsules each containing an extended-release bi-layer tablet with 600 mg guaifenesin and 30 mg dextromethorphan hydrobromide and a "slow" immediate release tablet with 110 mg naproxen sodium, administered with 240 ml of water after an overnight fast of at least 10 hours.

Treatment D—Capsule DG1/N2 (After a High-Fat Meal): Two (2) capsules each containing an extended-release bi-layer tablet with 600 mg guaifenesin and 30 mg dextromethorphan hydrobromide and a "slow" immediate release tablet with 110 mg naproxen sodium, administered with 240 ml of water 30 minutes after the beginning of the consumption of a high-fat standardized breakfast, preceded by an overnight fast of at least 10 hours.

Treatment E—Reference (After 10-hour Fast): Two Mucinex® DM (600 mg guaifenesin, 30 mg dextromethorphan hydrobromide) extended-release bi-layer tablets and one Aleve® tablet (220 mg naproxen sodium) administered with 240 ml of water after an overnight fast of at least 10 hours.

The following bilayer tablet formulations were used as the DG1 and DG2 sustained release formulae (Table 19) and the naproxen tablet formulations N1 and N2 (Table 20):

TABLE 19

| | Component | Current Mucinex ® DM 600 Mg/tablet | DG1 Mg/tablet | DG2 Mg/tablet |
|---|---|---|---|---|
| IR | Guaifenesin | 95.00 | 95.00 | 70.00 |
| | Dextromethorphan HBr | 7.50 | 7.50 | 4.50 |
| | Microcrystalline cellulose | 87.52 | 87.52 | 112.40 |

TABLE 19-continued

| | Component | Current Mucinex® DM 600 Mg/tablet | DG1 Mg/tablet | DG2 Mg/tablet |
|---|---|---|---|---|
| | Hypromellose | 5.00 | 5.00 | |
| | Sodium starch glycolate | 3.98 | 3.98 | |
| | Povidone | | | 7.00 |
| | Croscarmellose sodium | | | 6.00 |
| | Magnesium stearate | 1.00 | 1.00 | 1.00 |
| | Total IR | 200.00 | 200.00 | 200.00 |
| MR | Guaifenesin | 505.00 | 505.00 | 530.00 |
| | Dextromethorphan HBr | 22.50 | 22.50 | 25.50 |
| | Hypromellose | 25.00 | 45.00 | |
| | Carbomer homopolymer type B | 7.50 | 7.50 | |
| | Hypromellose | | | 19.00 |
| | Hydroxyethylcellulose | | | 9.00 |
| | Microcrystalline cellulose | | | 17.00 |
| | Colorant | 0.20 | 0.20 | 0.20 |
| | Magnesium stearate | 5.00 | 5.00 | 1.80 |
| | Total MR | 565.20 | 285.20 | 602.50 |
| | Total tablet | 765.20 | 785.20 | 802.50 |

TABLE 20

| Component | Aleve® tablet Mg/tablet | N1 Mg/tablet | N2 Mg/tablet |
|---|---|---|---|
| Naproxen sodium | 220.00 | 110.00 | 110.00 |
| Microcrystalline cellulose | n/a | 81.00 | 34.45 |
| Povidone | n/a | 7.50 | 4.50 |
| Croscarmellose sodium | | 15.00 | |
| Magnesium stearate | n/a | 1.50 | 1.05 |
| Hypromellose | n/a | | |
| Polyethylene glycol | n/a | | |
| Talc | n/a | | |
| Colorant | n/a | | |
| Titanium dioxide | n/a | | |
| | ~300 | 215.00 | 150.00 |

Figure 14A:
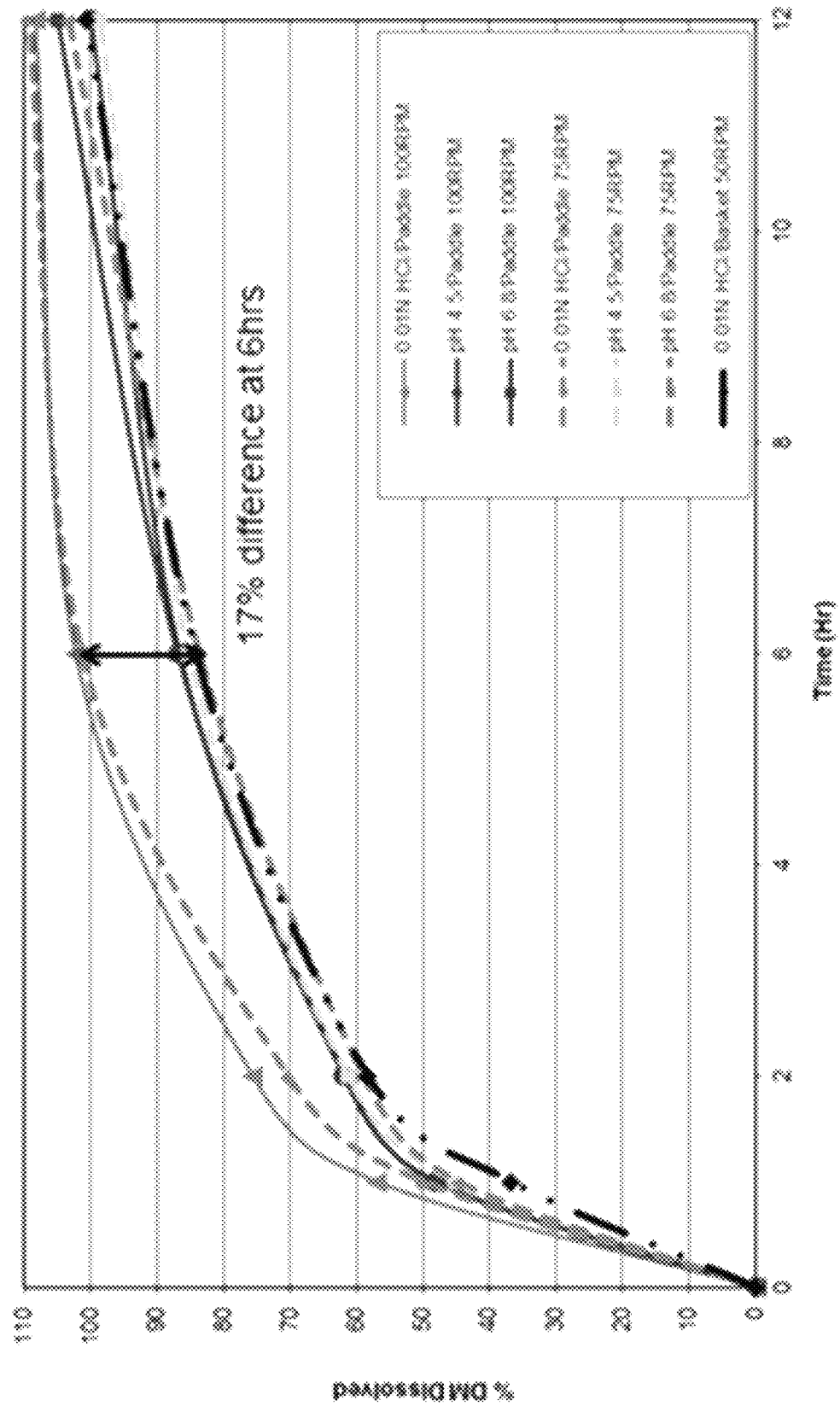
FIGS. 14A, 14B, and 14C show dextromethorphan dissolution results for an embodiment of the present invention as well as commercially available Mucinex® DM.
Figure 14B:
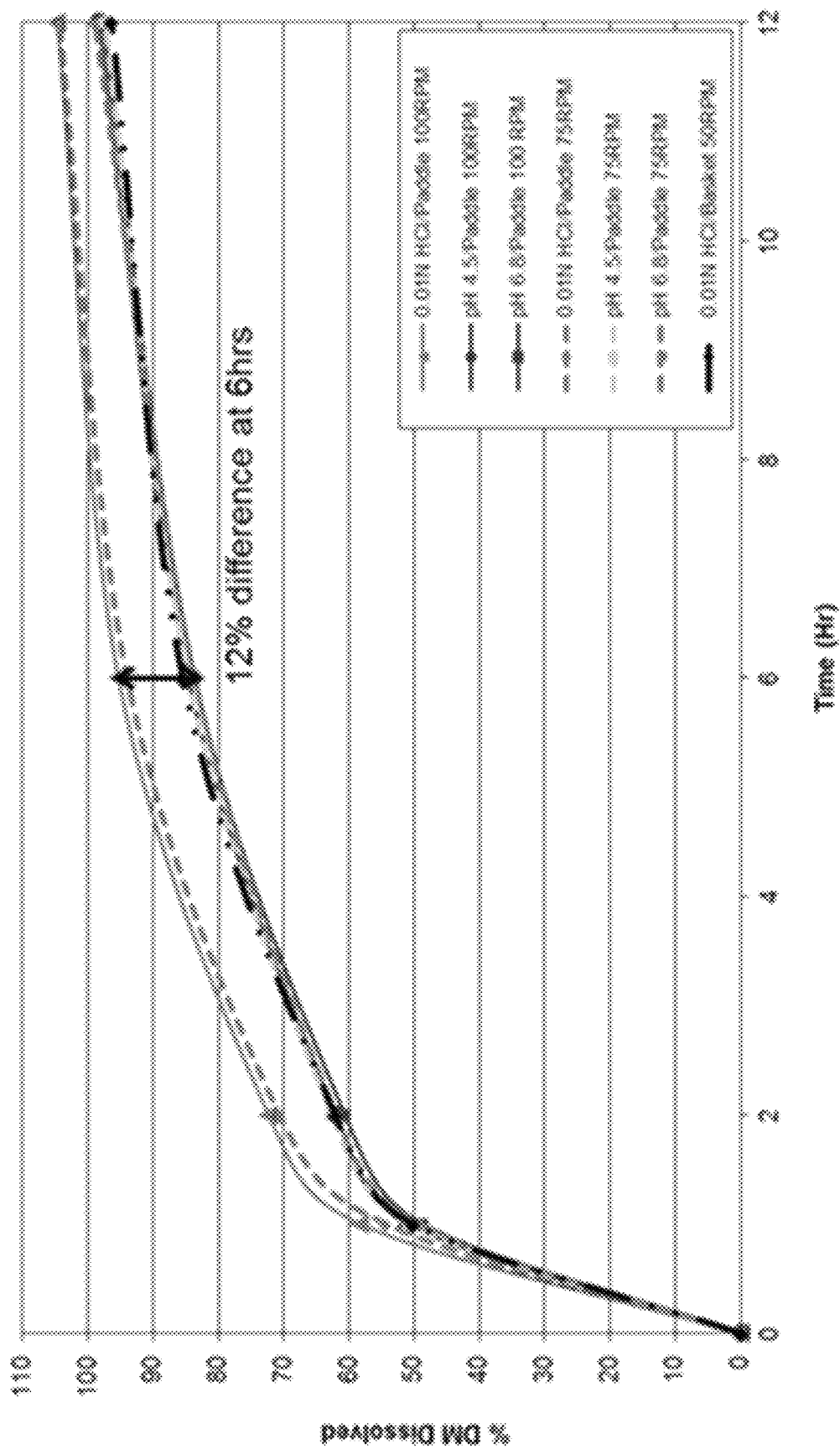
Figure 14C:
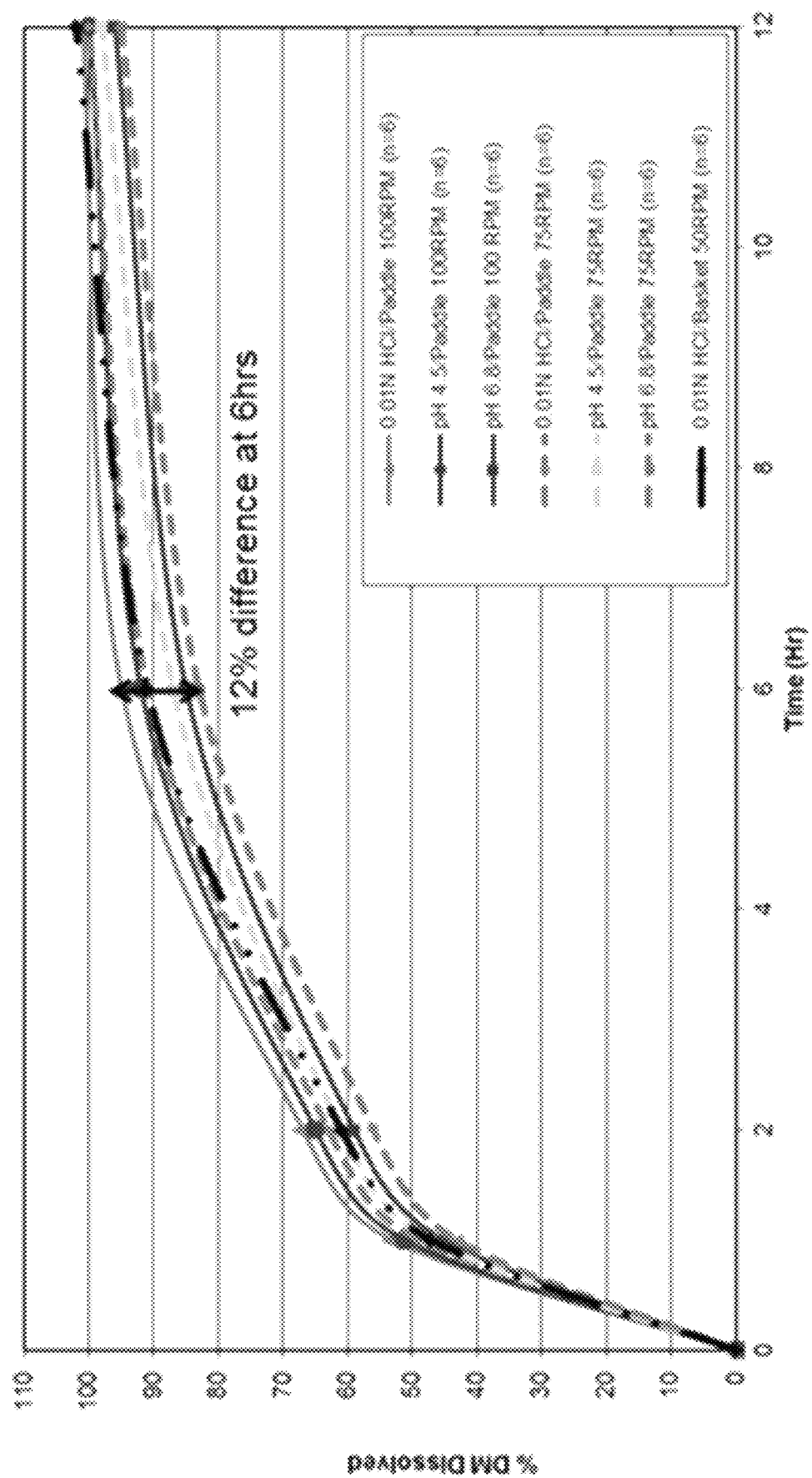
Figure 15A:
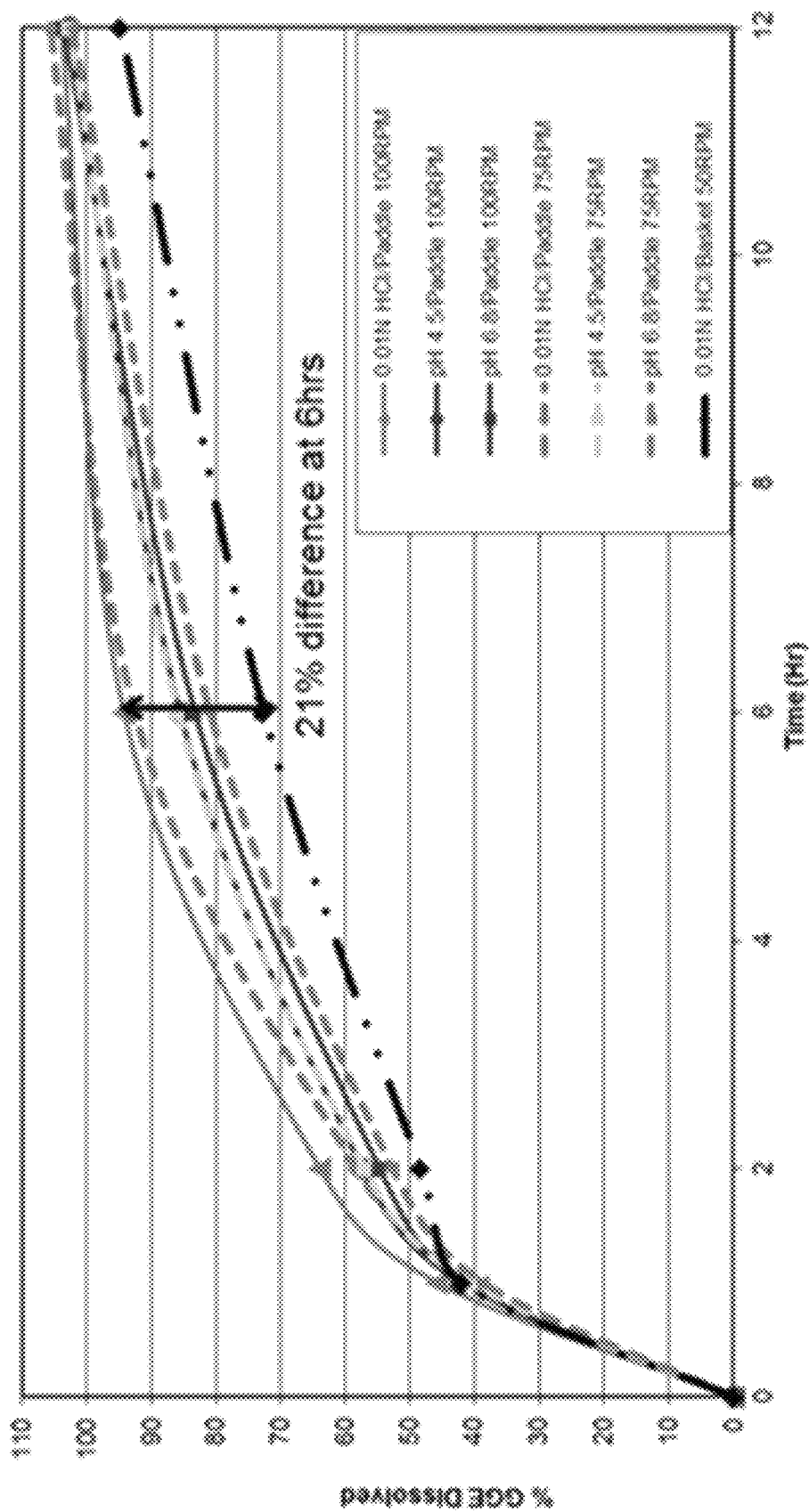
FIGS. 15A, 15B, and 15C show guaifenesin dissolution results for embodiments of the present invention as well as commercially available Mucinex® DM.
Figure 15B:
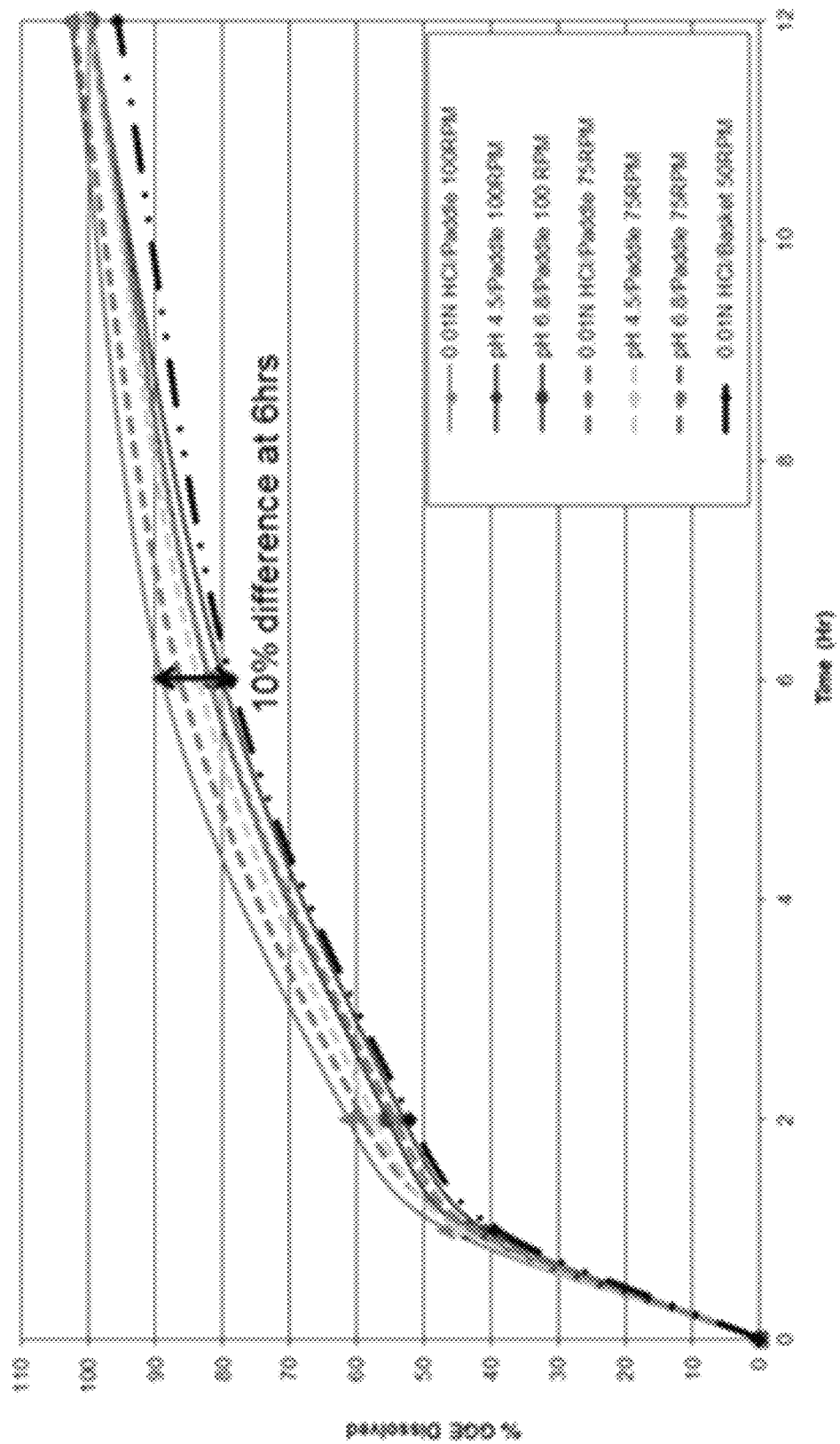
Figure 15C:
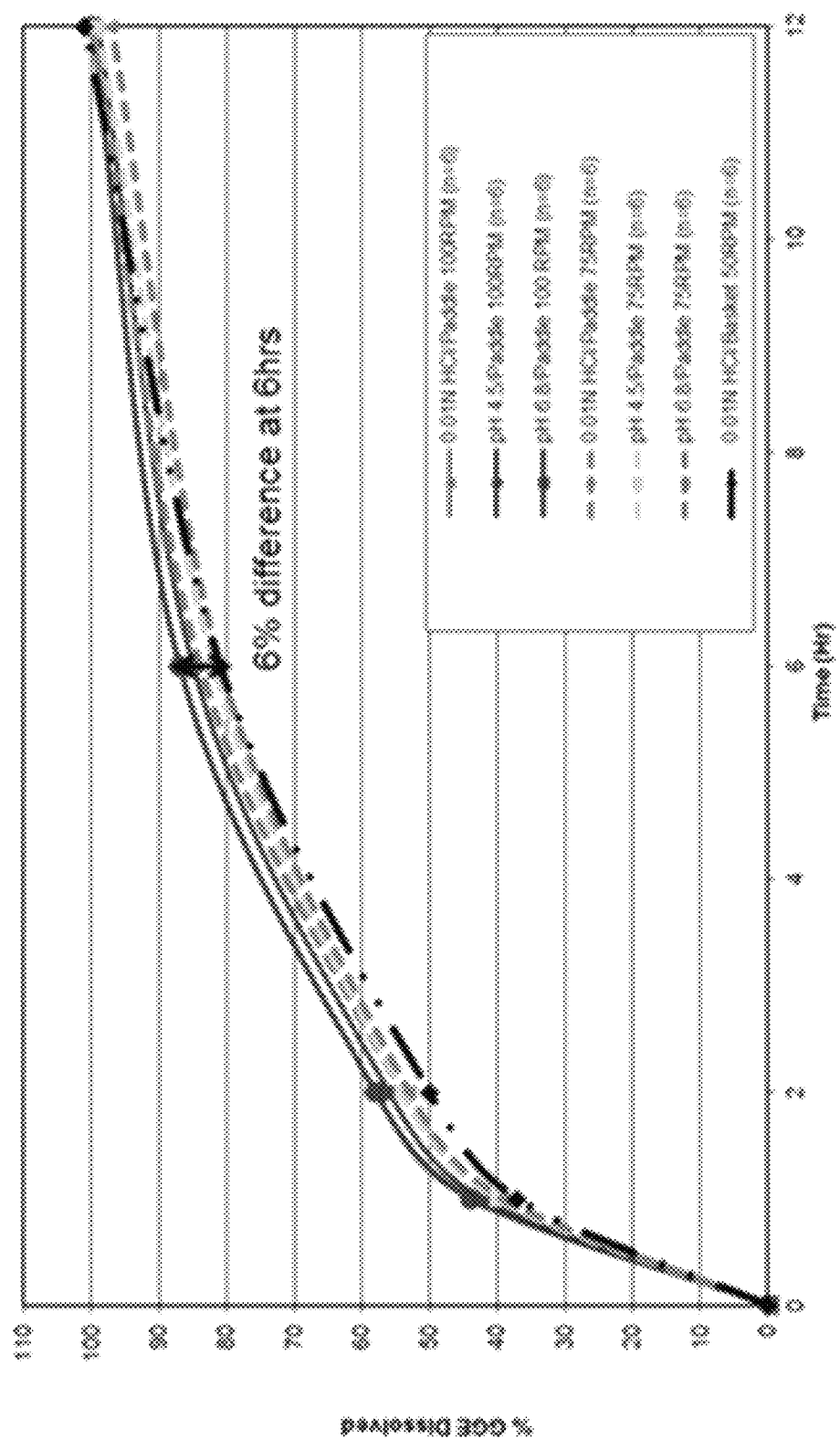
Figure 16:
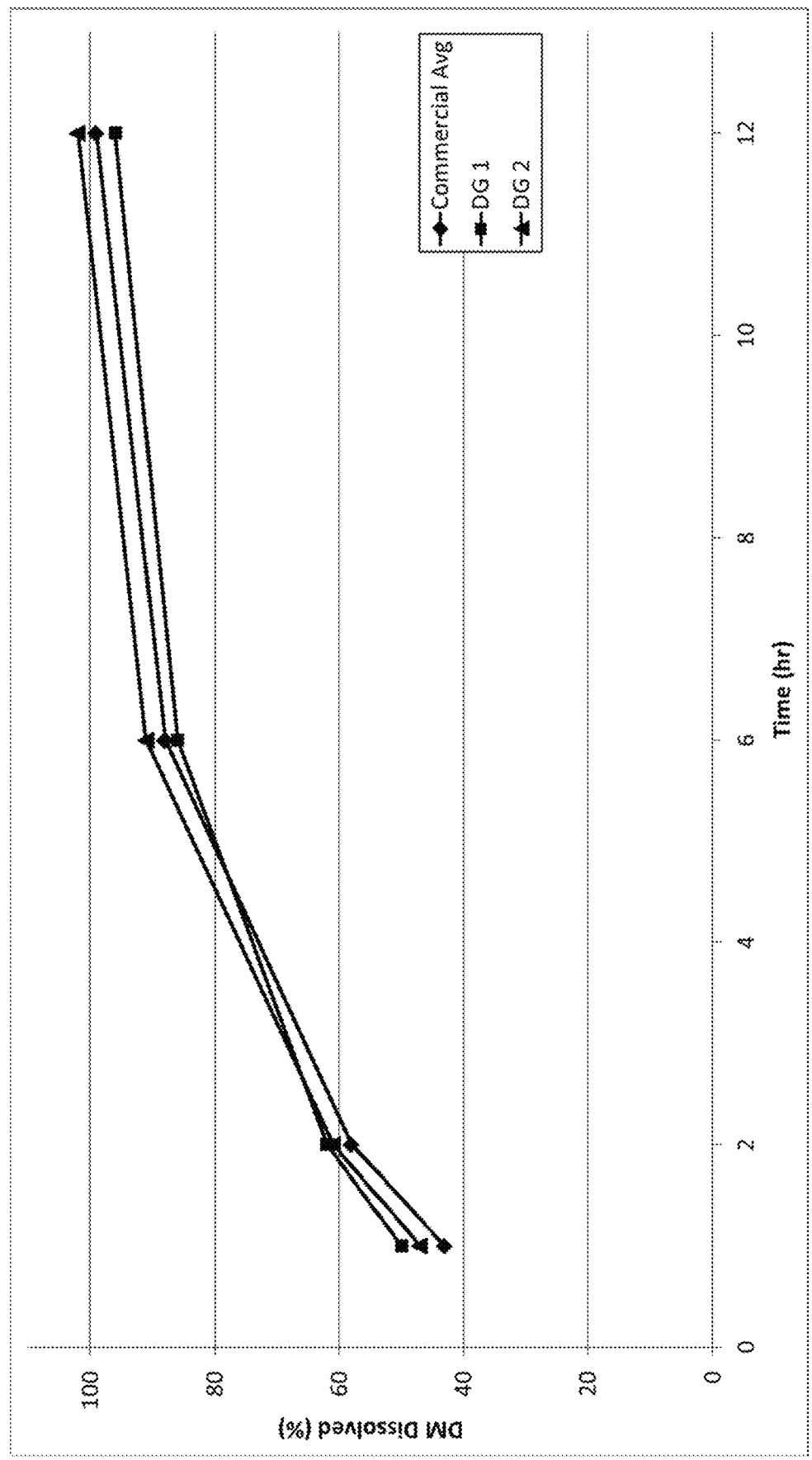
FIG. 16 shows dextromethorphan dissolution results at pH 2.0 for embodiments of the present invention as well as commercially available Mucinex® DM.
Figure 17:
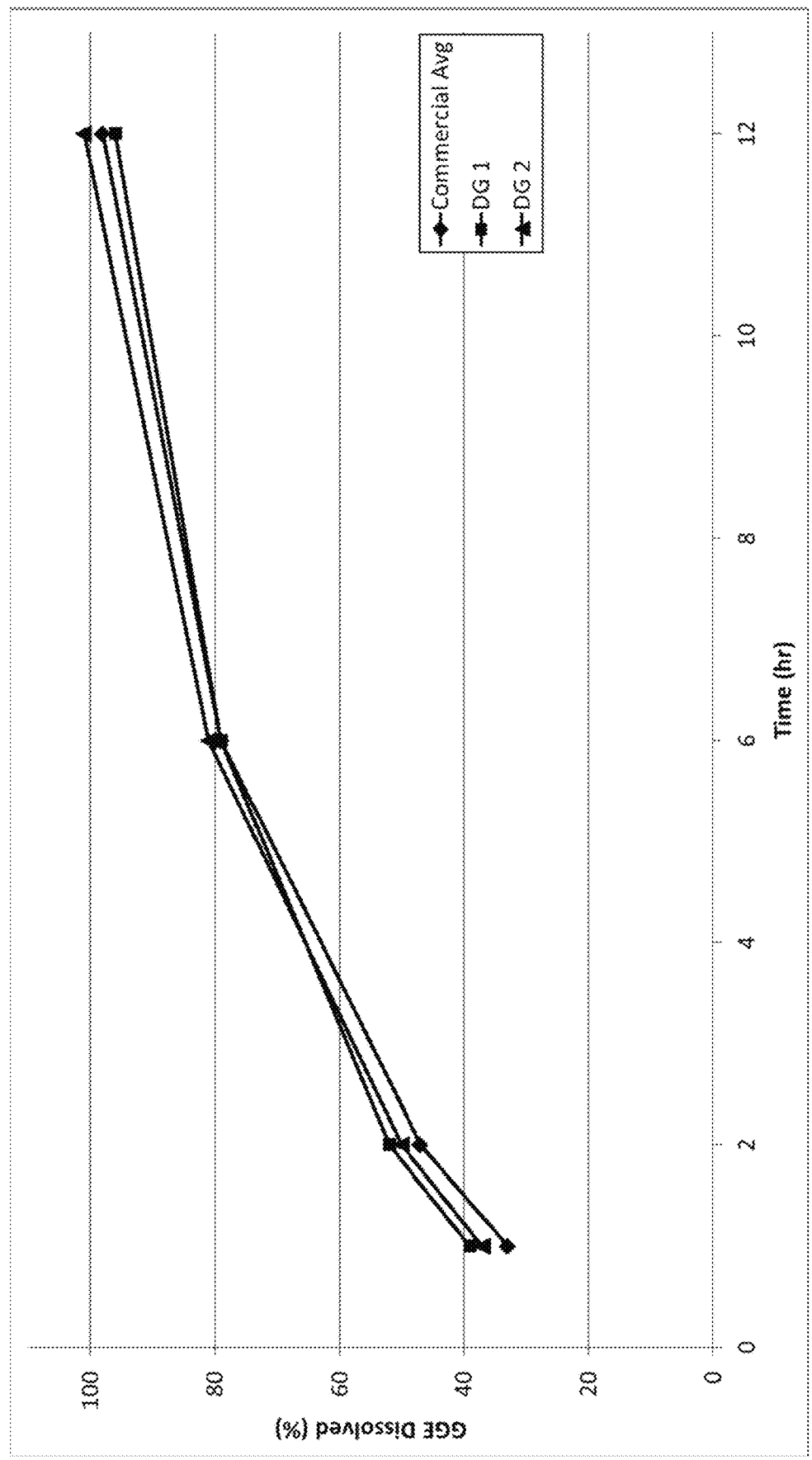
FIG. 17 shows guaifenesin dissolution results at pH 2.0 for embodiments of the present invention as well as commercially available Mucinex® DM.
Figure 18:
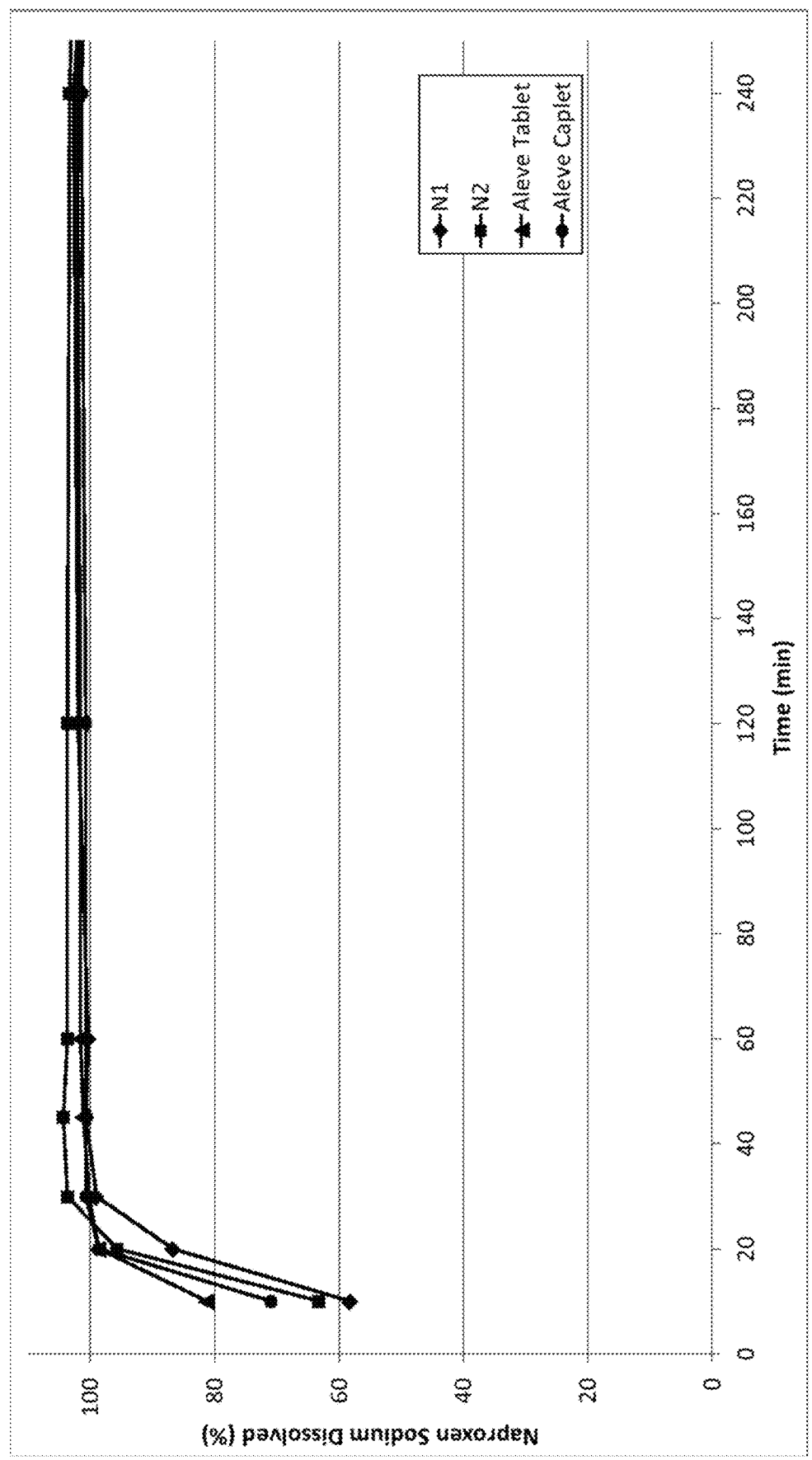
FIG. 18 shows naproxen dissolution results for embodiments of the invention as well as commercially available Aleve® tablets and caplets.

Dextromethorphan dissolution profiles for each of Mucinex® DM, DG1 and DG2 were determined as shown in FIGS. 14A, 14B, and 14C. Guaifenesin dissolution profiles for each of Mucinex® DM, DG1 and DG2 were determined as shown in FIGS. 15A, 15B, and 15C. In addition, FIG. 16 and Table 21 show dextromethorphan dissolution (pH 2, 0.01N HCl, basket, 50 RPM) for each of Mucinex® DM, DG1 and DG2, while FIG. 17 and Table 22 show guaifenesin dissolution (pH 2, 0.01N HCl, basket, 50 RPM) for each of Mucinex® DM, DG1 and DG2. FIG. 18 shows naproxen dissolution (pH 7.4, paddle, 50 RPM, 50 mM phosphate buffer) for each of Aleve® tablet, Aleve® caplet, N1 and N2.

TABLE 21

Dextromethorphan dissolution.

| Time (hr) | Lower Limit (%) | Upper Limit (%) | Commercial Avg (%) | Modified Bilayer (%) | New Bialyer (%) |
|---|---|---|---|---|---|
| 1 | 31 | 51 | 43 | 50 | 47 |
| 2 | 48 | 68 | 58 | 62 | 61 |
| 6 | 80 | 100 | 88 | 86 | 91 |
| 12 | 91 | 104 | 99 | 96 | 102 |
| | | | f2 | 66.5 | 72.3 |

TABLE 22

Guaifenesin dissolution.

| Time (hr) | Lower Limit (%) | Upper Limit (%) | Commercial Avg (%) | Modified Bilayer (%) | New Bialyer (%) |
|---|---|---|---|---|---|
| 1 | 23 | 43 | 33 | 39 | 37 |
| 2 | 37 | 57 | 47 | 52 | 50 |
| 6 | 72 | 92 | 79 | 79 | 81 |
| 12 | 90 | 104 | 98 | 96 | 101 |
| | | | f2 | 68.1 | 73.0 |

Figure 19:
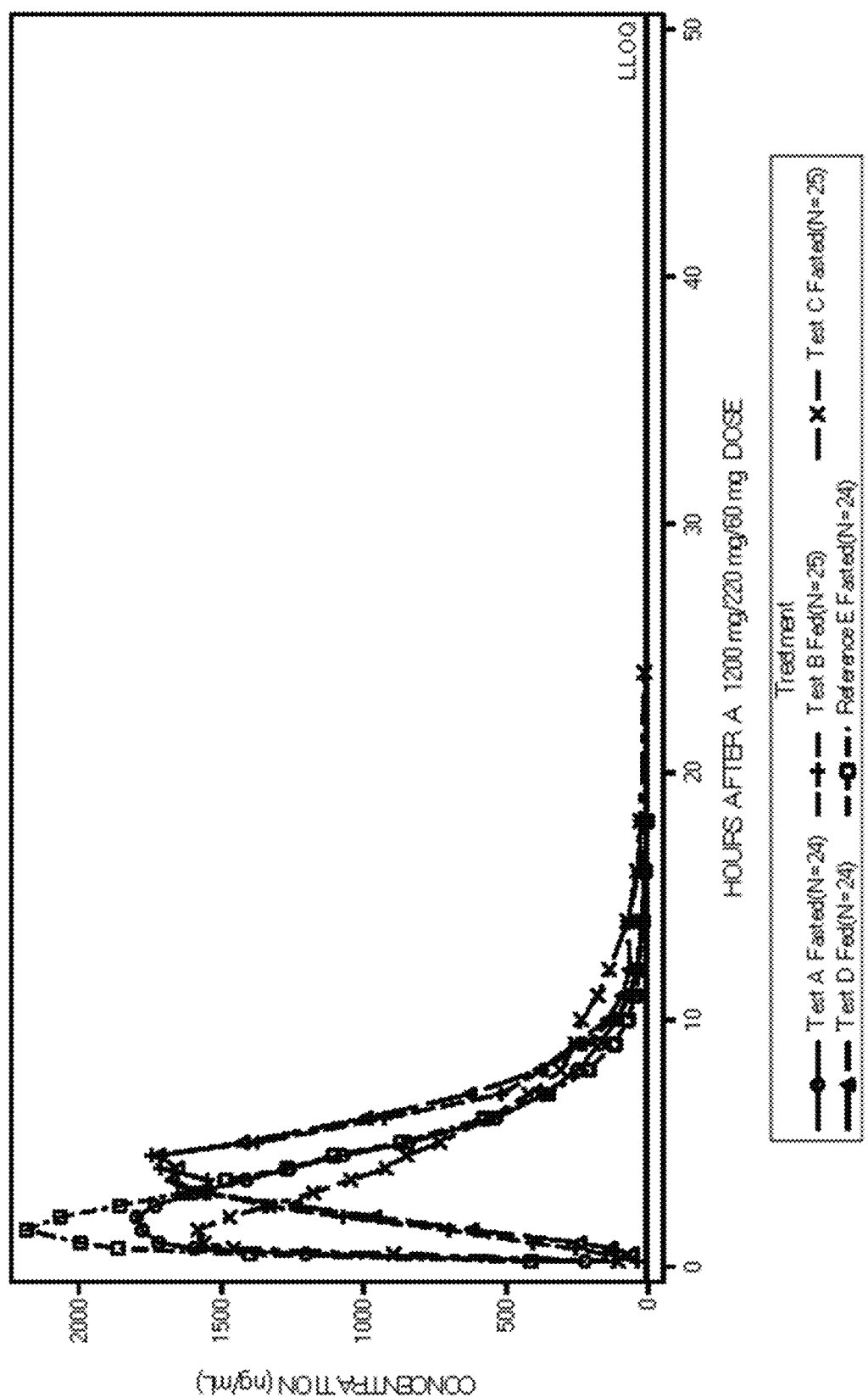
FIG. 19 shows mean plasma guaifenesin concentration results for various treatments with embodiments of the present invention.
Figure 20:
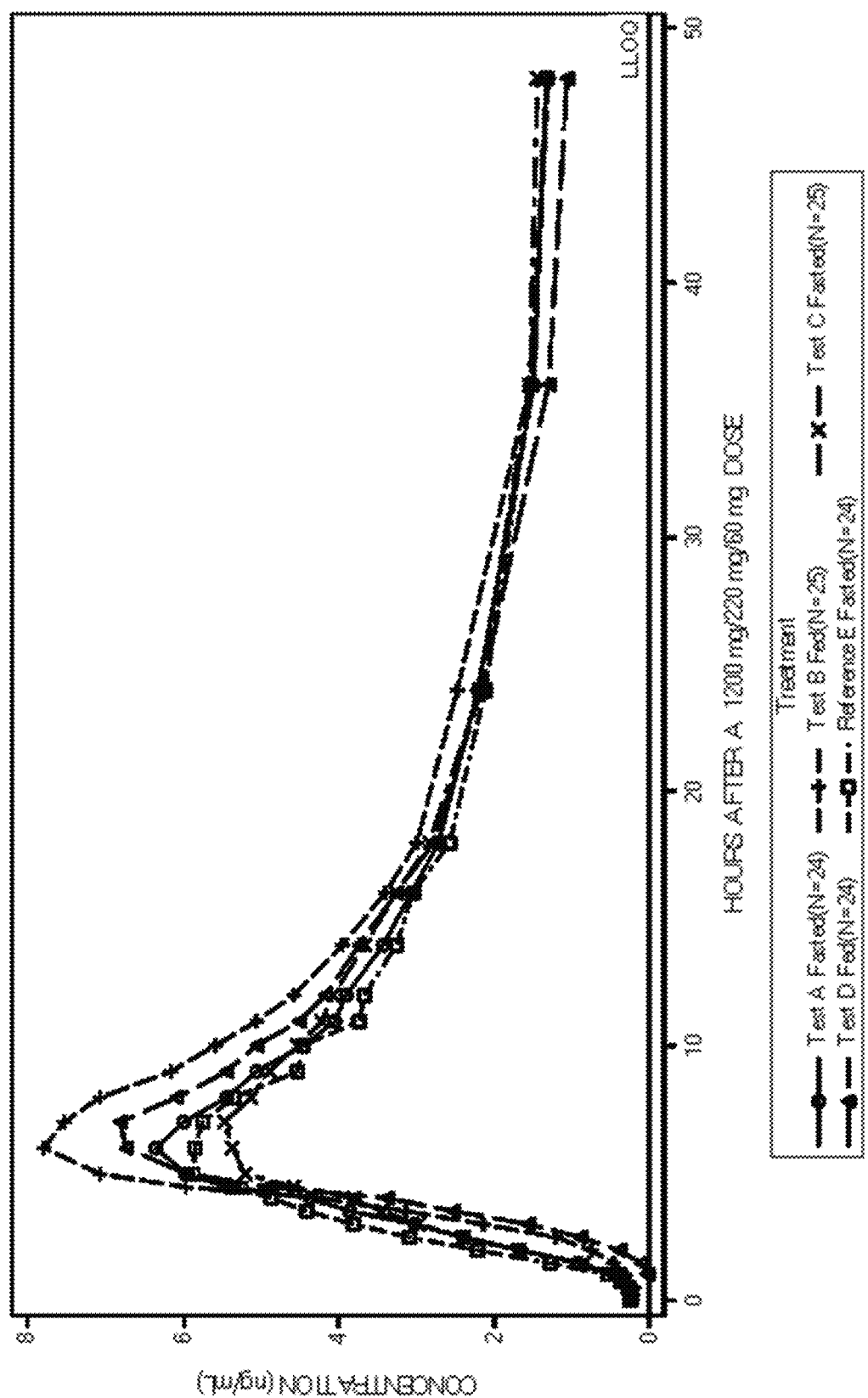
FIG. 20 shows mean plasma dextromethorphan concentration results for various treatments with embodiments of the present invention.
Figure 21:
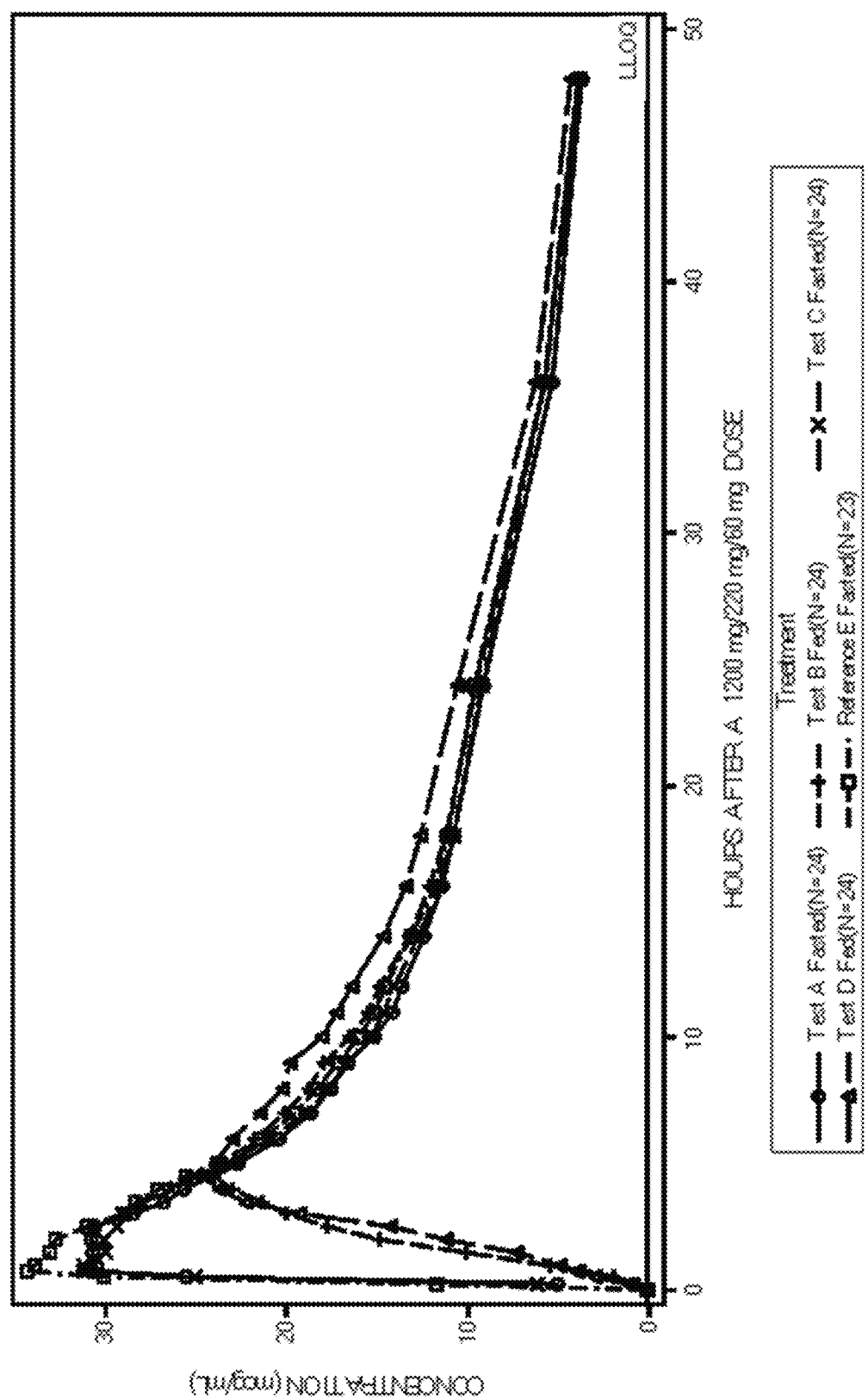
FIG. 21 shows mean plasma naproxen concentration results for various treatments with embodiments of the present invention.

Plasma guaifenesin, dextromethorphan, and naproxen concentrations were determined for each of the treatments above by known methods and were as shown in FIGS. 19-21, respectively. Further, $AUC_{0-t}$, $AUC_{0-inf}$ and $C_{max}$ were determined as follows in Tables 23-25:

TABLE 23

Guaifenesin parameters.

| | $AUC_{0-t}$ (%) | $AUC_{0-inf}$ (%) | $C_{max}$ (%) |
|---|---|---|---|
| Fast/Fasted Vs Reference (A Vs E) | 94.62 | 94.66 | 88.18 |
| Fast/Fed Vs Fast/Fasted (B Vs A) | 94.18 | 94.16 | 103.79 |
| Slow/Fasted Vs Reference (C Vs E) | 88.77 | 89.08 | 77.55 |
| Slow/Fed Vs Slow/Fasted (D Vs C) | 100.42 | 100.17 | 105.24 |

TABLE 24

Dextromethorphan parameters.

| | $AUC_{0-t}$ (%) | $AUC_{0-inf}$ (%) | $C_{max}$ (%) |
|---|---|---|---|
| Fast/Fasted Vs Reference (A Vs E) | 101.86 | 101.39 | 99.77 |
| Fast/Fed Vs Fast/Fasted (B Vs A) | 117.55 | 118.85 | 130.61 |
| Slow/Fasted Vs Reference (C Vs E) | 109.89 | 110.31 | 92.16 |
| Slow/Fed Vs Slow/Fasted (D Vs C) | 106.90 | 106.73 | 130.58 |

TABLE 25

Naproxen parameters.

| | $AUC_{0-t}$ (%) | $AUC_{0-inf}$ (%) | $C_{max}$ (%) |
|---|---|---|---|
| Fast/Fasted Vs Reference (A Vs E) | 94.66 | 95.14 | 90.97 |
| Fast/Fed Vs Fast/Fasted (B Vs A) | 94.25 | 96.51 | 73.31 |

TABLE 25-continued

Naproxen parameters.

| | AUC$_{0-t}$ (%) | AUC$_{0-inf}$ (%) | C$_{max}$ (%) |
|---|---|---|---|
| Slow/Fasted Vs Reference (C Vs E) | 97.80 | 99.14 | 93.34 |
| Slow/Fed Vs Slow/Fasted (D Vs C) | 97.91 | 98.92 | 71.74 |

The tested compositions according to the present invention also provide for more consistent release of both guaifenesin and dextromethorphan when compared to current commercial products in various pH conditions and when exposed to various agitation speeds. For example purposes only, these formulations have been shown to improve the consistency of dextromethorphan release after 6 hours by 29% and guaifenesin release after 6 hours by 52% and 71% as shown above.

Numerous alterations, modifications, and variations of the preferred embodiments disclosed herein will be apparent to those skilled in the art, and they are all anticipated and contemplated to be within the spirit and scope of the claimed invention. For example, although specific embodiments have been described in detail, those with skill in the art will understand that the preceding embodiments and variations can be modified to incorporate various types of substitute, additional, or alternative materials. Accordingly, even though only few variations of the present invention are described herein, it is to be understood that the practice of such additional modifications and variations and the equivalents thereof, are within the spirit and scope of the invention as defined in the following claims. All patent applications, patents, and other publications cited herein are incorporated by reference in their entirety.

What is claimed is:

1. A pharmaceutical composition comprising:
   (a) about 600 mg of guaifenesin;
   (b) about 30 mg of dextromethorphan or a pharmaceutically acceptable salt thereof;
   (c) about 110 mg of naproxen or a pharmaceutically acceptable salt thereof;
   (d) about 18 to 28 mg of hypromellose; and
   (e) about 8 to 14 mg of hydroxyethyl cellulose;
   wherein the pharmaceutical composition provides a therapeutic effect in respect of each of guaifenesin, naproxen, and dextromethorphan for 12 hours,
   wherein substantially all of naproxen dissolves within 30 minutes in a pH 6.8 phosphate buffer, and
   wherein the pharmaceutical composition is a bilayer tablet comprising an immediate release layer containing substantially all of the naproxen and at least about 100 mg of the guaifenesin and at least about 8 mg of the dextromethorphan, wherein the immediate release layer contains none of the hypromellose, and wherein the immediate release layer contains none of the hydroxyethyl cellulose.

2. The pharmaceutical composition of claim 1, further comprising 0.1-2% of sodium lauryl sulfate by weight of the total composition and 1-10% sodium bicarbonate by weight of the total composition.

3. The pharmaceutical composition of claim 2, wherein the sodium lauryl sulfate is in an amount of about 10-11 mg and the sodium bicarbonate is in an amount of about 30-60 mg.

4. The pharmaceutical composition of claim 3, wherein the immediate release layer contains substantially all of the sodium lauryl sulfate and substantially all of the sodium bicarbonate.

5. A pharmaceutical composition comprising:
   (a) about 600 mg of guaifenesin;
   (b) about 30 mg of dextromethorphan or a pharmaceutically acceptable salt thereof;
   (c) about 110 mg of naproxen or a pharmaceutically acceptable salt thereof;
   (d) about 10-11 mg of sodium lauryl sulfate; and
   (e) about 30-60 mg of sodium bicarbonate;
   wherein the pharmaceutical composition provides a therapeutic effect in respect of each of guaifenesin, naproxen, and dextromethorphan for 12 hours,
   wherein substantially all of naproxen dissolves within 30 minutes in a pH 6.8 phosphate buffer, and
   wherein the pharmaceutical composition is a bilayer tablet comprising an immediate release layer containing substantially all of the naproxen and at least about 100 mg of the guaifenesin and at least about 8 mg of the dextromethorphan, wherein the immediate release layer contains substantially all of the sodium lauryl sulfate and substantially all of the sodium bicarbonate.

6. The pharmaceutical composition of claim 5, further comprising 1-8% hypromellose by weight of the total composition and 1-2% hydroxyethyl cellulose by weight of the total composition.

7. The pharmaceutical composition of claim 6, wherein the hypromellose is in an amount of about 18 to 28 mg and the hydroxyethyl cellulose is in an amount of about 8 to 14 mg.

8. The pharmaceutical composition of claim 7, wherein the immediate release layer contains none of the hypromellose, and wherein the immediate release layer contains none of the hydroxyethyl cellulose.

* * * * *